United States Patent
Jezek et al.

(10) Patent No.: US 12,357,562 B2
(45) Date of Patent: Jul. 15, 2025

(54) INJECTION PEN SYSTEM FOR THE DELIVERY OF AN INSULIN COMPOUND

(71) Applicant: Arecor Limited, Saffron Walden (GB)

(72) Inventors: Jan Jezek, Saffron Walden (GB); David Gerring, Saffron Walden (GB); Sarah Howell, Saffron Walden (GB); Leon Zakrzewski, Saffron Walden (GB)

(73) Assignee: Arecor Limited, Saffron Walden (GB)

( * ) Notice: Subject to any disclaimer, the term of this patent is extended or adjusted under 35 U.S.C. 154(b) by 1044 days.

(21) Appl. No.: 17/044,719

(22) PCT Filed: Apr. 4, 2019

(86) PCT No.: PCT/GB2019/050990
§ 371 (c)(1),
(2) Date: Oct. 1, 2020

(87) PCT Pub. No.: WO2019/193353
PCT Pub. Date: Oct. 10, 2019

(65) Prior Publication Data
US 2021/0038506 A1 Feb. 11, 2021

(30) Foreign Application Priority Data

Apr. 4, 2018 (GB) .................................. 1805537
May 3, 2018 (GB) .................................. 1807319

(51) Int. Cl.
| | | |
|---|---|---|
| *A61K 9/00* | (2006.01) | |
| *A61K 9/08* | (2006.01) | |
| *A61K 33/30* | (2006.01) | |
| *A61K 38/06* | (2006.01) | |
| *A61K 38/28* | (2006.01) | |
| *A61K 47/02* | (2006.01) | |
| *A61K 47/12* | (2006.01) | |
| *A61K 47/26* | (2006.01) | |

(52) U.S. Cl.
CPC ............ *A61K 9/0019* (2013.01); *A61K 33/30* (2013.01); *A61K 38/063* (2013.01); *A61K 38/28* (2013.01); *A61K 47/02* (2013.01); *A61K 47/12* (2013.01); *A61K 47/26* (2013.01); *A61K 9/08* (2013.01)

(58) Field of Classification Search
CPC .... A61K 9/0019; A61K 33/30; A61K 38/063; A61K 38/28; A61K 47/02; A61K 47/12; A61K 47/26; A61K 9/08; A61K 47/183; A61K 2300/00
See application file for complete search history.

(56) References Cited

U.S. PATENT DOCUMENTS

| | | |
|---|---|---|
| 5,866,538 A | 2/1999 | Norup et al. |
| 6,960,561 B2 | 11/2005 | Boderke |
| 7,205,276 B2 | 4/2007 | Boderke |
| 7,279,457 B2 | 10/2007 | Pohl et al. |
| 7,452,860 B2 | 11/2008 | Boderke |
| 7,476,652 B2 | 1/2009 | Brunner-Schwarz et al. |
| 7,696,162 B2 | 4/2010 | Boderke |
| 7,998,927 B2 | 10/2011 | Maggio |
| 8,324,157 B2 | 5/2012 | Olsen et al. |
| 8,318,154 B2 | 11/2012 | Frost et al. |
| 8,772,231 B2 | 7/2014 | Maggio |
| 2005/0214251 A1 | 9/2005 | Pohl et al. |
| 2008/0039365 A1 | 2/2008 | Steiner et al. |
| 2008/0194461 A1 | 8/2008 | Maggio |
| 2008/0268032 A1 | 10/2008 | Maggio |
| 2009/0011976 A1 | 1/2009 | Ludvigsen et al. |
| 2009/0137455 A1 | 5/2009 | Steiner et al. |
| 2010/0210506 A1 | 8/2010 | Quay et al. |
| 2010/0227795 A1 | 9/2010 | Steiner et al. |
| 2012/0178675 A1 | 7/2012 | Pohl et al. |
| 2013/0231281 A1 | 9/2013 | Soula et al. |
| 2013/0302275 A1 | 11/2013 | Wei et al. |
| 2013/0331320 A1 | 12/2013 | Havelund et al. |
| 2014/0024582 A1 | 1/2014 | Yang |
| 2014/0135263 A1 | 5/2014 | Pohl et al. |
| 2014/0142034 A1 | 5/2014 | Soula et al. |
| 2014/0221285 A1 | 8/2014 | Bley et al. |
| 2014/0357554 A1 | 12/2014 | Pohl et al. |
| 2015/0190475 A1 | 7/2015 | Bley et al. |
| 2015/0265683 A1 | 9/2015 | Sahib et al. |

(Continued)

FOREIGN PATENT DOCUMENTS

| | | |
|---|---|---|
| EP | 0214826 A2 | 3/1987 |
| EP | 0375437 A2 | 6/1990 |

(Continued)

OTHER PUBLICATIONS

De la Peña et al. "Pharmacokinetics and Pharmacodynamics of High-Dose Human Regular U-500 Insulin Versus Human Regular U-100 Insulin in Healthy Obese Subjects", Diabetes Care, 2011, 34, pp. 2496-2501.
5.0 European Pharmacopoeia Monograph (Insulin, Human, pp. 1800-1802).
2.9.20. European Pharmacopoeia Monograph (Particulate Contamination: Visible Particles, p. 302).
Lougheed et al., "Physical stability of insulin formulations" Diabetes, American Diabetes Association, 1983, vol. 32, No. 5, pp. 424-432.
Moghaddam et al., "Evaluation of Insulin Stability in the Presence of Nonionic Surface Active Agents (Polysorbate Groups) by Circular Dichroism and Fluorescence Spectroscopy" Asian Journal of Biochemistry, 2015, vol. 10, No. 1, pp. 17-30.

(Continued)

*Primary Examiner* — Robert A Wax
*Assistant Examiner* — Quanglong N Truong
(74) *Attorney, Agent, or Firm* — Nixon & Vanderhye P.C.

(57) ABSTRACT

There is provided inter alia an injection pen system comprising an injector mechanism and a reservoir comprising an aqueous liquid pharmaceutical composition for delivery by means of said injector mechanism to a mammal wherein the composition comprises (i) an insulin compound, (ii) ionic zinc and (iii) an alkyl glycoside as a non-ionic surfactant.

54 Claims, 6 Drawing Sheets

Figure 1:
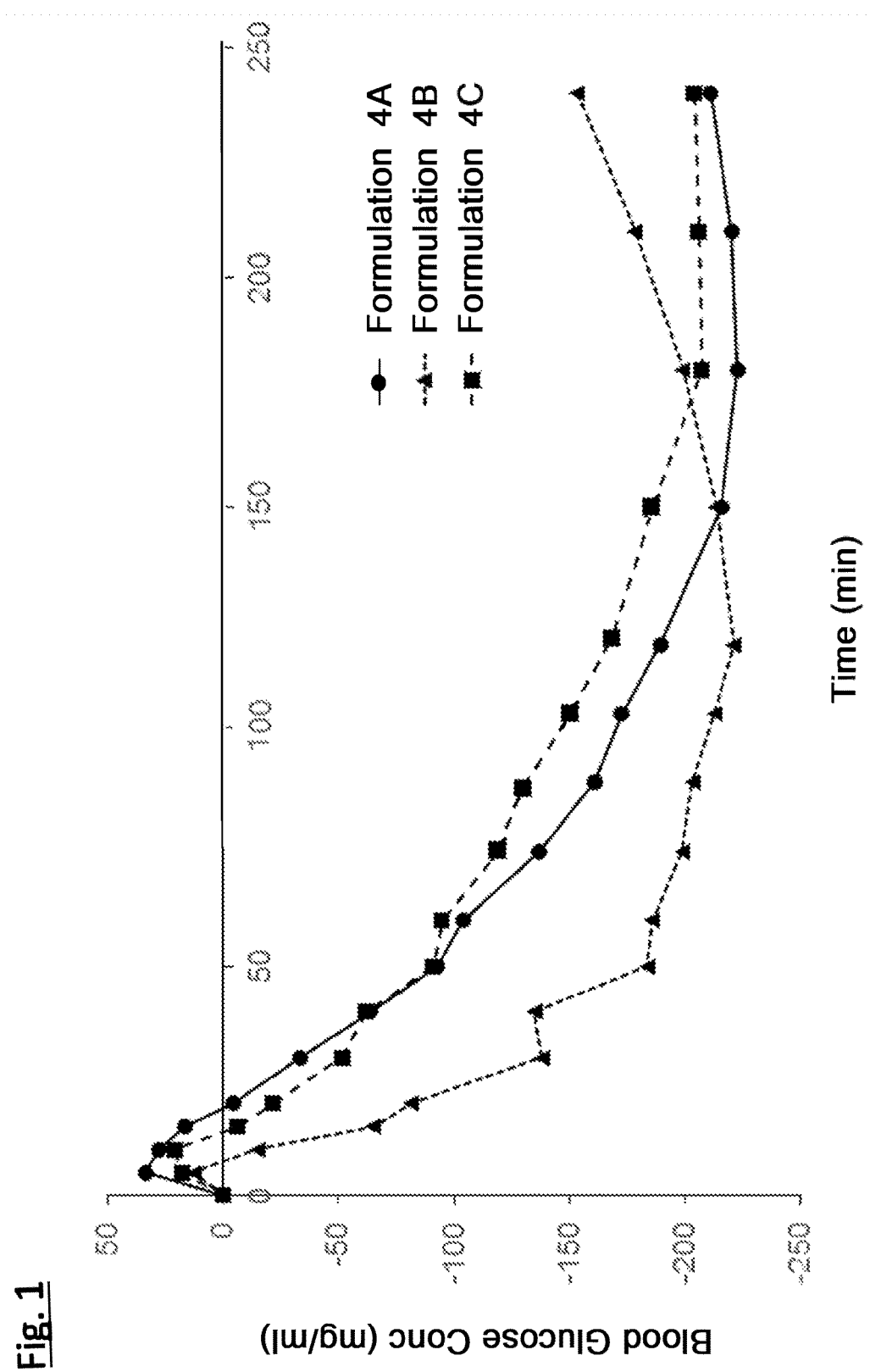

Specification includes a Sequence Listing.

(56) References Cited

U.S. PATENT DOCUMENTS

| | | |
|---|---|---|
| 2015/0273022 A1 | 10/2015 | Wilson et al. |
| 2016/0015814 A1 | 1/2016 | Soula et al. |
| 2016/0082106 A1 | 3/2016 | Soula et al. |
| 2016/0375104 A1* | 12/2016 | Joseph .................. A61K 38/28 601/2 |
| 2017/0056478 A1 | 3/2017 | Akers et al. |
| 2018/0078645 A1 | 3/2018 | Gerring et al. |

FOREIGN PATENT DOCUMENTS

| | | |
|---|---|---|
| EP | 0678522 A1 | 10/1995 |
| EP | 1283051 A1 | 2/2003 |
| EP | 1381385 B1 | 1/2004 |
| EP | 1740154 B1 | 1/2007 |
| EP | 2106790 B1 | 10/2009 |
| EP | 2289539 B1 | 3/2011 |
| EP | 2319500 B1 | 5/2011 |
| EP | 2340033 B1 | 7/2011 |
| WO | WO1991/09617 A1 | 7/1991 |
| WO | WO1996/10417 A1 | 4/1996 |
| WO | WO1997/17945 A2 | 5/1997 |
| WO | WO1999/34821 A1 | 7/1999 |
| WO | WO2002/076495 A1 | 10/2002 |
| WO | WO2005/089722 A1 | 9/2005 |
| WO | WO2007/041481 A1 | 4/2007 |
| WO | WO2007/121256 A2 | 10/2007 |
| WO | WO2007/149096 A1 | 12/2007 |
| WO | WO2008/084237 A2 | 7/2008 |
| WO | WO2010/102020 A1 | 9/2010 |
| WO | WO2010/115819 A1 | 10/2010 |
| WO | WO2010/149772 A1 | 12/2010 |
| WO | WO2011/094632 A1 | 8/2011 |
| WO | WO2012/006283 A1 | 1/2012 |
| WO | WO2013/021143 A1 | 2/2013 |
| WO | WO2013/158618 A1 | 10/2013 |
| WO | WO2013/186138 A1 | 12/2013 |
| WO | WO2014/096985 A2 | 6/2014 |
| WO | WO2015/059302 A1 | 4/2015 |
| WO | WO2015/114374 A1 | 8/2015 |
| WO | WO2015/120457 A1 | 8/2015 |
| WO | WO2015/171484 A1 | 11/2015 |
| WO | WO2016/100042 A1 | 6/2016 |
| WO | WO2017/191464 A1 | 11/2017 |
| WO | WO2018/060735 A1 | 4/2018 |
| WO | WO2018/060736 A1 | 4/2018 |
| WO | WO2018/203059 A1 | 11/2018 |
| WO | WO2018/203060 A2 | 11/2018 |
| WO | WO2018/203061 A1 | 11/2018 |
| WO | WO2019/193349 A1 | 10/2019 |
| WO | WO2019/193351 A1 | 10/2019 |
| WO | WO2019/193353 A1 | 10/2019 |

OTHER PUBLICATIONS

Cooper, "Therapeutic potential of copper chelation with triethylenetetramine in managing diabetes mellitus and Alzheimer's disease" Medline, US National Library of Medicine, XP002774649.

Pohl et al. "Ultra-Rapid Absorption of Recombinant Human Insulin Induced by Zinc Chelation and Surface Charge Masking", Journal of Diabetes Science and Technology, 2012, vol. 6, No. 4, pp. 755-763.

Steiner S et al. "A novel insulin formulation with a more rapid onset of action" Diabetologia; Clinical & Experimental Diabetes & Metabolism, 2008, vol. 51, No. 9, pp. 1602-1606.

Pillai et al. "Transdermal iontophoresis of insulin II. Physicochemical considerations" International Journal of Pharmaceutics, 2003, vol. 254, pp. 271-280.

Liu et al. "Insulin Aggregation in Aqueous Media and Its Effect on Alpha-Chymotrypsin-Mediated Proteolytic Degradation" Pharmaceutical Research, 1991, vol. 8, No. 7, pp. 925-929.

Prabhu et al. "A study of factors controlling dissolution kinetics of zinc complexed protein suspensions in various ionic species" International Journal of Pharmaceutics 2001, vol. 217, pp. 71-78.

Arnebrant et al. "Adsorption of Insulin on Metal Surfaces in Relation to Association Behavior" Journal of Colloid and Interface Science, 1988, vol. 122, No. 2, pp. 557-566.

Okada et al. "Vaginal Absorption of a Potent Luteinizing Hormone-Releasing Hormone Analogue (Leuprolide) in Rats 11: Mechanism of Absorption Enhancement with Organic Acids" Journal of Pharmaceutical Sciences, 1983, vol. 72, No. 1, pp. 75-78.

U.S. Appl. No. 17/044,706, filed Oct. 1, 2020, Jezek et al.
U.S. Appl. No. 17/044,729, filed Oct. 1, 2020, Jezek et al.

* cited by examiner

INJECTION PEN SYSTEM FOR THE DELIVERY OF AN INSULIN COMPOUND

CROSS-REFERENCE TO RELATED APPLICATIONS

This application is the U.S. national phase of International Application No. PCT/GB2019/050990 filed Apr. 4, 2019 which designated the U.S. and claims priority to GB 1805537.6 filed Apr. 4, 2018 and GB 1807319.7 filed May 3, 2018, the entire contents of each of which are hereby incorporated by reference.

REFERENCE TO SEQUENCE LISTING SUBMITTED ELECTRONICALLY

The content of the electronically submitted sequence listing (Name: 6662-1310_SEQ_LISTING.txt; Size: 1,948 bytes; and Date of Creation: Oct. 1, 2020) filed with the application is incorporated herein by reference in its entirety.

FIELD OF THE INVENTION

This invention relates inter alia to an injection pen system for the delivery of an insulin compound, particularly rapid acting aqueous liquid pharmaceutical compositions of insulin and insulin analogues. Such a system is suitable for the treatment of subjects suffering from diabetes mellitus, especially Type 1 diabetes mellitus.

BACKGROUND OF THE INVENTION

Diabetes mellitus ("diabetes") is a metabolic disorder associated with poor control of blood sugar levels leading to hypo or hyperglycaemia. Untreated diabetes can lead to serious microvascular and macrovascular complications including coronary artery disease, peripheral artery disease, stroke, diabetic nephropathy, neuropathy and retinopathy. The two main types of diabetes are (i) Type 1 diabetes resulting from the pancreas not producing insulin for which the usual treatment is insulin replacement therapy and (ii) Type 2 diabetes where patients either produce insufficient insulin or have insulin resistance and for which treatments include insulin sensitising agents (such as metformin or pioglitazone), traditional insulin secretagogues (such as sulfonylureas), SGLT2 inhibitors (such as dapagliflozin, canagliflozin and empagliflozin) which reduce glucose absorption in the kidneys and so promote glucose excretion, GLP-1 agonists (such as exenatide and dulaglutide) which stimulate insulin release from pancreatic beta cells and DPPIV inhibitors (such as sitagliptin or vildagliptin) which inhibit breakdown of GLP-1 leading to increased insulin secretion. Patients with Type 2 diabetes may eventually require insulin replacement therapy.

For patients requiring insulin replacement therapy, a range of therapeutic options are possible. The use of recombinant human insulin has in recent times been overtaken by use of insulin analogues which have modified properties, for example, are longer acting or faster acting than normal insulin. Thus, a common regimen for a patient involves receiving a long acting basal insulin supplemented by a rapid acting insulin around mealtimes.

Insulin is a peptide hormone formed of two chains (A chain and B chain, respectively 21 and 30 amino acids in length) linked via disulfide bridges. Insulin normally exists at neutral pH in the form of a hexamer, each hexamer comprising three dimers bound together by zinc ions. Histidine residues on the insulin are known to be involved in the interaction with the zinc ions. Insulin is stored in the body in the hexameric form but the monomer form is the active form. Traditionally, therapeutic compositions of insulin have also been formulated in hexameric form in the presence of zinc ions. Typically, there are approximately three zinc cations per one insulin hexamer. It has been appreciated that the hexameric form is absorbed from the injection site considerably more slowly than the monomeric and dimeric forms. Therefore, a faster onset of insulin action can be achieved if the hexameric form is destabilised allowing a more rapid dissociation of the zinc-bound hexamer into dimers and monomers in the subcutaneous space following injection. Three insulin analogues have been genetically engineered with this principle in mind. A first is insulin ispro (HUMALOG®) in which residues 28 and 29 of the B chain (Pro and Lys respectively) are reversed, a second is insulin aspart (NOVORAPID®) in which residue 28 of the B chain, normally Pro, is replaced by Asp, and a third is insulin glulisine (APIDRA®) in which residue 3 of the B chain, normally Asn is replaced by Lys and residue 29 of the B chain, normally Lys, is replaced by Glu.

Whilst the existing rapid acting insulin analogues can achieve a more rapid onset of action, it has been appreciated that even more rapid acting ("ultra rapid acting") insulins can be achieved by removing the zinc cations from insulin altogether. Unfortunately, the consequence of the hexamer dissociation is typically a considerable impairment in insulin stability both with respect to physical stability (e.g. stability to aggregation) and chemical stability (e.g. stability to deamidation). For example, monomeric insulin or insulin analogues having a rapid onset of action are known to aggregate and become physically unstable very rapidly because the formation of insoluble aggregates proceeds via monomers of insulin. Various approaches to addressing this problem have been described in the art:

U.S. Pat. No. 5,866,538 (Norup) describes insulin preparations of superior chemical stability comprising human insulin or an analogue or derivative thereof, glycerol and/or mannitol and 5 mM to 100 mM of a halogenide (e.g. NaCl).

U.S. Pat. No. 7,205,276 (Boderke) addresses the stability problems associated with preparing zinc-free formulations of insulin and insulin derivatives and analogues and describes an aqueous liquid formulation comprising at least one insulin derivative, at least one surfactant, optionally at least one preservative and optionally at least one of an isotonicizing agent, a buffer and an excipient, wherein the formulation is stable and free from or contains less than 0.4% (e.g. less than 0.2%) by weight of zinc based on the insulin content of the formulation. The preferred surfactant appears to be polysorbate 20 (polyoxyethylene (20) sorbitan monolaurate).

US2008/0194461 (Maggio) describes formulations of peptides and polypeptides including insulin which contain an alkyl glycoside, which component is said to reduce aggregation and immunogenicity.

WO2012/006283 (Pohl) describes formulations containing insulin together with a zinc chelator such as ethylene-diaminetetraacetate (EDTA). Modulating the type and quantity of EDTA is said to change the insulin absorption profile. Calcium EDTA is the preferred form of EDTA since it is said to be associated with reduced pain at the injection site and is less likely to remove calcium from the body. Preferred formulations also contain citrate which is said to further enhance absorption and to improve the chemical stability of the formulation.

US2010/0227795 (Steiner) describes a composition comprising insulin, a dissociating agent such as citric acid or sodium citrate, and a zinc chelator such as EDTA wherein the formulation has a physiological pH and is a clear aqueous solution. The formulations are said to have improved stability and rapid onset of action.

WO2015/120457 (Wilson) describes stabilized ultra-rapid acting insulin formulations comprising insulin in combination with a zinc chelator such as EDTA, a dissolution/stabilization agent such as citric acid, a magnesium salt, a zinc compound and optionally additional excipients.

Further approaches to accelerating the absorption and effect of insulin through the use of specific accelerating additives have been described:

WO91/09617 (Jørgensen) reports that nicotinamide or nicotinic acid or a salt thereof increases the speed of absorption of insulin from aqueous preparations administered parenterally.

WO2010/149772 (Olsen) describes a formulation comprising insulin, a nicotinic compound and arginine. The presence of arginine is said to improve the chemical stability of the formulation.

WO2015/171484 (Christe) describes rapid-acting formulations of insulin wherein onset of action and/or absorption of insulin is faster due to the presence of treprostinil.

US2013/0231281 (Soula) describes an aqueous solution composition comprising insulin or an insulin analogue and at least one oligosaccharide whose average degree of polymerisation is between 3 and 13 and whose polydispersity index is above 1.0, said oligosaccharide having partially substituted carboxyl functional groups, the unsubstituted carboxyl functional groups being salifiable. Such a formulation is said to be rapid acting.

WO2017/191464 (Arecor Limited) describes an aqueous liquid pharmaceutical formulation comprising insulin or an insulin analogue, ionic zinc, a chelating agent and polysorbate 80.

WO2016/100042 (Eli Lilly and Company) describes a composition of human insulin or insulin analogue that includes specific concentrations of citrate, chloride, in some cases including the addition of sodium chloride, zinc and, optionally magnesium chloride and/or surfactant, said to have faster pharmacokinetic and/or pharmacodynamic action than commercial formulations of existing insulin analogue products.

Commercially available rapid-acting insulin formulations are available as 100 U/ml formulations (HUMALOG® (insulin lispro), NOVORAPID® (also known as NOVOLOG®, insulin aspart) and APIDRA® (insulin glulisine)) and 200 U/ml formulations (HUMALOG®).

There are a number of devices that can be used to deliver insulin, including syringes, insulin pumps and insulin pens.

Syringes can typically be used to deliver basal (long-acting) insulins, typically as one injection per day. Whilst syringes are still used, they are gradually being replaced by more convenient insulin pens.

Insulin pens are a very convenient way of delivering both basal and prandial insulin. Insulin pens contain a cartridge that is filled with insulin and an apparatus for dispensing a required amount of insulin, as needed by the user. The required amount is first selected (this often referred to as being "dialed") using a specifically designed mechanism and then dispensed via a very small retractable needle whilst holding the pen against the body (typically the abdomen).

It would be desirable if an injection pen system were available which can deliver compositions of insulin or insulin analogues from a reservoir, which are rapid or ultra-rapid acting, and which remain stable upon storage and in-use. It would be particularly desirable, particularly for diabetic patients that require large doses of insulin, if an injection pen system were available which can deliver high strength compositions of insulin or insulin analogues that are rapid or ultra-rapid acting, and which remain stable upon storage and in-use.

SUMMARY OF THE INVENTION

According to the invention there is provided an injection pen system comprising an injector mechanism and a reservoir comprising an aqueous liquid pharmaceutical composition for delivery by means of said injector mechanism to a mammal wherein the composition comprises (i) an insulin compound, (ii) ionic zinc and (iii) an alkyl glycoside as a non-ionic surfactant. The compositions of the system of the invention provide insulin in a form with good physical and chemical stability, preferably in a form which is rapid or ultra-rapid acting. The present inventors have importantly identified that use of an alkyl glycoside as a non-ionic surfactant increases the storage stability of insulin compositions, which is expected to permit the use of an injection pen based system to deliver aqueous liquid pharmaceutical compositions of insulin to the body of a mammal from one or more reservoirs with good in-use stability.

As noted in the background discussion above, use of EDTA to chelate zinc ions in hexameric insulin does increase the rapidity of action but at the cost of greatly reduced stability. Without being limited by theory, the present inventors have also appreciated that the use in certain embodiments of the invention of zinc together with species which bind zinc less strongly can achieve similar effects in terms of speed of action and their moderately destabilising effects can be reduced or eliminated by using a non-ionic surfactant. The present inventors have further appreciated that the presence of such a zinc binding species accelerates the onset of action of a high concentration (high strength) insulin compound composition thereby mitigating the delaying effect on insulin onset of action which has been observed when the concentration of insulin compound in a composition is increased.

Compositions of the system of the invention may be used in the treatment of subjects suffering from diabetes mellitus, particularly Type 1 diabetes mellitus especially for administration at meal times.

As can be seen from the accompanying examples, example compositions of the system of the invention are significantly more stable than compositions without alkyl glycoside as non-ionic surfactant including under stress conditions that model those of an injection pen system. The example compositions achieve a rapid speed of action of insulin and are more stable than prior art rapid acting insulin formulations containing EDTA. Furthermore, example compositions of the system of the invention contain high concentrations of insulin compound while maintaining a rapid onset of action.

DESCRIPTION OF THE SEQUENCE LISTING

SEQ ID NO: 1: A chain of human insulin
SEQ ID NO: 2: B chain of human insulin
SEQ ID NO: 3: B chain of insulin lispro
SEQ ID NO: 4: B chain of insulin aspart
SEQ ID NO: 5: B chain of insulin glulisine

FIGURES

FIG. 1. Pharmacodynamic profiles of Formulations 4A-4C of Example 4 in a validated diabetic Yucatan miniature pig model.

Figure 2:
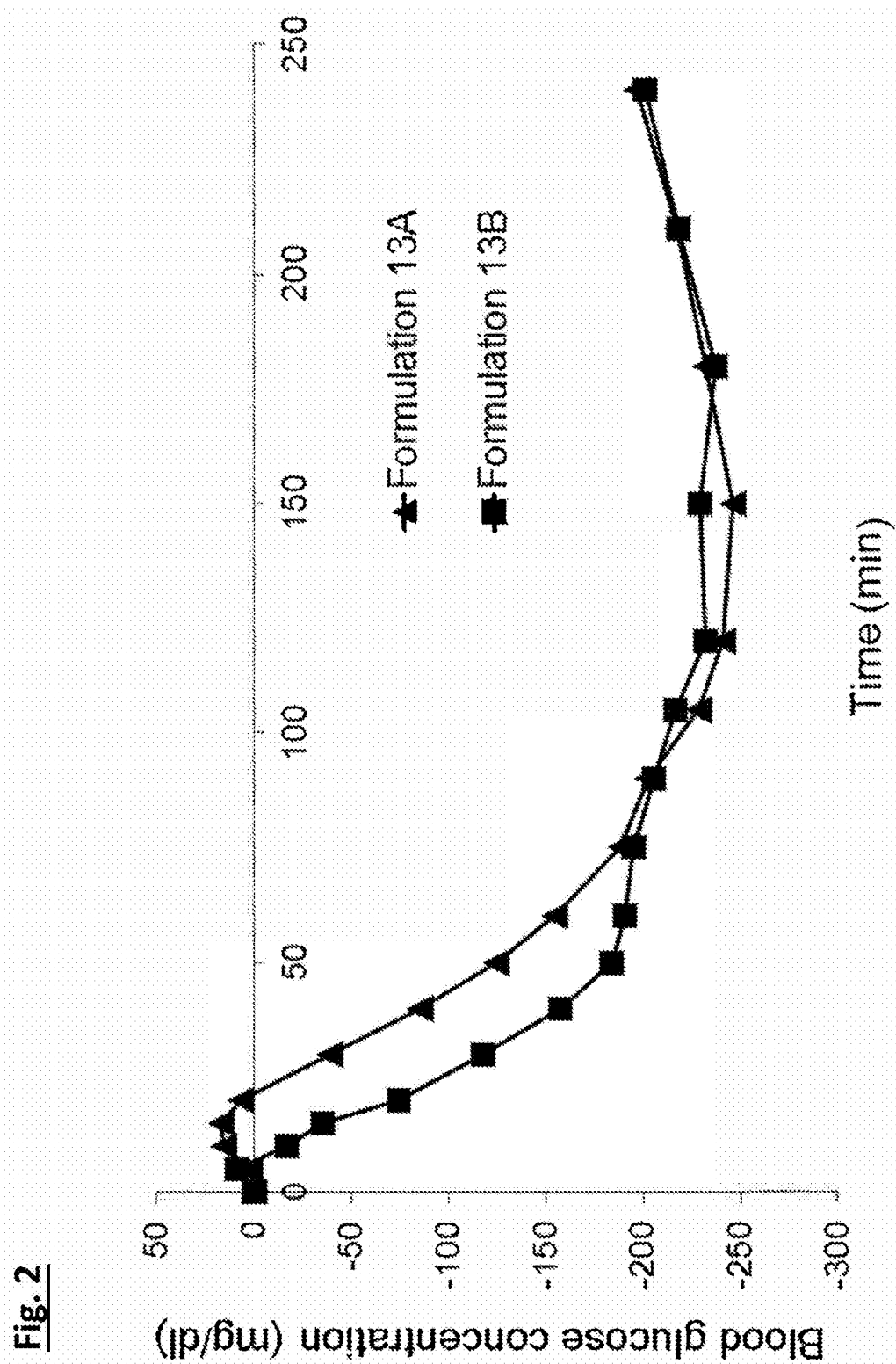

FIG. 2. Pharmacodynamic profile of Formulations 13A and 13B of Example 13 in a validated diabetic Yucatan miniature pig model.

Figure 3:
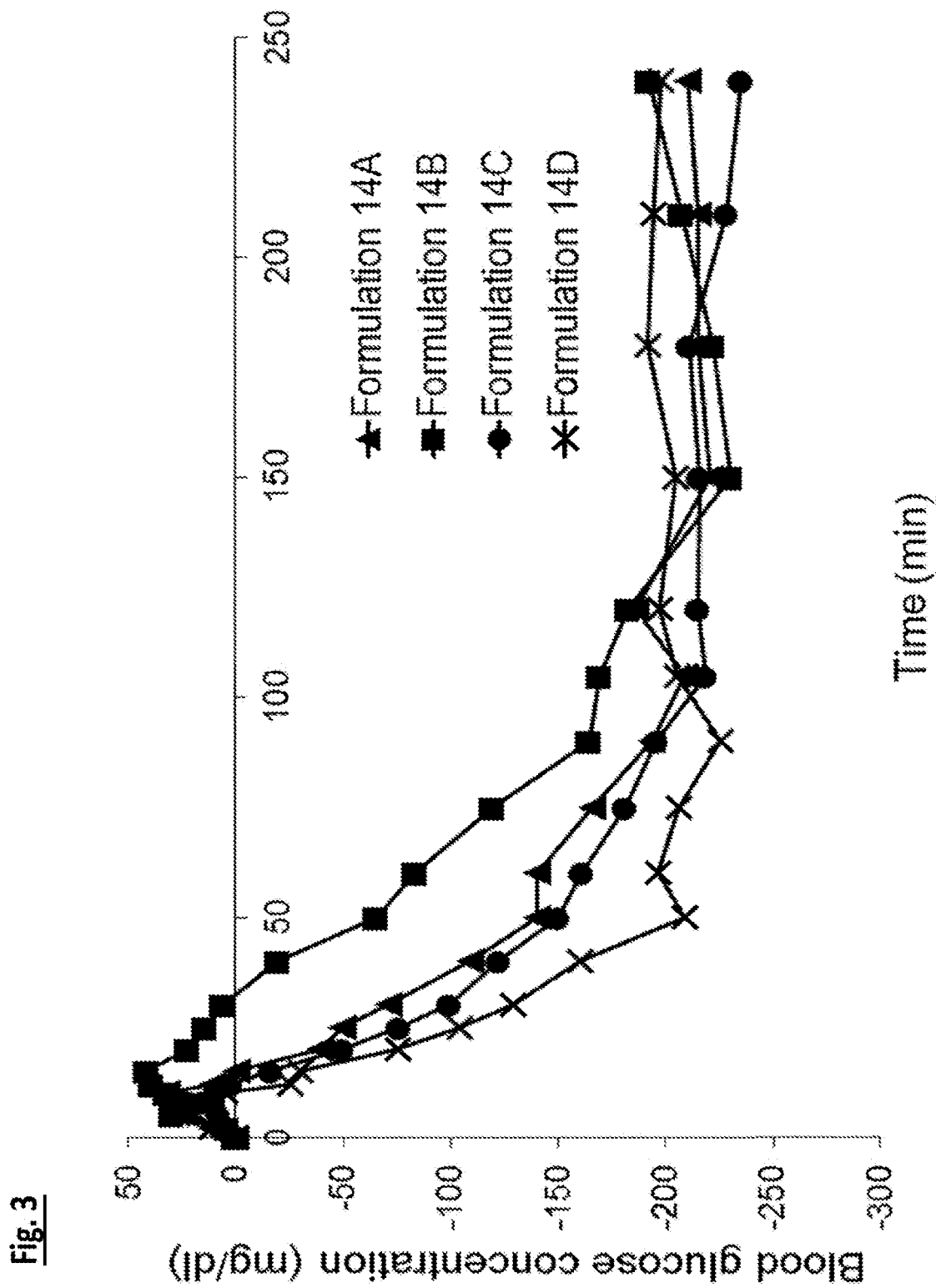

FIG. 3. Pharmacodynamic profiles of formulations 14A-14D of Example 14 in a validated diabetic Yucatan miniature pig model.

Figure 4:
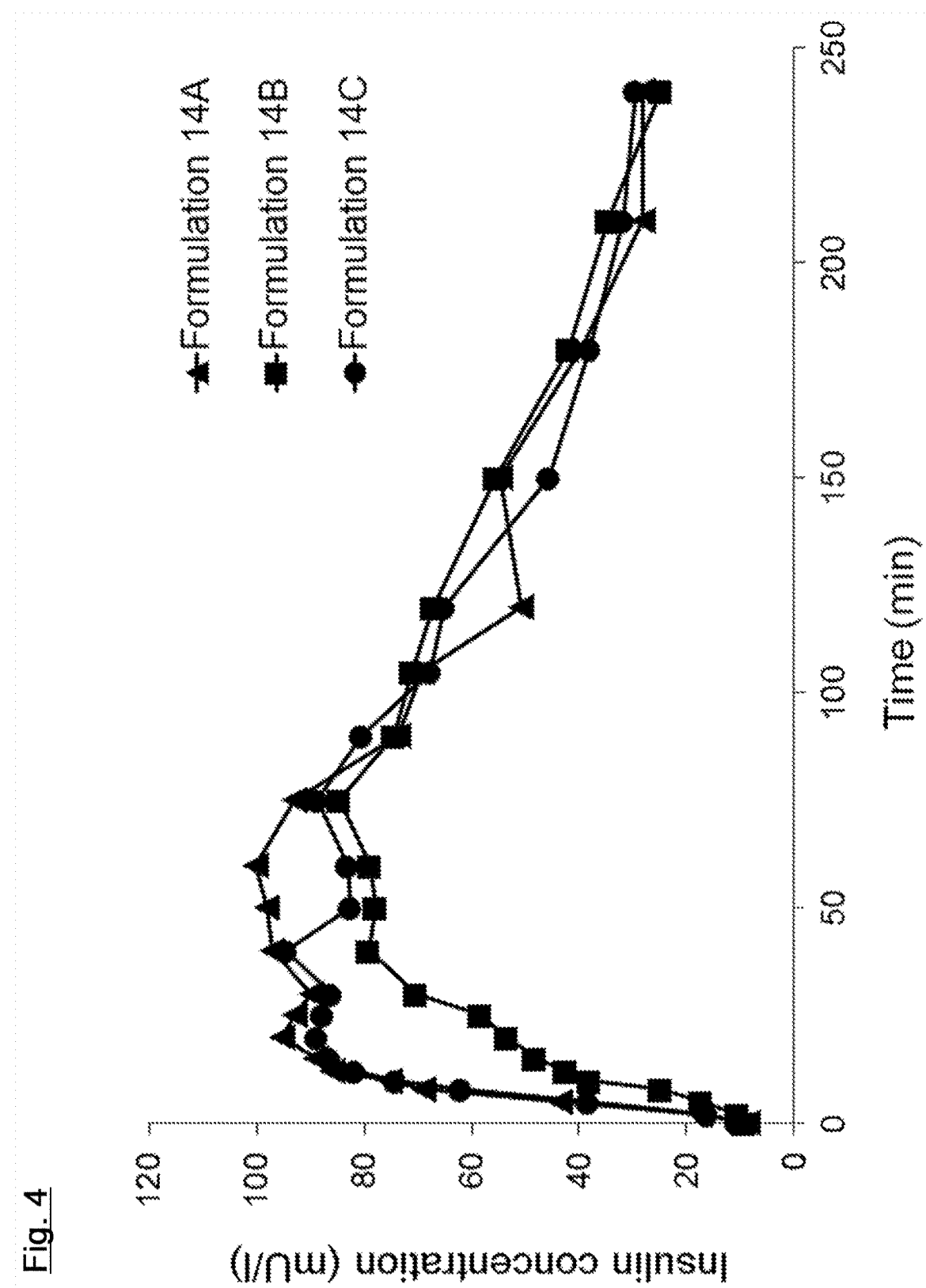

FIG. 4. Pharmacokinetic profiles of formulations 14A-14C of Example 14 in a validated diabetic Yucatan miniature pig model.

Figure 5:
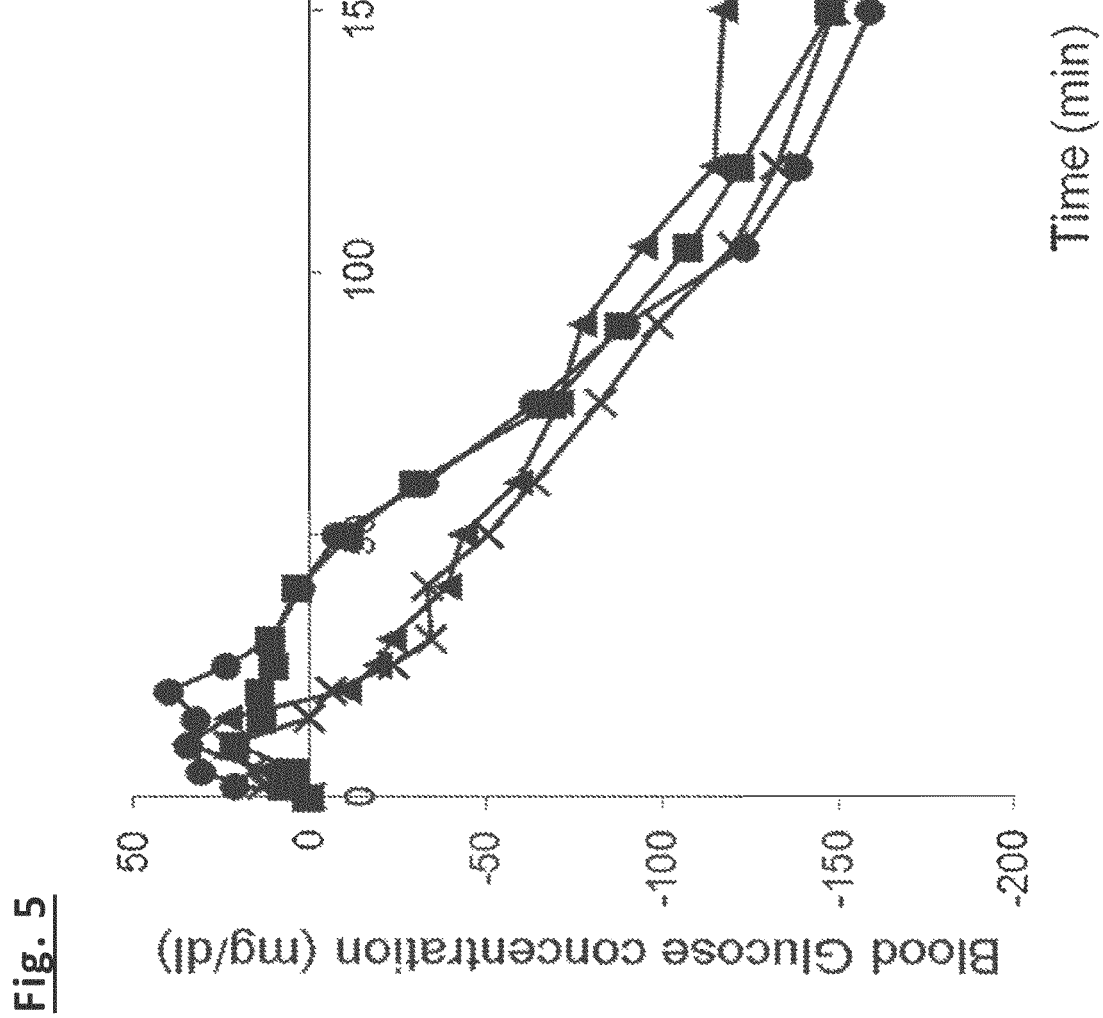

FIG. 5. Pharmacodynamic profiles of formulations 15A-15D of Example 15 in a validated diabetic Yucatan miniature pig model.

Figure 6:
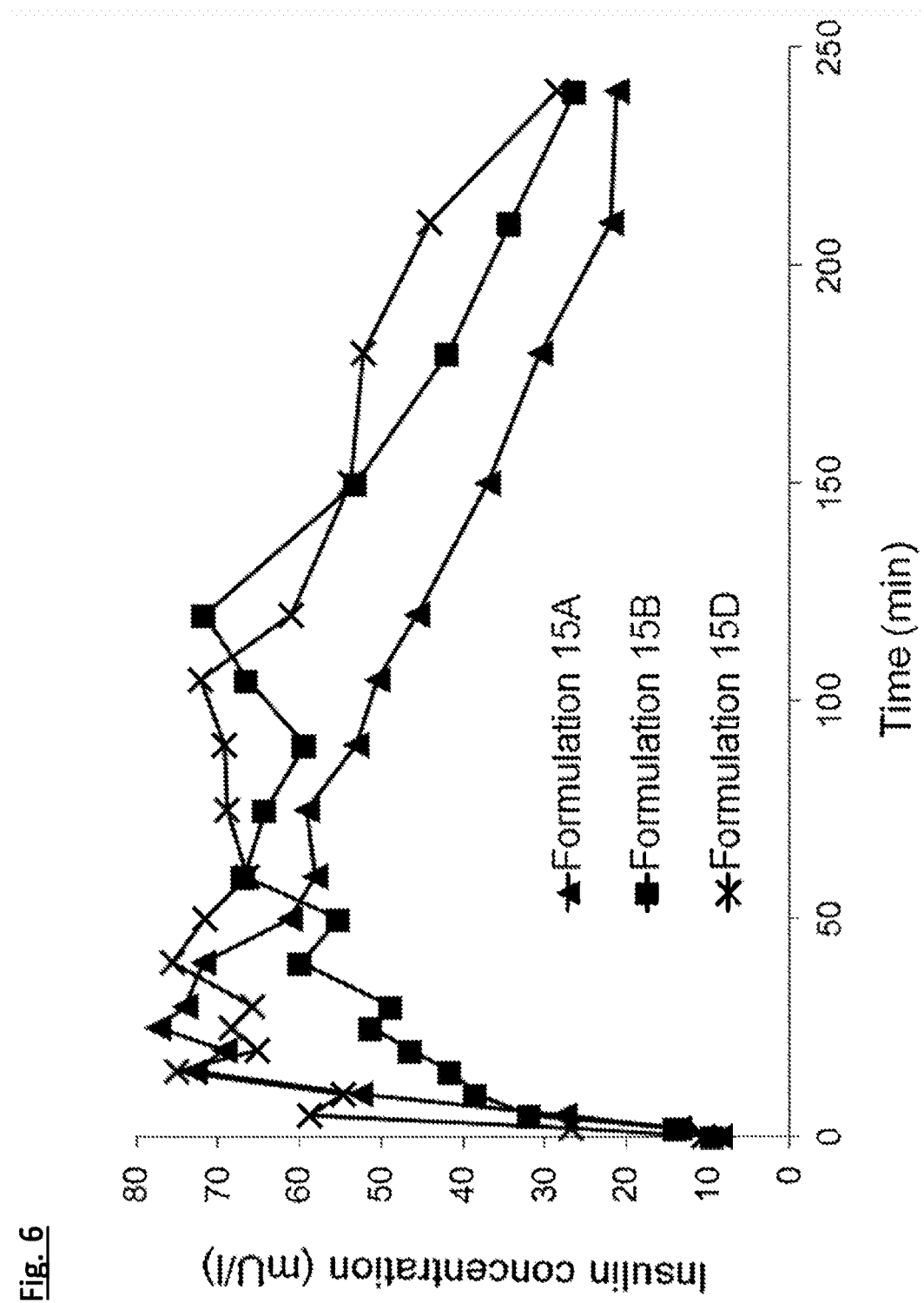

FIG. 6. Pharmacokinetic profiles of formulations 15A, 15B and 15D of Example 15 in a validated diabetic Yucatan miniature pig model.

DETAILED DESCRIPTION OF THE INVENTION

As used herein, "insulin compound" refers to insulin and insulin analogues.

As used herein, "insulin" refers to native human insulin having an A chain and a B chain as set out in SEQ ID NOS: 1 and 2 and containing and connected by disulfide bridges as in the native molecule (Cys A6-Cys A11, Cys B7 to Cys A7 and Cys-B19-Cys A20). Insulin is suitably recombinant insulin.

"Insulin analogue" refers to an analogue of insulin which is an insulin receptor agonist and has a modified amino acid sequence, such as containing 1 or 2 amino acid changes in the sequence of the A or B chain (especially the B chain). Desirably such amino acid modifications are intended to reduce affinity of the molecule for zinc and thus increase speed of action. Thus, desirably an insulin analogue has a speed of action which is the same as or preferably greater than that of insulin. The speed of action of insulin or an insulin analogue may be determined in the Diabetic Pig Pharmacokinetic/Pharmacodynamic Model (see Examples, General Methods (c)). Exemplary insulin analogues include faster acting analogues such as insulin lispro, insulin aspart and insulin glulisine. These forms of insulin have the human insulin A chain but variant B chains—see SEQ ID NOS: 3-5. Further faster acting analogues are described in EP0214826, EP0375437 and EP0678522 the contents of which are herein incorporated by reference in their entirety. Suitably, the insulin compound is not insulin glargine. Suitably, the insulin compound is not insulin degludec. Suitably, the insulin compound is a rapid-acting insulin compound, wherein "rapid-acting" is defined as an insulin compound which has a speed of action which is greater than that of native human insulin, e.g. as measured using the Diabetic Pig Pharmacokinetic/Pharmacodynamic Model (see Examples, General Methods (c)).

In one embodiment, the insulin compound is recombinant human insulin. In another embodiment, it is insulin lispro. In another embodiment, it is insulin aspart. In another embodiment, it is insulin glulisine. In another embodiment, the insulin compound is not recombinant human insulin.

The term "aqueous liquid pharmaceutical composition", as used herein, refers to a composition suitable for therapeutic use in which the aqueous component is or comprises water, preferably distilled water, deionized water, water for injection, sterile water for injection or bacteriostatic water for injection. The aqueous liquid pharmaceutical compositions of the system of the invention are solution compositions in which all components are dissolved in water.

The concentration of insulin compound in the composition is in the range 10-1000 U/ml e.g. 50-1000 U/ml, e.g. 400-1000 U/ml, e.g. 500-1000 U/ml, e.g. 600-1000 U/ml, e.g. 700-1000 U/ml, e.g. 800-1000 U/ml, e.g. 900-1000 U/ml, e.g. 1000U/ml. In one embodiment, the concentration of insulin compound in the composition is 10-250 U/ml.

"U/ml" as used herein describes the concentration of insulin compound in terms of a unit per volume, wherein "U" is the international unit of insulin activity (see e.g. European Pharmacopoeia 5.0, Human Insulin, pp 1800-1802).

The compositions of the system of the invention contain ionic zinc i.e. $Zn^{2+}$ ions. The source of the ionic zinc will typically be a water-soluble zinc salt such as $ZnCl_2$, $ZnO$, $ZnSO_4$, $Zn(NO_3)_2$ or $Zn(acetate)_2$ and most suitably $ZnCl_2$ or $ZnO$.

The ionic zinc in the composition is typically present at a concentration of more than 0.05% e.g. more than 0.1% e.g. more than 0.2%, more than 0.3% or more than 0.4% by weight of zinc based on the weight of insulin compound in the composition. Thus, the concentration of the ionic zinc in the composition may be more than 0.5% by weight of zinc based on the weight of insulin compound in the composition, for example 0.5-1%, e.g. 0.5-0.75%, e.g. 0.5-0.6% by weight of zinc based on the weight of insulin compound in the composition. For the purpose of the calculation the weight of the counter ion to zinc is excluded.

In a composition e.g. containing 1000 U/ml of insulin compound the concentration of the ionic zinc will typically be more than 0.15 mM e.g. more than 0.3 Mm, e.g. more than 0.6 mM, more than 0.9 mM or more than 1.2 mM. Thus, the concentration of the ionic zinc in the composition may be more than 1.5 mM, for example 1.5-6.0 mM, e.g. 2.0-4.5 mM, e.g. 2.5-3.5 mM.

The compositions of the system of the invention may optionally comprise a zinc binding species e.g. at a concentration of 1 mM or more and, for example, selected from species having a log K with respect to zinc ion binding in the range 4.5-12.3 at 25° C. Suitably, the zinc binding species is selected from species having a log K with respect to zinc ion binding in the range 4.5-10 at 25° C. Metal binding stability constants listed in the National Institute of Standards and Technology reference database 46 (Critically Selected Stability Constants of Metal Complexes) can be used. The database typically lists log K constants determined at 25° C. Therefore, the suitability of a zinc binding species for the present invention can be determined based on its log K metal binding stability constant with respect to zinc binding, as measured at 25° C. and as quoted by the database. The zinc binding species may also be described as an "accelerator" in the compositions according to the invention. Exemplary zinc binding species include polydendate organic anions. Thus, in a preferred embodiment, the zinc binding species is citrate (log K=4.93) which can, for example, be employed as trisodium citrate or citric acid. Further examples include pyrophosphate (log K=8.71), aspartate (log K=5.87), glutamate (log K=4.62), cysteine (log K=9.11), cystine (log K=6.67) and glutathione (log K=7.98). Other possible zinc binding species include substances that can contribute a lone pair of electrons or electron density for interaction with ionic zinc such as polydendate amines including ethylenediamine (log K=5.69), diethylenetriamine (DETA, log K=8.88) and triethylenetetramine (TETA, log K=11.95); and aromatic or heteroaromatic substances that can contribute a lone pair of electrons especially those comprising an imidazole moiety such as histidine (log K=6.51). Thus, in one embodiment, the zinc binding species having a log K with respect to zinc ion binding in the range 4.5-12.3 is selected from citrate, pyrophosphate, aspartate, glutamate, cysteine, cystine, glutathione, ethylenediamine, histidine, DETA and TETA.

The most suitable concentration of the zinc binding species will depend on the agent and its log K value and will typically be in the range 1-100 mM. The concentration of zinc binding species can be adjusted according to the particular concentration of insulin compound present in the composition, in order to provide the desired accelerating effect.

For example, the zinc binding species having a log K with respect to zinc ion binding in the range 4.5-12.3 may be present at a concentration of 1-60 mM. Suitably the concentration of the zinc binding species in the composition is 5-60 mM e.g. 5-60 mM, e.g. 10-60 mM, e.g. 20-60 mM, e.g. 30-60 mM, e.g. 40-60 mM, e.g. 40-50 mM, more preferably around 44 mM when the zinc binding species is citrate or histidine for insulin compound 1000 U/ml compositions.

Anionic zinc binding species may be employed as the free acid or a salt form, such as a salt form with sodium or calcium ions, especially sodium ions.

A mixture of zinc binding species may be employed, although a single zinc binding species is preferred.

Suitably the molar ratio of ionic zinc to zinc binding species in the composition is 1:3 to 1:175.

The following ranges are particularly of interest especially for citrate or histidine as zinc binding species: e.g. 1:10-1:175, e.g. 1:10 to 1:100, e.g. 1:10-1:50, e.g. 1:10 to 1:30, e.g. 1:10 to 1:20 (especially for insulin compound 1000 U/ml composition).

For example, a composition containing 1000 U/ml of insulin compound may contain around 3 mM of ionic zinc (i.e. around 197 μg/ml of ionic zinc, i.e. around 0.54% by weight of zinc based on the weight of insulin compound in the composition) and around 30-60 mM e.g. 40-60 mM e.g. 40-50 mM zinc binding species (especially citrate).

In one embodiment, the ratio of insulin compound concentration (U/ml) to zinc binding species (mM) in the composition is in the range 100:1 to 2:1 e.g. 50:1 to 2:1, e.g. 40:1 to 2:1.

In one embodiment, the composition is substantially free of EDTA and any other zinc binding species having a log K with respect to zinc binding of more than 12.3 as determined at 25° C. In an embodiment, the formulations of the invention are substantially free of EDTA (log K=14.5). Further examples of zinc binding species which have a log K metal binding stability constant with respect to zinc binding of more than 12.3 to be avoided include EGTA (log K=12.6). In general, the composition of the system of the invention will be substantially free of tetradentate ligands or ligands of higher denticity. In an embodiment, the composition of the system of the invention is substantially free of zinc binding species having a log K with respect to zinc ion binding of 10-12.3 at 25° C. "Substantially free" means that the concentration of zinc binding species which have a log K metal binding stability constant with respect to zinc binding as specified (such as EDTA) is less than 0.1 mM, such as less than 0.05 mM, such as less than 0.04 mM or less than 0.01 mM.

Where present, zinc ion binding species which have acid forms (e.g. citric acid) may be introduced into the aqueous compositions of the system of the invention in the form of a salt of the acid, such as a sodium salt (e.g. trisodium citrate). Alternatively, they can be introduced in the form of the acid with subsequent adjustment of pH to the required level. The present inventors have found that in some circumstances introducing the acid form (such as citric acid) into the composition instead of the salt form (e.g. trisodium citrate) may have advantages in terms of providing superior chemical and physical stability. Thus, in an embodiment, the source of the citrate as zinc ion binding species is citric acid.

In an embodiment, the composition comprises (i) an insulin compound (e.g. an insulin compound other than insulin glargine), (ii) ionic zinc, (iii) a zinc binding species selected from diethylenetriamine (DETA) and triethylenetetramine (TETA), and (iv) an alkyl glycoside as non-ionic surfactant. Such a composition may, for example. be substantially free of ethylenediaminetetraacetate (EDTA) and any other zinc binding species having a log K with respect to zinc ion binding of more than 12.3 at 25° C. The zinc binding species may, for example, be present at a concentration of about 0.05 mM or more e.g. 0.05-5 mM e.g. 0.05-2 mM. The molar ratio of ionic zinc to the zinc binding species in the composition may, for example, be 2:1 to 1:10.

In an embodiment, the composition comprises (i) an insulin compound, (ii) ionic zinc, (iii) a zinc binding species at a concentration of 1 mM or more selected from species having a log K with respect to zinc ion binding in the range 4.5-10 at 25° C., (iv) a zinc binding species selected from species having a log K with respect to zinc ion binding of more than 12.3 at 25° C. at a concentration of less than about 0.3 mM, and (v) an alkyl glycoside as non-ionic surfactant. In an embodiment, the zinc binding species having a log K with respect to zinc ion binding of more than 12.3 at 25° C. is present in the composition at a concentration of between about 0.01 mM and about 0.3 mM. In an embodiment, the zinc binding species having a log K with respect to zinc ion binding of more than 12.3 at 25° C. is selected from ethylenediaminetetraacetate (EDTA), ethyleneglycoltetraacetate (EGTA), tetraethylenepentamine, N-(2-hydroxyethyl) ethylenedinitrilotriacetate (HEDTA), 1-methyl-ethylenedinitrilotriacetate (PDTA), 1-ethyl-ethylenedinitrilotriacetate, 1-propyl-thylenedinitrilotriacetate, 1-carboxyethylene-ethylenedinitrilotriacetate, triethylenetetranitrilohexaacetate, tetraethylenepentanitriloheptaacetate (TPHA) and tris(2-aminoethyl)amine (Tren), and especially is EDTA. For example, the molar ratio of ionic zinc to EDTA as zinc binding species having a log K with respect to zinc ion binding of more than 12.3 at 25° C. is 2:1 to 25:1. In an embodiment, the zinc binding species having a log K with respect to zinc ion binding in the range 4.5-10 at 25° C. is selected from citrate, pyrophosphate, aspartate, glutamate, cysteine, cystine, glutathione, ethylenediamine and histidine and especially is citrate. In an embodiment, the zinc binding species having a log K with respect to zinc ion binding in the range 4.5-10 at 25° C. is present at a concentration of 1-50 mM. In an embodiment, the molar ratio of ionic zinc to zinc binding species having a log K with respect to zinc ion binding in the range 4.5-10 at 25° C. is 1:3 to 1:500.

The compositions of the system of the invention contain an alkyl glycoside as a non-ionic surfactant. In one embodiment, the alkyl glycoside is selected from the group consisting of dodecyl maltoside, dodecyl glucoside, octyl glucoside, octyl maltoside, decyl glucoside, decyl maltoside, decyl glucopyranoside, tridecyl glucoside, tridecyl maltoside, tetradecyl glucoside, tetradecyl maltoside, hexadecyl glucoside, hexadecyl maltoside, sucrose monooctanoate, sucrose monodecanoate, sucrose monododecanoate, sucrose monotridecanoate, sucrose monotetradecanoate and sucrose monohexadecanoate. In one embodiment, the alkyl glycoside is dodecyl maltoside or decyl glucopyranoside. In one preferred embodiment, the alkyl glycoside is dodecyl maltoside.

The concentration of the alkyl glycoside in the composition will typically be in the range 1-1000 µg/ml, e.g. 5-500 µg/ml, e.g. 10-200 µg/ml, such as 10-100 µg/ml or around 50 µg/ml. In one embodiment, the non-ionic surfactant is present at a concentration of 10-400 µg/ml e.g. 20-400 µg/ml, 50-400 µg/ml, 10-300 µg/ml, 20-300 µg/ml, 50-300 µg/ml, 10-200 µg/ml, 20-200 µg/ml, 50-200 µg/ml, 10-100 µg/ml, 20-100 µg/ml or 50-100 µg/ml.

In another embodiment, the concentration of insulin compound is 800-1000 U/ml and the non-ionic surfactant is present at a concentration of 50-200 µg/ml. In this embodiment, suitably the non-ionic surfactant is dodecyl maltoside.

In one embodiment, the composition of the system of the invention comprises (i) an insulin compound at a concentration of 50-500 U/ml (ii) ionic zinc, (iii) optionally citrate as a zinc binding species at a concentration of 1 mM or more, and (iv) a non-ionic surfactant which is an alkylglycoside; and wherein the composition is substantially free of EDTA and any other zinc binding species having a log K with respect to zinc ion binding of more than 12.3 at 25° C. Suitably, the citrate may be present in the composition at a concentration of 10-30 mM e.g. 10-20 mM e.g. 15-25 mM e.g. 20-30 mM.

Suitably the pH of the composition of the system of the invention is in the range 5.5-9.0 e.g. in the range 7.0-7.5. In order to minimise injection pain, the pH is preferably close to physiological pH (around pH 7.4). In one embodiment of the system of the invention, the pH is in the range 7.0-8.0 e.g. 7.5. In another embodiment of the system, the pH is in the range 7.6-8.0 e.g. 7.8.

Suitably, the composition of the system of the invention comprises a buffer (e.g. one or more buffers) in order to stabilise the pH of the composition, which can also be selected to enhance protein stability. In one embodiment, a buffer is selected to have a pKa close to the pH of the composition; for example, histidine is suitably employed as a buffer when the pH of the composition is in the range 5.0-7.0. Such a buffer may be employed in a concentration of 0.5-20 mM e.g. 2-5 mM. If histidine is included in the composition as a zinc binding species it will also have a buffering role at this pH. In another embodiment, the composition comprises a phosphate buffer. Sodium phosphate is suitably employed as a buffer when the pH of the composition is in the range 6.1-8.1. Such a buffer may be employed in a concentration of 0.5-20 mM e.g. 2-5 mM, e.g. 2 mM. Alternatively, in another embodiment, the composition of the system of the invention is further stabilised as disclosed in WO2008/084237 (herein incorporated by reference in its entirety), which describes a composition comprising a protein and one or more additives, characterised in that the system is substantially free of a conventional buffer, i.e. a compound with an ionisable group having a $pK_a$ within 1 unit of the pH of the composition at the intended temperature range of storage of the composition, such as 25° C. In this embodiment, the pH of the composition is set to a value at which the composition has maximum measurable stability with respect to pH; the one or more additives (displaced buffers) are capable of exchanging protons with the insulin compound and have $pK_a$ values at least 1 unit more or less than the pH of the composition at the intended temperature range of storage of the composition. The additives may have ionisable groups having $pK_a$ between 1 to 5 pH units, preferably between 1 to 3 pH units, most preferably from 1.5 to 2.5 pH units, of the pH of the aqueous composition at the intended temperature range of storage of the composition (e.g. 25° C.). Such additives may typically be employed at a concentration of 0.5-10 mM e.g. 2-5 mM.

The compositions of the system cover a wide range of osmolarity, including hypotonic, isotonic and hypertonic compositions. Preferably, the composition of the system of the invention is substantially isotonic. Suitably the osmolarity of the composition is selected to minimize pain according to the route of administration e.g. upon injection. Preferred compositions have an osmolarity in the range of about 200 to about 500 mOsm/L. Preferably, the osmolarity is in the range of about 250 to about 350 mOsm/L. More preferably, the osmolarity is about 300 mOsm/L.

Tonicity of the composition may be adjusted with a tonicity modifying agent (e.g. one or more tonicity modifying agents). Thus, the composition of the system of the invention may further comprise a tonicity modifying agent (e.g. one or more tonicity modifying agents). The tonicity modifying agent may be charged or uncharged. Examples of charged tonicity modifying agents include salts such as a combination of sodium, potassium, magnesium or calcium ions, with chloride, sulfate, carbonate, sulfite, nitrate, lactate, succinate, acetate or maleate ions (especially sodium chloride or sodium sulphate, particularly sodium chloride).

In one embodiment, the charged tonicity modifying agent is sodium chloride. The insulin compound compositions of the system of the invention may contain a residual NaCl concentration of 2-4 mM as a result of the use of standard acidification and subsequent neutralization steps employed in preparing insulin compositions. Amino acids such as arginine, glycine or histidine may also be used for this purpose. Charged tonicity modifying agent (e.g. NaCl) may be used at a concentration of 100-300 mM, e.g. around 150 mM. Preferably, the chloride is present at a concentration of >60 mM e.g. >65 mM, >75 mM, >80 mM, >90 mM, >100 mM, >120 mM or >140 mM.

Suitably an uncharged rather than a charged tonicity modifying agent is used when the concentration of insulin compound in the composition is 400 U/ml or more.

Examples of uncharged tonicity modifying agents include sugars, sugar alcohols and other polyols, such as trehalose, sucrose, mannitol, glycerol, 1,2-propanediol, raffinose, lactose, dextrose, sorbitol or lactitol (especially trehalose, mannitol, glycerol or 1,2-propanediol, particularly glycerol). In one embodiment, the uncharged tonicity modifying agent is selected from the group consisting of trehalose, mannitol, glycerol and 1,2-propanediol. In another embodiment, the uncharged tonicity modifying agent is glycerol. Uncharged tonicity modifying agent is preferably used at a concentration of 200-500 mM, e.g. around 300 mM. Another range of interest is 100-500 mM. In one embodiment, the uncharged tonicity modifying agent in the composition is at a concentration of 100-300 mM, e.g. 150-200 mM, 170-180 mM or around 174 mM. In one embodiment, the uncharged tonicity modifying agent in the composition is glycerol at a concentration of 100-300 mM, e.g. 150-200 mM, 170-180 mM or around 174 mM.

In one embodiment, the composition of the system of the invention comprises <10 mM chloride (e.g. sodium chloride), for example <9 mM, <8 mM, <7 mM, <6 mM or <5 mM, or is substantially free of chloride (e.g. sodium chloride) i.e. no chloride is added to the composition beyond any chloride that may be contributed as part of pH adjustment.

When the insulin compound is insulin lispro, the tonicity is suitably adjusted using an uncharged tonicity modifying agent, preferably at a concentration of 200-500 mM, e.g. around 300 mM. In this embodiment, the uncharged tonicity modifying agent is suitably selected from the group consisting of trehalose, mannitol, glycerol and 1,2-propanediol (most suitably glycerol). In another embodiment, the uncharged tonicity modifying agent is used at a concentration of 100-300 mM, e.g. 150-200 mM, 170-180 mM or around 174 mM. In one embodiment, the uncharged tonicity modifying agent is glycerol at a concentration of 100-300 mM, e.g. 150-200 mM, 170-180 mM or around 174 mM.

When the insulin compound is insulin aspart, the tonicity is suitably adjusted using an uncharged tonicity modifying agent, preferably at a concentration of 200-500 mM, e.g. around 300 mM. In this embodiment, the uncharged tonicity modifying agent is suitably selected from the group consisting of trehalose, mannitol, glycerol and 1,2-propanediol (most suitably glycerol). In another embodiment, the uncharged tonicity modifying agent is used at a concentration of 100-300 mM, e.g. 150-200 mM, 170-180 mM or around 174 mM. In one embodiment, the uncharged tonicity modifying agent is glycerol at a concentration of 100-300 mM, e.g. 150-200 mM, 170-180 mM or around 174 mM.

When the insulin compound is insulin glulisine, the tonicity is suitably adjusted using an uncharged tonicity modifying agent, preferably at a concentration of 200-500 mM, e.g. around 300 mM. In this embodiment, the uncharged tonicity modifying agent is suitably selected from the group consisting of trehalose, mannitol, glycerol and 1,2-propanediol (most suitably glycerol). In another embodiment, the uncharged tonicity modifying agent is used at a concentration of 100-300 mM, e.g. 150-200 mM, 170-180 mM or around 174 mM. In one embodiment, the uncharged tonicity modifying agent is glycerol at a concentration of 100-300 mM, e.g. 150-200 mM, 170-180 mM or around 174 mM.

The ionic strength of a composition of the system of the invention may be calculated according to the formula:

$$I = 0.5 \times \sum_{X=1}^{n} c_x z_x^2$$

in which $c_x$ is molar concentration of ion x (mol L$^{-1}$), $z_x$ is the absolute value of the charge of ion x and the sum covers all ions (n) present in the composition, wherein the contribution of the insulin compound and zinc binding species (if present) should be ignored for the purposes of the calculation. The contribution of ionic zinc should be included for the purposes of the calculation. For zwitterions, the absolute value of the charge is the total charge excluding polarity, e.g. for glycine the possible ions have absolute charge of 0, 1 or 2 and for aspartate the possible ions have absolute charge of 0, 1, 2 or 3.

In an embodiment, and particularly when the concentration of insulin compound in the composition is 400 U/ml or more, the ionic strength of the composition is suitably less than 40 mM, less than 30 mM, less than 20 mM or less than 10 mM.

In one embodiment the composition of the system of the invention comprises (i) an insulin compound at a concentration of 400-1000 U/ml e.g. 500-1000 U/ml (ii) ionic zinc, (iii) optionally citrate as a zinc binding species at a concentration of 1 mM or more, and (iv) an alkyl glycoside as a non-ionic surfactant; wherein the composition is substantially free of EDTA and any other zinc binding species having a log K with respect to zinc ion binding of more than 12.3 at 25° C., and wherein the ionic strength of the composition is less than 40 mM, said ionic strength being calculated using the formula I:

$$I = 0.5 \times \sum_{X=1}^{n} c_x z_x^2$$

in which $c_x$ is molar concentration of ion x (mol L$^{-1}$), $z_x$ is the absolute value of the charge of ion x and the sum covers all ions (n) present in the composition, wherein the contribution of the insulin compound and zinc binding species (if present) should be ignored for the purposes of the calculation. The contribution of ionic zinc should be included for the purposes of the calculation. Suitably, the citrate is present in the composition at a concentration of 30-60 mM e.g. 30-50 mM e.g. 40-50 mM.

In another embodiment, the composition of the system of the invention comprises (i) an insulin compound at a concentration of 400-1000 U/ml e.g. 500-1000 U/ml (ii) ionic zinc, (iii) optionally citrate as a zinc binding species at a concentration of 1 mM or more, and (iv) a non-ionic surfactant which is an alkyl glycoside; and wherein the composition is substantially free of EDTA and any other zinc binding species having a log K with respect to zinc ion binding of more than 12.3 at 25° C. Suitably, the citrate may be present in the composition at a concentration of 30-60 mM e.g. 30-50 mM, e.g. 30-40 mM, e.g. 35-45 mM, e.g. 40-50 mM. Suitably the ionic strength of the composition is less than 40 mM calculated using Formula I. Suitably, the formulation of the invention comprises <10 mM chloride (e.g. sodium chloride), for example <9 mM, <8 mM, <7 mM, <6 mM or <5 mM, or is substantially free of chloride (e.g. sodium chloride) i.e. no chloride is added to the formulation beyond any chloride that may be contributed as part of pH adjustment. In one embodiment, the composition comprises an uncharged tonicity modifying agent.

In one embodiment, the insulin compound is present at a concentration of 400-1000 U/ml e.g. >400-1000 U/ml, 500-1000 U/ml, >500-1000 U/ml, 600-1000 U/ml, >600-1000 U/ml, 700-1000 U/ml, >700-1000 U/ml, 750-1000 U/ml, >750-1000 U/ml, 800-1000 U/ml, >800-1000 U/ml, 900-1000 U/ml, >900-1000 U/ml or 1000 U/ml, and the ionic strength taking account of ions in the composition except for the zinc binding species, the insulin compound and the ionic zinc is less than 30 mM, e.g. less than 20 mM, e.g. less than 10 mM such as 1-10 mM. In a further embodiment, the ionic strength taking account of ions in the composition except for the zinc binding species, the insulin compound and the ionic zinc is less than 25 mM, less than 20 mM, less than 15 mM, or less than 10 mM, or is in the range 5-<30 mM, 5-30 mM, 5-20 mM, 2-20 mM, 1-10 mM, 2-10 mM or 5-10 mM.

When the insulin compound is insulin lispro a concentration of 400-1000 U/ml e.g. >400-1000 U/ml, 500-1000 U/ml, >500-1000 U/ml, 600-1000 U/ml, >600-1000 U/ml, 700-1000 U/ml, >700-1000 U/ml, 750-1000 U/ml, >750-1000 U/ml, 800-1000 U/ml, >800-1000 U/ml, 900-1000 U/ml, >900-1000 U/ml or 1000 U/ml, the ionic strength of the composition is suitably kept to a minimum level since higher ionic strength compositions are less stable than lower ionic strength compositions, particularly at high concentrations of insulin. Suitably the ionic strength taking account of ions in the composition except for the zinc binding species, the insulin compound and the ionic zinc is less than 30 mM, e.g. less than 20 mM, e.g. less than 10 mM such as 1-10 mM. In particular, the ionic strength taking account of ions in the composition except for the zinc binding species, the insulin compound and the ionic zinc is less than 25 mM, less than 20 mM, less than 15 mM, or less than 10 mM, or is in the range 5-<30 mM, 5-30 mM, 5-20 mM, 2-20 mM, 1-10 mM, 2-10 mM or 5-10 mM.

When the insulin compound is insulin aspart at a concentration of 400-1000 U/ml e.g. >400-1000 U/ml, 500-1000 U/ml >500-1000 U/ml, 600-1000 U/ml, >600-1000 U/ml, 700-1000 U/ml, >700-1000 U/ml, 750-1000 U/ml, >750-1000 U/ml, 800-1000 U/ml, >800-1000 U/ml, 900-1000 U/ml, >900-1000 U/ml or 1000 U/ml, the ionic strength of the composition is suitably kept to a minimum level since higher ionic strength compositions are less stable than lower ionic strength compositions. Suitably the ionic strength taking account of ions in the composition except for the zinc binding species, the insulin compound and the ionic zinc is less than 30 mM, e.g. less than 20 mM, e.g. less than 10 mM. In particular, the ionic strength taking account of ions in the composition except for the zinc binding species, the insulin compound and the ionic zinc is less than 25 mM, less than 20 mM, less than 15 mM, or less than 10 mM, or is in the range 5-<30 mM, 5-30 mM, 5-20 mM, 2-20 mM, 1-10 mM, 2-10 mM or 5-10 mM. The tonicity may suitably be adjusted using an uncharged tonicity modifying agent.

When the insulin compound is insulin glulisine at a concentration of 400-1000 U/ml e.g. >400-1000 U/ml, 500-1000 U/ml >500-1000 U/ml, 600-1000 U/ml, >600-1000 U/ml, 700-1000 U/ml, >700-1000 U/ml, 750-1000 U/ml, >750-1000 U/ml, 800-1000 U/ml, >800-1000 U/ml, 900-1000 U/ml, >900-1000 U/ml or 1000 U/ml, the ionic strength of the composition is suitably kept to a minimum level since higher ionic strength compositions may be less stable than lower ionic strength compositions. Suitably the ionic strength taking account of ions in the composition except for the zinc binding species, the insulin compound and the ionic zinc is less than 30 mM, e.g. less than 20 mM, e.g. less than 10 mM. In particular, the ionic strength taking account of ions in the composition except for the zinc binding species, the insulin compound and ionic zinc is less than 25 mM, less than 20 mM, less than 15 mM, or less than 10 mM, or is in the range 5-<30 mM, 5-30 mM, 5-20 mM, 2-20 mM, 1-10 mM, 2-10 mM or 5-10 mM.

The composition of the system of the invention may optionally further comprise a preservative (e.g. one or more preservatives). One or more preservatives may be employed. In one embodiment, the preservative is selected from the group consisting of phenol, m-cresol, chlorocresol, benzyl alcohol, propylparaben, methylparaben, benzalkonium chloride and benzethonium chloride.

The composition of the system of the invention may optionally further comprise nicotinamide. The presence of nicotinamide may further increase the speed of onset of action of insulin formulated in compositions of the system of the invention. Suitably, the concentration of nicotinamide is in the range 10-150 mM, preferably in the range 20-100 mM, such as around 80 mM.

The composition of the system of the invention may optionally further comprise nicotinic acid or a salt thereof. The presence of nicotinic acid or a salt thereof may also further increase the speed of onset of action of insulin formulated in compositions of the system of the invention. Suitably, the concentration of nicotinic acid or a salt thereof is in the range 10-150 mM, preferably in the range 20-100 mM, such as around 80 mM. Example salts include metal salts such as sodium, potassium and magnesium salts.

Typically, one of nicotinamide and nicotinic acid (or as salt thereof) may be included in the composition but not both.

In an embodiment, the composition comprises (i) an insulin compound, (ii) ionic zinc, (iii) a nicotinic compound, (iv) an alkyl glycoside as a non-ionic surfactant; and (v) a salt selected from the salts formed between Group 1 metals and a mono or divalent anion. In an embodiment, the nicotinic compound is nicotinamide or nicotinic acid or a salt thereof. In an embodiment, the nicotinic compound is present in the composition at a concentration of 10-150 mM. In an embodiment, the Group 1 metal is sodium. In an embodiment, the salt is the sodium salt of a mono or divalent anion. In an embodiment, the anion is chloride or acetate. Thus, for example, the salt is sodium chloride or sodium acetate. In an embodiment, the salt is present in the composition at a concentration of 30-200 mM.

The composition of the system of the invention may optionally further comprise treprostinil or a salt thereof. The presence of the treprostinil may further increase the speed of onset of action of insulin formulated in compositions of the system of the invention. Suitably, the concentration of treprostinil in the composition is in the range of 0.1-12 µg/ml e.g. 0.1-10 µg/ml, 0.1-9 µg/ml, 0.1-8 µg/ml, 0.1-7 µg/ml, 0.1-6 µg/ml, 0.1-5 µg/ml, 0.1-4 µg/ml, 0.1-3 µg/ml, 0.1-2 µg/ml, 0.5-2 µg/ml e.g. about 1 µg/ml.

In one embodiment, the composition does not contain a vasodilator. In a further embodiment, the composition does not contain treprostinil, nicotinamide, nicotinic acid or a salt thereof.

Compositions of the system may optionally include other beneficial components including stabilising agents. For example, amino acids such as arginine or proline may be included which may have stabilising properties. Thus, in one embodiment, the compositions of the system comprise arginine.

In an embodiment of the invention the compositions are free of acids selected from glutamic acid, ascorbic acid, succinic acid, aspartic acid, maleic acid, fumaric acid, adipic acid and acetic acid and are also free from the corresponding ionic forms of these acids.

In an embodiment of the invention the compositions of the system are free of arginine.

In an embodiment of the invention the compositions of the system are free of protamine and protamine salts.

In an embodiment of the invention the compositions of the system are free of magnesium ions.

The addition of magnesium ions e.g. in the form of magnesium chloride may provide a stabilising effect. Thus, in an embodiment of the invention the composition contains magnesium ions e.g. $MgCl_2$.

In an embodiment of the invention the compositions of the system are free of calcium ions.

Compositions of the system may further comprise an additional therapeutically active agent (an "active agent"), in particular an agent of use in the treatment of diabetes (i.e. in addition to the insulin compound in particular the rapid-acting insulin compound) e.g. an amylin analogue or a GLP-1 agonist. In one embodiment, the composition further comprises an amylin analogue such as pramlintide, suitably at a concentration of 0.1-10 mg/ml e.g. 0.2-6 mg/ml. In one embodiment, the composition further comprises a GLP-1 agonist such as liraglutide, dulaglutide, albiglutide, exenatide or lixisenatide, suitably at a concentration of 10 µg/ml to 50 mg/ml e.g. 200 µg/ml to 10 mg/ml or 1 mg/ml to 10 mg/ml.

Suitably the compositions of the system are sufficiently stable that the concentration of high molecular weight species remains low upon extended storage. The term "high molecular weight species" as used herein, refers to any irreversibly formed component of the protein content which has an apparent molecular weight at least about double the molecular weight of the parent insulin compound, as detected by a suitable analytical method, such as size-exclusion chromatography. That is, high molecular weight species are multimeric aggregates of the parent insulin compound. The multimeric aggregates may comprise the parent protein molecules with considerably altered conformation or they may be an assembly of the parent protein units in the native or near-native conformation. The determination of high molecular weight species can be done using methods known in the art, including size exclusion chromatography, electrophoresis, analytical ultracentrifugation, light scattering, dynamic light scattering, static light scattering and field flow fractionation.

Suitably the compositions of the system are sufficiently stable that they remain substantially free of visible particles after storage at 30° C. for at least one month or more, two months or more, or three months or more. Visible particles are suitably detected using the 2.9.20. European Pharmacopoeia Monograph (Particulate Contamination: Visible Particles). For example, a composition is substantially free of visible particles if it has a Visual score according to Visual Assessment Scoring Method B of 1, 2 or 3, especially 1 or 2 according to the definition given in the Examples section.

Suitably the compositions of the system are sufficiently stable that there is minimal increase in soluble aggregates such as <0.5%, <0.2% or <0.1% increase after storage at 30° C. for one month or more, two months or more or three months or more. Soluble aggregates are suitable detected using SEC (see General Methods).

Suitably the compositions of the system are sufficiently stable that the concentration of related species remains low upon extended storage. The term "related species" as used herein, refers to any component of the protein content formed by a chemical modification of the parent insulin compound, particularly desamido or cyclic imide forms of insulin. Related species are suitably detected by RP-HPLC.

In a preferred embodiment, the composition of the system of the invention retains at least 95%, e.g. at least 96%, e.g. at least 97%, e.g. at least 98%, e.g. at least 99% parent insulin compound (by weight of total protein) after storage at 30° C. for one, two or three months. The percentage of insulin compound (by weight of total protein) may be determined by size-exclusion chromatography or RP-HPLC.

In a preferred embodiment, the composition of the system of the invention comprises no more than 4% (by weight of total protein), preferably no more than 2% high molecular weight species (e.g. visible particles and/or soluble aggregates) after storage at 30° C. for one, two or three months.

In a preferred embodiment, the composition of the system of the invention comprises no more than 4% (by weight of total protein), preferably no more than 2%, preferably no more than 1% A-21 desamido form of the insulin compound after storage at 30° C. for one, two or three months.

In preferred embodiments, a composition of the system of the invention should exhibit an increase in high molecular weight species (e.g. visible particles and/or soluble aggregates) during storage which is at least 10% lower, preferably at least 25% lower, more preferably at least 50% lower, than a composition lacking the alkyl glycoside as non-ionic surfactant but otherwise identical, following storage under the same conditions (e.g. 30° C.) and length of time (e.g. one, two or three months).

In preferred embodiments, a composition of the system of the invention should exhibit an increase in related species during storage which is at least 10% lower, preferably at least 25% lower, more preferably at least 50% lower, than a composition lacking the alkyl glycoside as non-ionic surfactant but otherwise identical, following storage under the same conditions (e.g. 30° C.) and length of time (e.g. one, two or three months).

The speed of action of a composition of the system of the invention may be determined in the Diabetic Pig Pharmacokinetic/Pharmacodynamic Model (see Examples, General Methods (c)). In preferred embodiments, a composition of the present invention exhibits a $T_{max}$ (i.e. time to peak insulin concentration) that is at least 20% shorter, preferably at least 30% shorter than a composition lacking the zinc binding species having a log K with respect to zinc ion binding in the range 4.5-12.3 (e.g. in the range 4.5-10) at 25° C. but otherwise identical, using the model. In preferred embodiments, a composition of the present invention exhibits an area under the curve on the pharmacodynamics profile within the first 45 minutes after injection that is at least 20% greater, preferably at least 30% greater than a composition lacking the zinc binding species having a log K with respect to zinc ion binding in the range 4.5-12.3 (e.g. in the range 4.5-10) at 25° C. but otherwise identical, using the model.

In one embodiment, the composition of the system of the invention comprises (i) insulin lispro at a concentration of 400-1000 U/ml e.g. 500-1000 U/ml, (ii) ionic zinc, (iii) optionally a zinc binding species at a concentration of 1 mM or more selected from species having a log K with respect to zinc ion binding in the range 4.5-12.3 at 25° C. e.g. citrate, and (iv) a non-ionic surfactant which is an alkyl glycoside; and wherein the composition is substantially free of EDTA and any other zinc binding species having a log K with respect to zinc ion binding of more than 12.3 at 25° C., which exhibits a $T_{max}$ (i.e. time to peak insulin concentration) that is at least 20% shorter, preferably at least 30% shorter than an aqueous composition consisting of: insulin lispro (100 U/ml), sodium phosphate (13.2 mM), glycerol (174 mM), m-cresol (29 mM), ionic zinc (19.7 μg/ml, excluding counter-ion) adjusted to pH 7.3, using the Diabetic Pig Pharmacokinetic/Pharmacodynamic Model (see Examples, General Methods (c)). In another embodiment, the present invention provides a composition comprising (i) insulin ispro at a concentration of 400-1000 U/ml e.g. 400-1000 U/ml e.g. 500-1000 U/ml, (ii) ionic zinc, (iii) optionally a zinc binding species at a concentration of 1 mM or more selected from species having a log K with respect to zinc ion binding in the range 4.5-12.3 at 25° C. e.g. citrate, and (iv) a non-ionic surfactant which is an alkyl glycoside; and wherein the composition is substantially free of EDTA and any other zinc binding species having a log K with respect to zinc ion binding of more than 12.3 at 25° C., which exhibits an area under the curve on the pharmacodynamics profile within the first 45 minutes after injection that is at least 20% greater, preferably at least 30% greater than an aqueous composition consisting of: insulin lispro (100 U/ml), sodium phosphate (13.2 mM), glycerol (174 mM), m-cresol (29 mM), ionic zinc (19.7 μg/ml, excluding counter-ion) adjusted to pH 7.3, using the Diabetic Pig Pharmacokinetic/Pharmacodynamic Model (see Examples, General Methods (c)).

In one embodiment, the composition of the system of the invention comprises (i) insulin aspart at a concentration of 400-1000 U/ml e.g. 400-1000 U/ml e.g. 500-1000 U/ml, (ii) ionic zinc, (iii) optionally a zinc binding species at a concentration of 1 mM or more selected from species having a log K with respect to zinc ion binding in the range 4.5-12.3 at 25° C. e.g. citrate, and (iv) a non-ionic surfactant which is an alkyl glycoside; and wherein the composition is substantially free of EDTA and any other zinc binding species having a log K with respect to zinc ion binding of more than 12.3 at 25° C., which exhibits a $T_{max}$ (i.e. time to peak insulin concentration) that is at least 20% shorter, preferably at least 30% shorter than an aqueous composition consisting of: insulin aspart (100 U/ml), sodium phosphate (7 mM), glycerol (174 mM), sodium chloride (10 mM), phenol (15.9 mM), m-cresol (15.9 mM) and ionic zinc (19.7 µg/ml, excluding counter-anion) adjusted to pH 7.4, using the Diabetic Pig Pharmacokinetic/Pharmacodynamic Model (see Examples, General Methods (c)).

In another embodiment, the present invention provides a composition comprising (i) insulin aspart at a concentration of 400-1000 U/ml e.g. 400-1000 U/ml e.g. 500-1000 U/ml, (ii) ionic zinc, (iii) optionally a zinc binding species at a concentration of 1 mM or more selected from species having a log K with respect to zinc ion binding in the range 4.5-12.3 at 25° C. e.g. citrate, and (iv) a non-ionic surfactant which is an alkyl glycoside; and wherein the composition is substantially free of EDTA and any other zinc binding species having a log K with respect to zinc ion binding of more than 12.3 at 25° C., which exhibits an area under the curve on the pharmacodynamics profile within the first 45 minutes after injection that is at least 20% greater, preferably at least 30% greater than an aqueous composition consisting of: insulin aspart (100 U/ml), sodium phosphate (7 mM), glycerol (174 mM), sodium chloride (10 mM), phenol (15.9 mM), m-cresol (15.9 mM) and ionic zinc (19.7 µg/ml, excluding counter-anion) adjusted to pH 7.4, using the Diabetic Pig Pharmacokinetic/Pharmacodynamic Model (see Examples, General Methods (c)).

In preferred embodiments, a composition of the system of the invention is bioequivalent to a standard composition comprising the insulin compound at 100 U/ml.

As used herein, "bioequivalent" means that the composition of the system of the invention has an equivalent or similar pharmacokinetic/pharmacodynamic (PK/PD) profile to a standard composition. For example, the composition of the system of the invention exhibits a $T_{MAX}$ or $T_{1/2MAX}$ (measured in accordance with the Diabetic Pig Pharmacokinetic/Pharmacodynamic Model described in section (c) of General Methods) which is substantially the same as (e.g. within ±20% of, e.g. within ±10% of) that of the standard composition. Bioequivalence can also be established by applying the Student's t-test to the pharmacokinetic/pharmacodynamics results achieved using two different compositions as described in the diabetic pig pharmacokinetic/pharmacodynamic model described in section (c) of General Methods.

By "standard composition" is meant a commercially available composition of the same insulin compound at a concentration of 100 U/ml such as HUMALOG® (for insulin lispro) or NOVORAPID® (for insulin aspart) or APIDRA® (for insulin glulisine).

In one embodiment, the composition of the system of the invention comprises an insulin compound at a concentration of 400-1000 U/mL e.g. 500-1000 U/mL and wherein the composition is bioequivalent to a standard composition comprising the insulin compound at a concentration of 100 U/mL. In another embodiment, the absorption of insulin compound into the blood stream of the mammal after administration using the system is bioequivalent to a standard composition at a concentration comprising the insulin compound at a concentration of 100 U/mL. In another embodiment, the glucose reduction response caused by administration of a given amount of insulin compound to the mammal using the system is bioequivalent to a standard composition comprising the insulin compound at a concentration of 100 U/mL.

In one embodiment, a composition of the system of the invention wherein the insulin compound is insulin lispro is bioequivalent to a commercial composition of insulin lispro at a concentration of 100 U/ml e.g. an aqueous composition consisting of: insulin lispro (100 U/ml), sodium phosphate (13.2 mM), glycerol (174 mM), m-cresol (29 mM), ionic zinc (19.7 µg/ml, excluding counter-ion) adjusted to pH 7.3 (i.e. the composition of HUMALOG®).

In one embodiment, a composition of the system of the invention wherein the insulin compound is insulin aspart is bioequivalent to a commercial composition of insulin aspart at a concentration of 100 U/ml e.g. an aqueous composition consisting of: insulin aspart (100 U/ml), sodium phosphate (7 mM), glycerol (174 mM), sodium chloride (10 mM), phenol (15.9 mM), m-cresol (15.9 mM) and ionic zinc (19.7 µg/ml, excluding counter-anion) adjusted to pH 7.4 (i.e. the composition of NOVORAPID®).

According to further aspects of the invention, there is provided a composition of the system of the invention for use in the treatment of a subject suffering from diabetes mellitus. There is also provided a method of treatment of diabetes mellitus which comprises administering to a subject in need thereof an effective amount of a composition of the system of the invention.

A typical insulin dose of the composition of the system of the invention is 2-100 U e.g. 2-30 U, e.g. 5-15 U. Administration should suitably occur in the window between 15 minutes before eating (i.e. before start of a meal) and 15 minutes after eating (i.e. after end of a meal).

In one embodiment, the composition of the system of the invention is co-administered with a long acting insulin such as insulin glargine or insulin degludec, suitably at a concentration of 50-1000 U/ml e.g. 100-500 U/ml or 100-200 U/ml.

The composition of the system of the invention is for administration by injection, preferably by subcutaneous injection.

The system may comprise a dial mechanism enabling selection of a specific desired volume of the composition for delivery to the mammal. In one embodiment, the volume of composition selected for delivery is between 0.1-100 µL e.g. 0.25-50 µL, e.g. 0.50-20 µL. Suitably, the selected volume is determined by the dial mechanism in increments of 0.1-10 µL e.g. 0.25-5 µL e.g. 0.5-2 µL. Preferably, the ratio between the delivered dose of insulin compound delivered (U) and the delivered volume (µL) is at least 0.4:1 e.g. at least 0.5:1 e.g. at least 0.6:1.

The reservoir of the system which comprises the aqueous liquid pharmaceutical composition for delivery by means of said injection pen will typically have a total volume of up to 3 mL e.g. 3 mL, e.g. 2 mL, e.g. 1 mL The reservoir of the system will be retained in a container e.g. a cartridge. The containers may be a replaceable or refillable component of the system.

Injection pen systems provide a demanding environment for preserving the activity of insulin. For example, the reservoirs of such systems are exposed to warmth (particularly if carried close the body) and agitation (due to movement of the body).

Suitably the compositions of the system are sufficiently stable that they remain substantially free of visible particles after use for 4 weeks or more, 8 weeks or more, or 12 weeks or more. Visible particles are suitably detected using the 2.9.20. European Pharmacopoeia Monograph (Particulate Contamination: Visible Particles) combined with Scoring Method B (see General Methods). For example, a composition is substantially free of visible particles if it has a Visual score according to Visual Assessment Scoring Method B of 1, 2 or 3, especially 1 or 2 according to the definition given in the Examples section.

Suitably the compositions of the system are sufficiently stable that they show a minimal increase in soluble aggregates, such as less than 1% e.g. less than 0.5% e.g. less than 0.2%, following the use of the system of the invention for 4 weeks or more, 8 weeks or more, or 12 weeks or more. Soluble aggregates are suitably detected using Size Exclusion Chromatography (see General Methods).

In an embodiment, a composition of the system of the invention is more stable than in the absence of alkyl glycoside during operation of the injection pen for 4 weeks or more e.g. 8 weeks or more e.g. 12 weeks or more. For example, a composition of the system of the invention forms fewer visible particles and/or soluble aggregates than an identical composition in the absence of alkyl glucoside during operation of the injection pen for 4 weeks or more e.g. 8 weeks or more, e.g. 12 weeks or more. Visual particles and soluble aggregates can be determined by Visual Assessment Scoring Method B and SEC (see General Methods).

In an embodiment, said in-use stability is indicated by the presence of fewer visible particles and/or soluble aggregates in the reservoir after use for the said number of weeks. In an embodiment, said in-use stability is indicated by the presence of fewer visible particles and/or soluble aggregates in a delivered dose after use for the said number of weeks. Visual particles and soluble aggregates can be determined by Visual Assessment Scoring Method B and SEC (see General Methods).

In an embodiment, the injection pen of the system of the invention is disposable. Suitably, the injection pen is to be disposed of either when the insulin is used up or after a specified time, such as after 2 weeks of use e.g. after 4 weeks of use, e.g. after 8 weeks of use.

In another embodiment, the injection pen is reusable and the reservoir is replaced as needed. Suitably, the reservoir is to be disposed of either when the insulin is used up or after a specified time, such as after 2 weeks of use e.g. after 4 weeks of use, e.g. after 8 weeks of use.

The reservoir (often called "cartridge") is typically in the shape of a syringe and the pen comprises a piston mechanism designed to apply the appropriate pressure to dispense the required amount of insulin based on the values set (dialled) by the user.

Suitably the injector mechanism comprises a needle. The needle gauge typically ranges from 29 to 32 and the needle length typically ranges from 5 to 12 mm. In one embodiment, a new needle needs to be attached to the pen prior to each injection, using a specific mechanism such as screw thread or a push-on thread, and disposed of after use. In one embodiment the needle is a retractable needle. In one embodiment the injector mechanism comprises a spring-loaded retractable needle. The needle can be equipped with a protective shield to reduce the risk of needle-stick injuries or to allay patient anxiety about the needle use. Examples of commercially available insulin pens include KWIKPEN®, SOLOSTAR®, FLEXPEN®, FLEXTOUCH®, HUMAPEN®, NOVOPEN®.

In an embodiment, the system administers the composition subcutaneously to the mammal. In an aspect of the invention, there is provided use of the system in the treatment of diabetes mellitus in said mammal. In an embodiment, the mammal requires 200 U of insulin per day or more. In another embodiment, the mammal has developed insulin resistance. In an embodiment, the mammal is a human.

In another embodiment, there is provided a method of treatment of diabetes mellitus which comprises administering to a mammal in need thereof an effective amount of an insulin compound containing composition via an injection pen using the system of the invention. In an embodiment, the mammal requires 200 U of insulin per day or more. In another embodiment, the mammal has developed insulin resistance. Suitably, the mammal is a human.

Compositions of the system of the invention may be prepared by mixing the ingredients. For example, the insulin compound may be dissolved in an aqueous composition comprising the other components. Alternatively, the insulin compound may be dissolved in a strong acid (typically HCl), after dissolution diluted with an aqueous composition comprising the other components, and then pH adjusted to the desired pH with addition of alkali (e.g. NaOH). As a variation on this method, a step of neutralising the acid solution may be performed before the dilution step and it may then not be necessary to adjust the pH after the dilution step (or a small adjustment only may be necessary).

In another aspect of the invention, there is provided the use of an alkyl glycoside as a non-ionic surfactant to improve the stability of an insulin compound in an aqueous liquid pharmaceutical composition in an injection pen system comprising an injection pen and an aqueous composition for delivery by means of said injection pen to a mammal, wherein the composition comprises (i) an insulin compound, (ii) ionic zinc and (iii) an alkyl glycoside as a non-ionic surfactant.

In a further aspect of the invention, there is provided a method of improving the stability of an insulin compound to be administered by an injection pen system, which comprises adding an alkyl glycoside to an aqueous liquid pharmaceutical composition comprising the insulin compound and ionic zinc.

Systems of the invention in at least some embodiments are expected to have one or more of the following advantageous properties:

- The systems can deliver high strength insulin that is rapid acting or ultra-rapid acting;
- The systems can deliver larger quantity of insulin within the in-use period, which improves convenience for the user, particularly if the user has developed insulin resistance or requires large quantities of insulin for a different reason;
- The systems can be used for extended periods of time, such as >4 weeks;
- Compositions of the system have good physical stability during use, for example after use for a number of weeks or months;
- Compositions of the system have good physical stability upon storage, especially as measured by the amount of HMWS or visual detection of particles;
- Compositions of the system have good chemical stability upon storage, especially as measured by the amount of related products e.g. products of deamidation;
- Compositions of the system have rapid speed of action, typically faster than normal human insulin, upon administration to a subject;
- Compositions of the system have rapid speed of action, typically as fast as a standard composition with insulin compound concentration of 100 U/ml;
- Compositions of the system have high insulin concentration while maintaining a rapid speed of action.

ABBREVIATIONS

DETA diethylenetriamine
EDTA ethylenediaminetetraacetate
EGTA ethyleneglycoltetraacetate
HPLC high performance liquid chromatography
HMWS high molecular weight species
RP reverse phase
SEC size-exclusion chromatography
TETA triethylenetetramine
PD pharmacodynamic
PK pharmacokinetic

EXAMPLES

General Methods
(a) Size Exclusion Chromatography (SEC)

Ultra-high performance size exclusion chromatography of insulin preparations was performed using the Waters ACQUITY H-class Bio UPLC® system with a 1.7 µm Ethylene Bridged Hybrid 125 Å pore packing material in a 300 mm by 4.6 mm column. The column was equilibrated in 0.65 mg/ml L-arginine, 20% v/v acetonitrile, 15% v/v glacial acetic acid mobile phase and 10 µl of sample, acidified with 0.01M HCl, was analysed at 0.4 mL/min, with 276 nm UV detection. All analyses were performed at ambient temperature.

(b) Reversed-Phase Chromatography (RP-HPLC)

Ultra-high performance reverse phase chromatography was performed using the Waters ACQUITY H-class Bio UPLC® system with a 1.7 µm Ethylene Bridged Hybrid particle, 130 Å pore resin trifunctionally immobilised with a C18 ligand in a 50 mm by 2.1 mm column. Insulin samples were bound in a 82% w/v $Na_2SO_4$, 18% v/v acetonitrile, pH 2.3 mobile phase and eluted in 50% w/v $Na_2SO_4$, 50% v/v acetonitrile gradient flow. 2 µl of sample was acidified with 0.01M HCl and analysed at 0.61 mL/min, with 214 nm UV detection. All analyses were performed at 40° C.

(c) The Diabetic Pig Pharmacokinetic/Pharmacodynamic Model: Method for Determining Speed of Action 10 male diabetic Yucatan miniature pigs were used. Pigs were injected subcutaneously with a sample of the test formulation and blood was taken (1 or 2 ml) at various time-points (min) with respect to the injection up to around 240 min after the injection. For pharmacodynamics profile, serum was analysed for glucose (using a commercially available glucometer). For pharmacokinetic profile, insulin concentration was determined in the serum using an immunoassay.

In order to evaluate the formulations for bioequivalence, mean values of $T_{MAX}$ (i.e. time to reach the maximum insulin concentration in serum) and corresponding standard deviation were calculated across the whole set of 10 pigs used in the study. Similarly, mean values of $T_{1/2MAX}$ (i.e. time to reach half of the maximum concentration) and corresponding standard deviation were calculated across the whole set of 10 pigs used in the study. Student t-test (95% confidence interval) was subsequently applied to allow assessment of bioequivalence between any two formulations tested. If the p-value of the t-test applied to the results populations of two samples was ≥0.05 the samples were considered bioequivalent, if the result was <0.05 then the samples were considered non-bioequivalent.

(d) Visual Assessment

Visible particles are suitably detected using the 2.9.20. European Pharmacopoeia Monograph (Particulate Contamination: Visible Particles). The apparatus required consists of a viewing station comprising:

- a matt black panel of appropriate size held in a vertical position
- a non-glare white panel of appropriate size held in a vertical position next to the black panel
- an adjustable lampholder fitted with a suitable, shaded, white-light source and with a suitable light diffuser (a viewing illuminator containing two 13 W fluorescent tubes, each 525 mm in length, is suitable). The intensity of illumination at the viewing point is maintained between 2000 lux and 3750 lux.

Any adherent labels are removed from the container and the outside washed and dried. The container is gently swirled or inverted, ensuring that air bubbles are not introduced, and observed for about 5 s in front of the white panel. The procedure is repeated in front of the black panel. The presence of any particles is recorded.

The visual scores are ranked as follows:

Visual Assessment Scoring Method A

Visual score 1: clear solution free of visible particles
Visual score 2: slight particle formation
Visual score 3: more significant precipitation Visual Assessment Scoring Method B Visual score 1: Clear solution, virtually free of particles
Visual score 2: ~5 very small particles
Visual score 3: ~10-20 very small particles
Visual score 4: 20-50 particles, including larger particles
Visual score 5: >50 particles, including larger particles Whilst the particles in samples with visual scores 4 and 5 are clearly detectable on casual visual assessment under normal light, samples with visual score 1-3 generally appear as clear solutions on the same assessment. Samples with visual scores 1-3 are considered to be "Pass"; samples with visual score 4-5 are considered to be "Fail".

Example 1—Example Formulations

The following example formulations may be prepared:

Example A

| | |
|---|---|
| Insulin lispro | 100 U/ml |
| Sodium phosphate | 2 mM |
| phenol | 15.9 mM |
| m-cresol | 15.9 mM |
| Ionic zinc (as $ZnCl_2$) | 19.7 µg/ml (0.3 mM), equals 0.55% (w/w) based on the weight of insulin compound in the formulation |
| Citrate (as trisodium salt) | 22 mM |
| Glycerol | 174 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.4 | |

Example B

| | |
|---|---|
| Insulin aspart | 100 U/ml |
| Sodium phosphate | 2 mM |
| phenol | 15.9 mM |
| m-cresol | 15.9 mM |
| Ionic zinc (as $ZnCl_2$) | 19.7 μg/ml (0.3 mM), equals 0.55% (w/w) based on the weight of insulin compound in the formulation |
| Citrate (as trisodium salt) | 22 mM |
| Glycerol | 174 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.4 | |

Example C

| | |
|---|---|
| Insulin aspart | 100 U/ml |
| Sodium phosphate | 2 mM |
| phenol | 15.9 mM |
| m-cresol | 15.9 mM |
| Ionic zinc (as $ZnCl_2$) | 19.7 μg/ml (0.3 mM), equals 0.55% (w/w) based on the weight of insulin compound in the formulation |
| Citrate (as trisodium salt) | 22 mM |
| NaCl | 150 mM |
| Surfactant | dodecyl maltoside (0.05 mg/ml) |
| Water for injection | qs |
| Additional NaCl | Acidification and subsequent neutralisation during preparation results in formation of 2-4 mM NaCl |
| pH adjusted to 7.4 | |

Example D

| | |
|---|---|
| Insulin glulisine | 100 U/ml |
| Sodium phosphate | 2 mM |
| phenol | 15.9 mM |
| m-cresol | 15.9 mM |
| Ionic zinc (as $ZnCl_2$) | 19.7 μg/ml (0.3 mM), equals 0.55% (w/w) based on the weight of insulin compound in the formulation |
| Citrate (as trisodium salt) | 22 mM |
| Glycerol | 174 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.4 | |

Example E

| | |
|---|---|
| Insulin lispro | 100 U/ml |
| Sodium phosphate | 2 mM |
| phenol | 15.9 mM |
| m-cresol | 15.9 mM |
| Ionic zinc (as $ZnCl_2$) | 19.7 μg/ml (0.3 mM), equals 0.55% (w/w) based on the weight of insulin compound in the formulation |
| Citric acid | 22 mM |
| Glycerol | 174 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.8 | |

Example F

| | |
|---|---|
| Insulin aspart | 100 U/ml |
| Sodium phosphate | 2 mM |
| phenol | 15.9 mM |
| m-cresol | 15.9 mM |
| Ionic zinc (as $ZnCl_2$) | 19.7 μg/ml (0.3 mM), equals 0.55% (w/w) based on the weight of insulin compound in the formulation |
| Citric acid | 22 mM |
| NaCl | 150 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.4 | |

Example G

| | |
|---|---|
| Insulin aspart | 100 U/ml |
| Sodium phosphate | 2 mM |
| phenol | 15.9 mM |
| m-cresol | 15.9 mM |
| Ionic zinc (as $ZnCl_2$) | 19.7 μg/ml (0.3 mM), equals 0.55% (w/w) based on the weight of insulin compound in the formulation |

| | |
|---|---|
| Citric acid | 22 mM |
| NaCl | 150 mM |
| Surfactant | dodecyl maltoside (0.05 mg/ml) |
| Water for injection | qs |
| Additional NaCl | Acidification and subsequent neutralisation during preparation results in formation of 2-4 mM NaCl |
| pH adjusted to 7.8 | |

Example H

| | |
|---|---|
| Insulin aspart | 1000 U/ml |
| Sodium phosphate | 2 mM |
| phenol | 15.9 mM |
| m-cresol | 15.9 mM |
| Ionic zinc (as $ZnCl_2$) | 197 µg/ml (3 mM), equals 0.55% (w/w) based on the weight of insulin compound in the formulation |
| Citric acid | 44 mM |
| Glycerol | 174 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.4 | |

Example I

| | |
|---|---|
| Insulin lispro | 1000 U/ml |
| Sodium phosphate | 2 mM |
| phenol | 15.9 mM |
| m-cresol | 15.9 mM |
| Ionic zinc (as $ZnCl_2$) | 197 µg/ml (3 mM), equals 0.55% (w/w) based on the weight of insulin compound in the formulation |
| Citric acid | 44 mM |
| Glycerol | 174 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.4 | |

Example J

| | |
|---|---|
| Insulin glulisine | 1000 U/ml |
| Sodium phosphate | 2 mM |
| phenol | 15.9 mM |
| m-cresol | 15.9 mM |
| Ionic zinc (as $ZnCl_2$) | 197 µg/ml (3 mM), equals 0.55% (w/w) based on the weight of insulin compound in the formulation |
| Citric acid | 44 mM |
| Glycerol | 174 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.4 | |

Example K

| | |
|---|---|
| Insulin aspart | 1000 U/ml |
| Sodium phosphate | 2 mM |
| phenol | 15.9 mM |
| m-cresol | 15.9 mM |
| Ionic zinc (as $ZnCl_2$) | 197 µg/ml (3 mM), equals 0.55% (w/w) based on the weight of insulin compound in the formulation |
| Citric acid | 44 mM |
| Glycerol | 174 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.8 | |

Example L

| | |
|---|---|
| Insulin lispro | 1000 U/ml |
| Sodium phosphate | 2 mM |
| phenol | 15.9 mM |
| m-cresol | 15.9 mM |
| Ionic zinc (as $ZnCl_2$) | 197 µg/ml (3 mM), equals 0.55% (w/w) based on the weight of insulin compound in the formulation |
| Citric acid | 44 mM |
| Glycerol | 174 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.8 | |

Example M

| | |
|---|---|
| Insulin glulisine | 1000 U/ml |
| Sodium phosphate | 2 mM |
| phenol | 15.9 mM |
| m-cresol | 15.9 mM |
| Ionic zinc (as $ZnCl_2$) | 197 µg/ml (3 mM), equals 0.55% (w/w) based on the weight of insulin compound in the formulation |
| Citric acid | 44 mM |
| Glycerol | 174 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.8 | |

Example N

| | |
|---|---|
| Insulin lispro | 100 U/ml |
| Sodium phosphate | 2 mM |
| phenol | 15.9 mM |
| m-cresol | 15.9 mM |
| Ionic zinc (as $ZnCl_2$) | 19.7 µg/ml (0.3 mM), equals 0.55% (w/w) based on the weight of insulin compound in the formulation |
| TETA | 0.5 mM |
| Glycerol | 174 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.4 | |

Example O

| | |
|---|---|
| Insulin aspart | 100 U/ml |
| Sodium phosphate | 2 mM |
| phenol | 15.9 mM |
| m-cresol | 15.9 mM |
| Ionic zinc (as $ZnCl_2$) | 19.7 µg/ml (0.3 mM), equals 0.55% (w/w) based on the weight of insulin compound in the formulation |
| TETA | 0.5 mM |
| NaCl | 150 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.4 | |

Example P

| | |
|---|---|
| Insulin aspart | 1000 U/ml |
| Sodium phosphate | 2 mM |
| phenol | 15.9 mM |
| m-cresol | 15.9 mM |
| Ionic zinc (as $ZnCl_2$) | 197 µg/ml (3 mM), equals 0.55% (w/w) based on the weight of insulin compound in the formulation |
| TETA | 5 mM |
| Glycerol | 174 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.4 | |

Example Q

| | |
|---|---|
| Insulin lispro | 100 U/ml |
| Sodium phosphate | 2 mM |
| phenol | 15.9 mM |
| m-cresol | 15.9 mM |
| Ionic zinc (as $ZnCl_2$) | 19.7 µg/ml (0.3 mM), equals 0.55% (w/w) based on the weight of insulin compound in the formulation |
| TETA | 0.5 mM |
| Glycerol | 174 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.8 | |

Example R

| | |
|---|---|
| Insulin aspart | 100 U/ml |
| Sodium phosphate | 2 mM |
| phenol | 15.9 mM |
| m-cresol | 15.9 mM |
| Ionic zinc (as $ZnCl_2$) | 19.7 µg/ml (0.3 mM), equals 0.55% (w/w) based on the weight of insulin compound in the formulation |
| TETA | 0.5 mM |
| NaCl | 150 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.8 | |

Example S

| | |
|---|---|
| Insulin aspart | 1000 U/ml |
| Sodium phosphate | 2 mM |
| phenol | 15.9 mM |
| m-cresol | 15.9 mM |
| Ionic zinc (as $ZnCl_2$) | 197 µg/ml (3 mM), equals 0.55% (w/w) based on the weight of insulin compound in the formulation |
| TETA | 5 mM |
| Glycerol | 174 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.8 | |

Example T

| | |
|---|---|
| Insulin lispro | 100 U/ml |
| Sodium phosphate | 2 mM |
| phenol | 15.9 mM |
| m-cresol | 15.9 mM |
| Ionic zinc (as $ZnCl_2$) | 19.7 µg/ml (0.3 mM), equals 0.55% (w/w) based on the weight of insulin compound in the formulation |
| DETA | 5 mM |
| Glycerol | 174 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.4 | |

Example U

| | |
|---|---|
| Insulin aspart | 100 U/ml |
| Sodium phosphate | 2 mM |
| phenol | 15.9 mM |
| m-cresol | 15.9 mM |
| Ionic zinc (as ZnCl$_2$) | 19.7 µg/ml (0.3 mM), equals 0.55% (w/w) based on the weight of insulin compound in the formulation |
| DETA | 5 mM |
| NaCl | 150 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.4 | |

Example V

| | |
|---|---|
| Insulin aspart | 1000 U/ml |
| Sodium phosphate | 2 mM |
| phenol | 15.9 mM |
| m-cresol | 15.9 mM |
| Ionic zinc (as ZnCl$_2$) | 197 µg/ml (3 mM), equals 0.55% (w/w) based on the weight of insulin compound in the formulation |
| DETA | 5 mM |
| Glycerol | 174 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.4 | |

Example W

| | |
|---|---|
| Insulin lispro | 100 U/ml |
| Sodium phosphate | 2 mM |
| phenol | 15.9 mM |
| m-cresol | 15.9 mM |
| Ionic zinc (as ZnCl$_2$) | 19.7 µg/ml (0.3 mM), equals 0.55% (w/w) based on the weight of insulin compound in the formulation |
| DETA | 0.5 mM |
| Glycerol | 174 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.8 | |

Example X

| | |
|---|---|
| Insulin aspart | 100 U/ml |
| Sodium phosphate | 2 mM |
| phenol | 15.9 mM |
| m-cresol | 15.9 mM |
| Ionic zinc (as ZnCl$_2$) | 19.7 µg/ml (0.3 mM), equals 0.55% (w/w) based on the weight of insulin compound in the formulation |
| TETA | 0.5 mM |
| NaCl | 150 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.8 | |

Example Y

| | |
|---|---|
| Insulin aspart | 1000 U/ml |
| Sodium phosphate | 2 mM |
| phenol | 15.9 mM |
| m-cresol | 15.9 mM |
| Ionic zinc (as ZnCl$_2$) | 197 µg/ml (3 mM), equals 0.55% (w/w) based on the weight of insulin compound in the formulation |
| TETA | 5 mM |
| Glycerol | 174 mM |
| Surfactant | dodecyl maltoside (0.05 mg/ml) |
| Water for injection | qs |
| Residual NaCl | Acidification and subsequent neutralisation during preparation results in formation of 2-4 mM NaCl |
| pH adjusted to 7.8 | |

Example Z

| | |
|---|---|
| Insulin compound* | 100 U/ml |
| Sodium phosphate | 2 mM |
| phenol | 15.9 mM |
| m-cresol | 15.9 mM |
| Ionic zinc (as ZnCl$_2$) | 19.7 µg/ml (0.3 mM), equals 0.55% (w/w) based on the weight of insulin compound in the formulation |
| Nicotinamide | 80 mM |
| NaCl | 70 mM |
| Dodecyl maltoside | 0.1 mM |
| Water for injection | qs |
| Residual NaCl | Acidification and subsequent neutralisation during preparation results in formation of 2-4 mM NaCl |
| pH adjusted to 7.4 | |

Example AA

| | |
|---|---|
| Insulin compound* | 100 U/ml |
| Sodium phosphate | 2 mM |
| phenol | 15.9 mM |
| m-cresol | 15.9 mM |
| Ionic zinc (as ZnCl$_2$) | 19.7 µg/ml (0.3 mM), equals 0.55% (w/w) based on the weight of insulin compound in the formulation |
| Nicotinamide | 80 mM |
| NaCl | 70 mM |
| Dodecyl maltoside | 0.1 mM |
| Water for injection | qs |
| Residual NaCl | Acidification and subsequent neutralisation during preparation results in formation of 2-4 mM NaCl |
| pH adjusted to 7.8 | |

Example AB

| | |
|---|---|
| Insulin compound* | 1000 U/ml |
| Sodium phosphate | 2 mM |
| phenol | 15.9 mM |
| m-cresol | 15.9 mM |

-continued

| | |
|---|---|
| Ionic zinc (as ZnCl$_2$) | 19.7 µg/ml (0.3 mM), equals 0.55% (w/w) based on the weight of insulin compound in the formulation |
| Nicotinamide | 80 mM |
| NaCl | 70 mM |
| Dodecyl maltoside | 0.05 mM |
| Water for injection | qs |
| Residual NaCl | Acidification and subsequent neutralisation during preparation results in formation of 2-4 mM NaCl |
| pH adjusted to 7.4 | |

Example AC

| | |
|---|---|
| Insulin compound* | 1000 U/ml |
| Sodium phosphate | 2 mM |
| phenol | 15.9 mM |
| m-cresol | 15.9 mM |
| Ionic zinc (as ZnCl$_2$) | 19.7 µg/ml (0.3 mM), equals 0.55% (w/w) based on the weight of insulin compound in the formulation |
| Nicotinamide | 80 mM |
| NaCl | 70 mM |
| Dodecyl maltoside | 0.05 mM |
| Water for injection | qs |
| Residual NaCl | Acidification and subsequent neutralisation during preparation results in formation of 2-4 mM NaCl |
| pH adjusted to 7.8 | |

Example AD

| | |
|---|---|
| Insulin compound* | 100 U/ml |
| Sodium phosphate | 2 mM |
| phenol | 15.9 mM |
| m-cresol | 15.9 mM |
| Ionic zinc (as ZnCl$_2$) | 19.7 µg/ml (0.3 mM), equals 0.55% (w/w) based on the weight of insulin compound in the formulation |
| Nicotinamide | 80 mM |
| Citric acid | 22 mM |
| Glycerol | 70 mM |
| Dodecyl maltoside | 0.1 mM |
| Water for injection | qs |
| Residual NaCl | Acidification and subsequent neutralisation during preparation results in formation of 2-4 mM NaCl |
| pH adjusted to 7.4 | |

Examples Z and AA to AD: * Insulin compound = insulin aspart or insulin lispro or insulin glulisine or recombinant human insulin Example E

| | |
|---|---|
| Insulin aspart | 100 U/ml |
| Sodium phosphate | 2 mM |
| phenol | 15.9 mM |
| m-cresol | 15.9 mM |
| Ionic zinc (as ZnCl$_2$) | 19.7 µg/ml (0.3 mM), equals 0.55% (w/w) based on the weight of insulin compound in the formulation |
| Citrate | 22 mM |
| NaCl | 150 mM |
| EDTA | 0.1 mM |
| Dodecyl maltoside | 0.05 mg/ml |
| Water for injection | qs |
| Residual NaCl | Acidification and subsequent neutralisation during preparation results in formation of 2-4 mM NaCl |
| pH adjusted to 7.4 | |

Example AF

| | |
|---|---|
| Insulin lispro | 100 U/ml |
| Sodium phosphate | 2 mM |
| phenol | 15.9 mM |
| m-cresol | 15.9 mM |
| Ionic zinc (as ZnCl$_2$) | 19.7 µg/ml (0.3 mM), equals 0.55% (w/w) based on the weight of insulin compound in the formulation |
| Citrate | 22 mM |
| Glycerol | 174 mM |
| EDTA | 0.1 mM |
| Dodecyl maltoside | 0.05 mg/ml |
| Water for injection | qs |
| Residual NaCl | Acidification and subsequent neutralisation during preparation results in formation of 2-4 mM NaCl |
| pH adjusted to 7.4 | |

Example AG

| | |
|---|---|
| Insulin aspart | 100 U/ml |
| Sodium phosphate | 2 mM |
| phenol | 15.9 mM |
| m-cresol | 15.9 mM |
| Ionic zinc (as ZnCl$_2$) | 19.7 µg/ml (0.3 mM), equals 0.55% (w/w) based on the weight of insulin compound in the formulation |
| Citrate | 22 mM |
| NaCl | 150 mM |
| EDTA | 0.02 mM |
| Dodecyl maltoside | 0.05 mg/ml |
| Water for injection | qs |
| Residual NaCl | Acidification and subsequent neutralisation during preparation results in formation of 2-4 mM NaCl |
| pH adjusted to 7.4 | |

Example AH

| | |
|---|---|
| Insulin lispro | 100 U/ml |
| Sodium phosphate | 2 mM |
| phenol | 15.9 mM |
| m-cresol | 15.9 mM |
| Ionic zinc (as ZnCl$_2$) | 19.7 µg/ml (0.3 mM), equals 0.55% (w/w) based on the weight of insulin compound in the formulation |
| Citrate | 22 mM |
| Glycerol | 174 mM |
| EDTA | 0.02 mM |
| Dodecyl maltoside | 0.05 mg/ml |
| Water for injection | qs |
| Residual NaCl | Acidification and subsequent neutralisation during preparation results in formation of 2-4 mM NaCl |
| pH adjusted to 7.4 | |

Example AI

| | |
|---|---|
| Insulin aspart | 1000 U/ml |
| Sodium phosphate | 2 mM |
| phenol | 15.9 mM |
| m-cresol | 15.9 mM |
| Ionic zinc (as ZnCl$_2$) | 19.7 µg/ml (0.3 mM), equals 0.55% (w/w) based on the weight of insulin compound in the formulation |
| Citrate | 44 mM |
| Glycerol | 174 mM |
| EDTA | 0.1 mM |
| Dodecyl maltoside | 0.05 mg/ml |
| Water for injection | qs |

Example AJ

| | |
|---|---|
| Insulin lispro | 1000 U/ml |
| Sodium phosphate | 2 mM |
| phenol | 15.9 mM |
| m-cresol | 15.9 mM |
| Ionic zinc (as $ZnCl_2$) | 19.7 µg/ml (0.3 mM), equals 0.55% (w/w) based on the weight of insulin compound in the formulation |
| Citrate | 44 mM |
| Glycerol | 174 mM |
| EDTA | 0.1 mM |
| Dodecyl maltoside | 0.05 mg/ml |
| Water for injection | qs |
| Residual NaCl | Acidification and subsequent neutralisation during preparation results in formation of 2-4 mM NaCl |
| pH adjusted to 7.4 | |

Example AK

| | |
|---|---|
| Insulin aspart | 100 U/ml |
| Sodium phosphate | 2 mM |
| phenol | 15.9 mM |
| m-cresol | 15.9 mM |
| Ionic zinc (as $ZnCl_2$) | 19.7 µg/ml (0.3 mM), equals 0.55% (w/w) based on the weight of insulin compound in the formulation |
| Citrate | 22 mM |
| NaCl | 150 mM |
| EDTA | 0.1 mM |
| Dodecyl maltoside | 0.05 mg/ml |
| Water for injection | qs |
| Residual NaCl | Acidification and subsequent neutralisation during preparation results in formation of 2-4 mM NaCl |
| pH adjusted to 7.8 | |

Example AL

| | |
|---|---|
| Insulin lispro | 100 U/ml |
| Sodium phosphate | 2 mM |
| phenol | 15.9 mM |
| m-cresol | 15.9 mM |
| Ionic zinc (as $ZnCl_2$) | 19.7 µg/ml (0.3 mM), equals 0.55% (w/w) based on the weight of insulin compound in the formulation |
| Citrate | 22 mM |
| Glycerol | 174 mM |
| EDTA | 0.1 mM |
| Dodecyl maltoside | 0.05 mg/ml |
| Water for injection | qs |
| Residual NaCl | Acidification and subsequent neutralisation during preparation results in formation of 2-4 mM NaCl |
| pH adjusted to 7.8 | |

Example AM

| | |
|---|---|
| Insulin aspart | 100 U/ml |
| Sodium phosphate | 2 mM |
| phenol | 15.9 mM |
| m-cresol | 15.9 mM |
| Ionic zinc (as $ZnCl_2$) | 19.7 µg/ml (0.3 mM), equals 0.55% (w/w) based on the weight of insulin compound in the formulation |
| Citrate | 22 mM |
| NaCl | 150 mM |
| EDTA | 0.02 mM |
| Dodecyl maltoside | 0.05 mg/ml |
| Water for injection | qs |
| Residual NaCl | Acidification and subsequent neutralisation during preparation results in formation of 2-4 mM NaCl |
| pH adjusted to 7.8 | |

Example AN

| | |
|---|---|
| Insulin lispro | 100 U/ml |
| Sodium phosphate | 2 mM |
| phenol | 15.9 mM |
| m-cresol | 15.9 mM |
| Ionic zinc (as $ZnCl_2$) | 19.7 µg/ml (0.3 mM), equals 0.55% (w/w) based on the weight of insulin compound in the formulation |
| Citrate | 22 mM |
| Glycerol | 174 mM |
| EDTA | 0.02 mM |
| Dodecyl maltoside | 0.05 mg/ml |
| Water for injection | qs |
| Residual NaCl | Acidification and subsequent neutralisation during preparation results in formation of 2-4 mM NaCl |
| pH adjusted to 7.8 | |

Example AO

| | |
|---|---|
| Insulin aspart | 1000 U/ml |
| Sodium phosphate | 2 mM |
| phenol | 15.9 mM |
| m-cresol | 15.9 mM |
| Ionic zinc (as $ZnCl_2$) | 19.7 µg/ml (0.3 mM), equals 0.55% (w/w) based on the weight of insulin compound in the formulation |
| Citrate | 44 mM |
| Glycerol | 174 mM |
| EDTA | 0.1 mM |
| Dodecyl maltoside | 0.05 mg/ml |
| Water for injection | qs |
| Residual NaCl | Acidification and subsequent neutralisation during preparation results in formation of 2-4 mM NaCl |
| pH adjusted to 7.8 | |

Example AP

| | |
|---|---|
| Insulin lispro | 1000 U/ml |
| Sodium phosphate | 2 mM |
| phenol | 15.9 mM |
| m-cresol | 15.9 mM |
| Ionic zinc (as $ZnCl_2$) | 19.7 µg/ml (0.3 mM), equals 0.55% (w/w) based on the weight of insulin compound in the formulation |
| Citrate | 44 mM |
| Glycerol | 174 mM |
| EDTA | 0.1 mM |
| Dodecyl maltoside | 0.05 mg/ml |
| Water for injection | qs |
| Residual NaCl | Acidification and subsequent neutralisation during preparation results in formation of 2-4 mM NaCl |
| pH adjusted to 7.8 | |

Method for Preparation for the Above Formulations:

Insulin powder is added to water and HCl is added until the powder is fully dissolved (pH has to be <3 in order to achieve full dissolution). $ZnCl_2$ is added to the required level. Once dissolved, pH is adjusted to approximately 7 and volume is adjusted with water so that the insulin concentration is 2× the required concentration. The composition is then mixed 1:1 (v/v) with a mixture of additional excipients (all at 2× the required concentration).

Example 2—Stability of Insulin Aspart Formulations of the Invention in the Presence of Citrate The effect of citrate on stability of insulin aspart was investigated. In addition, it was investigated in this experiment how various surfactants influence the effect of citrate on insulin aspart stability. The effects were investigated both in the presence of NaCl and in the presence of glycerol as tonicity modifiers. Stability of insulin aspart was assessed by:

Visual Assessment (as described in General Methods using Visual Assessment Scoring Method A)

SEC (formation of soluble aggregates, as described in General Methods)

TABLE 1

Stability of insulin aspart assessed using Visual Assessment Scoring Method A following storage at 30° C. for 4 and 8 weeks.

| Additive(s) | Visual assessment (0 weeks) | Visual assessment (4 weeks) | Visual assessment (8 weeks) |
| --- | --- | --- | --- |
| None | 1 | 1 | 1 |
| Citrate (22 mM) | 1 | 2 | 3 |
| Citrate (22 mM) + TWEEN ® 20 (0.05 mg/ml) | 1 | 2 | 2 |
| Citrate (22 mM) + dodecyl maltoside (0.05 mg/ml) | 1 | 1 | 1 |

All formulations contained insulin aspart (100 U/ml), sodium phosphate (2 mM), phenol (15.9 mM), m-cresol (15.9 mM), NaCl (150 mM) and 19.7 µg/ml zinc (0.55% (w/w) based on the weight of insulin compound in the formulation, as $ZnCl_2$) and were adjusted to pH 7.4.

Extent of visible precipitation is graded on a scale 1-3; 1 = clear solution free of visible particles; 2 = slight particle formation, 3 = more significant precipitation.

TABLE 2

Stability of insulin aspart assessed by SEC following storage at 30° C. for 4 and 8 weeks.

| Additive | SEC main peak (%) (0 weeks) | SEC main peak (%) (4 weeks) | SEC main peak (%) (8 weeks) |
| --- | --- | --- | --- |
| None | 99.83 | 99.62 | 99.43 |
| Citrate (22 mM) | 99.82 | 99.50 | 99.22 |
| Citrate (22 mM) + TWEEN ® 20 (0.05 mg/ml) | 99.82 | 99.51 | 99.27 |
| Citrate (22 mM) + dodecyl maltoside (0.05 mg/ml) | 99.82 | 99.71 | 99.55 |

All formulations contained insulin aspart (100 U/ml), sodium phosphate (2 mM), phenol (15.9 mM), m-cresol (15.9 mM), NaCl (150 mM) and 19.7 µg/ml zinc (0.55% (w/w) based on the weight of insulin compound in the formulation, as $ZnCl_2$) and were adjusted to pH 7.4.

TABLE 3

Stability of insulin aspart assessed using Visual Assessment Scoring Method A following storage at 30° C. for 4 and 8 weeks.

| Additive(s) | Visual assessment (0 weeks) | Visual assessment (4 weeks) | Visual assessment (8 weeks) |
| --- | --- | --- | --- |
| None | 1 | 1 | 1 |
| Citrate (22 mM) | 1 | 3 | 3 |
| Citrate (22 mM) + TWEEN ® 20 (0.05 mg/ml mM) | 1 | 2 | 3 |
| Citrate (22 mM) + dodecyl maltoside (0.05 mg/ml) | 1 | 1 | 1 |

All formulations contained insulin aspart (100 U/ml), sodium phosphate (2 mM), phenol (15.9 mM), m-cresol (15.9 mM), glycerol (174 mM) and 19.7 µg/ml zinc (0.55% (w/w) based on the weight of insulin compound in the formulation, as $ZnCl_2$) and were adjusted to pH 7.4.

Extent of visible precipitation is graded on a scale 1-3; 1 = clear solution free of visible particles; 2 = slight particle formation, 3 = more significant precipitation.

TABLE 4

Stability of insulin aspart assessed by SEC following storage at 30° C. for 4 and 8 weeks.

| Additive | SEC main peak (%) (0 weeks) | SEC main peak (%) (4 weeks) | SEC main peak (%) (8 weeks) |
| --- | --- | --- | --- |
| None | 99.82 | 99.69 | 99.48 |
| Citrate (22 mM) | 99.80 | 98.58 | 97.43 |
| Citrate (22 mM) + TWEEN ® 20 (0.05 mg/ml) | 99.80 | 98.59 | 97.86 |
| Citrate (22 mM) + dodecyl maltoside (0.1 mg/ml) | 99.80 | 98.99 | 98.24 |

All formulations contained insulin aspart (100 U/ml), sodium phosphate (2 mM), phenol (15.9 mM), m-cresol (15.9 mM), glycerol (174 mM) and 19.7 µg/ml zinc (0.55% (w/w) based on the weight of insulin compound in the formulation, as $ZnCl_2$) and were adjusted to pH 7.4.

Using NaCl as a tonicity modifier, it was shown (Tables 1 and 2) that addition of citrate (22 mM) to the composition of insulin aspart resulted in impairment of insulin aspart stability, particularly with respect to formation of visible particles. Clear formation of particles was observed after 4 weeks incubation at 30° C., and a more significant precipitation was observed after 8 weeks. Addition of citrate also had a slight negative impact on the formation of soluble aggregates (expressed as retention of main peak on SEC chromatogram in Table 2). The detrimental effect of citrate appeared to be completely reversed in the presence of dodecyl maltoside. Some improvement was also observed in the presence of TWEEN® 20, but the effect was not as clear as in the case of dodecyl maltoside. Clear particle formation was still observed following 8 weeks incubation at 30° C. in the presence of TWEEN® 20.

Using glycerol as a tonicity modifier (Tables 3 and 4), similar effects of citrate and surfactants were also observed. However, in this case the destabilization of insulin aspart by citrate was more significant. Whilst a stabilizing effect of dodecyl maltoside was also observed, particularly with respect to visual assessment, the overall stability was worse than in corresponding compositions in the presence of NaCl. Thus, at 100 U/ml of insulin aspart, low ionic strength formulations may be less stable than higher ionic strength formulations. TWEEN® 20 also had a mild stabilising effect, but it was not as significant as that of dodecyl maltoside.

Example 3—Stability of Insulin Aspart Formulations in the Presence of TETA and EDTA The effect TETA and EDTA on stability of insulin aspart was investigated. The stability was compared to that of the ultra-rapid acting formulation disclosed in WO2010/149772 (Formulation K in Example 1 of WO2010/149772). All formulations tested comprised insulin aspart (100 U/ml), phenol (16 mM), m-cresol (16 mM), and zinc (from $ZnCl_2$, 19.7 µg/ml with respect to zinc=0.3 mM) and were adjusted to pH 7.4. The additional components of each formulation are listed in Table 5.

TABLE 5

Additional components in formulations of insulin aspart tested.

| Formulation | Na phosphate (mM) | TRIS (mM) | NaCl (mM) | Glycerol (mM) | EDTA (mM) | TETA (mM) | Nicotinamide (mM) | Arginine (mM) | Dodecyl maltoside (mg/ml) |
|---|---|---|---|---|---|---|---|---|---|
| 3A NOVORAPID ® control | 13.2 | | 10 | 174 | | | | | |
| 3B (= Formulation K in WO2010/149772) | | 7 | 10 | 83.6 | | | 80 | 30 | |
| 3C | 2 | | 150 | | 0.5 | | | | |
| 3D | 2 | | 150 | | 2 | | | | |
| 3E | 2 | | 150 | | 0.5 | | | | 0.05 |
| 3F | 2 | | 150 | | 2 | | | | 0.05 |
| 3G | 2 | | 150 | | | 0.5 | | | |
| 3H | 2 | | 150 | | | 2 | | | |
| 3I | 2 | | 150 | | | 0.5 | | | 0.05 |
| 3J | 2 | | 150 | | | 2 | | | 0.05 |

Stability of insulin aspart was tested using the Visual Assessment Scoring Method B, as described in General Methods. Results are shown in Table 6. The composition of NOVORAPID® remained clear and particle-free following 4 weeks storage at 30° C. The nicotinamide-based composition (Formulation K in Example 1 of WO2010/149772) also showed good stability over 4 weeks at 30° C., although slight particle formation was observed at the 4 week time-point. Significant precipitation was observed in the EDTA-based formulations. Whilst the presence of dodecyl maltoside appeared to delay the precipitation, significant particle formation was still observed at the 4 week time-point. Slow precipitation was also observed in the TETA-based formulation. However, in the presence of dodecyl maltoside, the TETA-based formulations remained clear and particle-free following 4 weeks storage at 30° C.

TABLE 6

Visual scores of insulin aspart compositions using Visual Assessment Scoring Method B following storage at 30° C.

| | 0 weeks | 1 week | 2 weeks | 4 weeks |
|---|---|---|---|---|
| Formulation 3A (NOVORAPID ® control) | 1 | 1 | 1 | 1 |
| Formulation 3B (= Formulation K in WO2010/149772) | 1 | 1 | 1 | 2 |
| Formulation 3C | 1 | 3 | 4 | 5 |
| Formulation 3D | 1 | 4 | 5 | 5 |
| Formulation 3E | 1 | 1 | 3 | 4 |
| Formulation 3F | 1 | 3 | 4 | 5 |
| Formulation 3G | 1 | 1 | 2 | 3 |
| Formulation 3H | 1 | 2 | 3 | 5 |
| Formulation 3I | 1 | 1 | 1 | 1 |
| Formulation 3J | 1 | 1 | 1 | 1 |

Visual score 1: clear solution, virtually free of particles; visual score 2: ~5 very small particles; visual score 3: ~10-20 very small particles; visual score 4: 20-50 particles, including larger particles; visual score 5: >50 particles, including larger particles.

Example 4—Comparison of Pharmacodynamic Profiles of Insulin Aspart Formulations in the Presence of (a) TETA, (b) EDTA and (c) Nicotinamide Pharmacodynamic profile of the following compositions was tested using the Diabetic Pig Pharmacokinetic/Pharmacodynamic Model (see General Methods (c)):

Formulation 4A: insulin aspart (100 U/ml), NaCl (10 mM), TRIS (7 mM), glycerol (83.6 mM), arginine (30 mM), nicotinamide (80 mM), phenol (16 mM), m-cresol (16 mM), zinc (from $ZnCl_2$, 19.7 µg/ml with respect to zinc), pH 7.4

Formulation 4B: insulin aspart (100 U/ml), NaCl (150 mM), sodium phosphate (2 mM), EDTA (0.5 mM), dodecyl maltoside (0.05 mg/ml), phenol (16 mM), m-cresol (16 mM), zinc (from $ZnCl_2$, 19.7 µg/ml with respect to zinc), pH 7.4

Formulation 4C: insulin aspart (100 U/ml), NaCl (150 mM), sodium phosphate (2 mM), TETA (0.5 mM), dodecyl maltoside (0.05 mg/ml), phenol (16 mM), m-cresol (16 mM), zinc (from $ZnCl_2$, 19.7 µg/ml with respect to zinc), pH 7.4

Formulation 4A is identical to Formulation K in Example 1 of WO2010/149772, which was shown to have a significantly more rapid onset of action compared with that of commercially available NOVORAPID® product (Formulation A in Example 1 of WO2010/149772)—see FIGS. 4 and 5 of WO2010/149772. Formulations 4A, 4B and 4C are also the same as Formulations 3B, 3E and 3I, respectively, referred to in Example 3 of the present application. Results are shown in FIG. 1. It was shown that the formulation comprising TETA (Formulation 4C) resulted in a comparable PD profile to that of the composition comprising nicotinamide (Formulation 4A). The decline in glucose concentration appeared to be slightly more rapid in the TETA-based formulation in the first 50 minutes after injection, but it appeared to slow down beyond that point.

Formulation comprising EDTA (Formulation 4B) resulted in a more rapid glucose decrease compared with both the TETA-based and the nicotinamide-based formulation. However, as shown in Example 3, this formulation is unstable and therefore not suitable for a viable pharmaceutical product.

Example 5—Effect of pH and the Source of Citrate on Stability of Insulin Aspart

The stability of insulin aspart (100 U/ml) in the formulation of currently marketed NOVORAPID® rapid-acting product (formulation 5A in Table 7) was compared with that of insulin aspart in a number of compositions comprising dodecyl maltoside and either trisodium citrate or citric acid (formulations 5B-5I in Table 7) following storage at 37° C. and 30° C.

The formulations were prepared as follows:
Insulin powder was added to water and HCl was added until the powder was fully dissolved (pH has to be <3 in order to achieve full dissolution). $ZnCl_2$ was added to the required level. Once $ZnCl_2$ was fully dissolved, pH was adjusted to approximately 7 and volume was adjusted with deionised water so that the insulin concentration was 200 U/ml. Separately, a background solution was prepared for each of the formulations tested containing all of the required excipients at 2× the required concentration. Each background solution was then adjusted to the required level. For example, the background solution for formulation 5B contained 4 mM sodium phosphate, 300 mM sodium chloride, 0.1 mg/ml dodecyl maltoside, 44 mM trisodium citrate and was adjusted to pH 7.0. Similarly, the background solution for formulation 5H contained 4 mM sodium phosphate, 300 mM sodium chloride, 0.1 mg/ml dodecyl maltoside, 44 mM citric acid and was adjusted to pH 7.8. Formulations 5A-5I were then prepared by mixing 1 part (v/v) of the 200 U/ml insulin solution with 1 part (v/v) of the background solution. The pH of each composition was subsequently checked to ensure it was at the correct level.

TABLE 7

Compositions of formulations (5A-5I) of insulin aspart tested. All formulations contained insulin aspart (100 U/ml), zinc (0.3 mM), phenol (16 mM) and m-cresol (16 mM) and were adjusted to the required pH by either sodium hydroxide or hydrochloric acid.

| | Sodium phosphate (mM) | Sodium chloride (mM) | Glycerol (mM) | Dodecyl maltoside (mg/ml) | Triodium citrate (mM) | Citric acid (mM) | pH |
|---|---|---|---|---|---|---|---|
| 5A | 7 | 10 | 174 | | | | 7.4 |
| 5B | 2 | 150 | | 0.05 | 22 | | 7.0 |
| 5C | 2 | 150 | | 0.05 | 22 | | 7.4 |
| 5D | 2 | 150 | | 0.05 | 22 | | 7.8 |
| 5E | 2 | 150 | | 0.05 | 22 | | 8.0 |
| 5F | 2 | 150 | | 0.05 | | 22 | 7.0 |
| 5G | 2 | 150 | | 0.05 | | 22 | 7.4 |
| 5H | 2 | 150 | | 0.05 | | 22 | 7.8 |
| 5I | 2 | 150 | | 0.05 | | 22 | 8.0 |

Results of the visual assessment (using Visual Assessment Scoring Method B) and the formation of related species (by RP-HPLC) of formulations 5A-5I are shown in Table 8. It was shown that in the presence of trisodium citrate there was a significant particle formation at pH 7.0 and 7.4 at 37° C. (accelerated storage temperature). The rate of particle formation was considerably lower at higher pH levels, particularly at pH 7.8. A similar trend was observed at 30° C. where pH 7.8 also appeared to be optimal. The use of citric acid instead of trisodium citrate resulted in lower particle formation across the whole pH range. The rate of particle formation at pH 7.8, both using citric acid and using trisodium citrate, was in fact lower than that in the formulation of the currently marketed NOVORAPID® product. Whilst at pH 7.8 there was minimal difference between the use of trisodium citrate and citric acid, use of citric acid appears preferable to ensure safety of the product, because small variability around the target pH of the product is expected by the regulatory authorities and citric acid would thus ensure lower particle formation in case the product was formulated slightly below the target pH during manufacturing.

Whilst a slight increase in the rate of related species formation was observed with increasing pH of the formulation, the use of citric acid also resulted in lower rate of related species formation compared with corresponding formulations based on trisodium citrate, further highlighting the benefit of using citric acid. Importantly, the composition based on citric acid at pH 7.8 showed better stability than the formulation of the currently marketed NOVORAPID® product in every respect.

TABLE 8

Visual scores and formation of related species of insulin aspart formulations 5A-5I using Visual Assessment Scoring Method B following storage at 37° C. and 30° C. for 4 weeks.

| | Visual score (0 weeks) | Visual score (37° C., 4 weeks) | Visual score (30° C., 4 weeks) | Increase in % related species (37° C., 4 weeks) | Increase in % related species (30° C., 4 weeks) |
|---|---|---|---|---|---|
| 5A | 1 | 4 | 2 | 8.47 | 3.06 |
| 5B | 1 | 5 | 5 | Not analysed* | Not analysed* |
| 5C | 1 | 5 | 2 | Not analysed* | 2.50 |
| 5D | 1 | 2 | 1 | 8.71 | 2.99 |
| 5E | 1 | 3 | 2 | 8.88 | 3.09 |
| 5F | 1 | 3 | 2 | 5.94 | 2.24 |
| 5G | 1 | 2 | 2 | 6.23 | 2.37 |
| 5H | 1 | 2 | 1 | 6.72 | 2.54 |
| 5I | 1 | 3 | 1 | 8.34 | 3.08 |

*Sample not analysed due to excessive precipitation.
Visual score 1: clear solution, virtually free of particles; visual score 2: ~5 very small particles; visual score 3: ~10-20 very small particles; visual score 4: 20-50 particles, including larger particles; visual score 5: >50 particles, including larger particles.

Example 6—Effect of Alkyl Glycosides and Other Non-Ionic Surfactants on the Stability of Insulin Aspart in the Presence of Trisodium Citrate, L-Histidine and Pyrophosphate Stability of insulin aspart (100 U/ml) was investigated in compositions comprising trisodium citrate (22 mM), L-histidine (10 mM) or pyrophosphate (5 mM), both in the presence and in the absence of alkyl glycosides and other selected non-ionic surfactants. All compositions tested further comprised sodium chloride (150 mM), phenol (15.9 mM), m-cresol (15.9 mM), sodium phosphate (2 mM), ionic zinc (19.7 µg/ml, excluding counter-anion, as $ZnCl_2$) and were adjusted to pH 7.4.

It was shown (Table 9) that the presence of trisodium citrate, L-histidine or pyrophosphate increased considerably the rate of particle formation in formulations of insulin aspart, using the Visual Assessment Scoring Method B. The presence of alkyl glycosides, particularly dodecylmaltoside, appeared to mitigate the increase in particle formation rate. Polysorbate 80 also showed a stabilising effect, although not as significant an effect as dodecyl maltoside. The ability of poloxamer 188 to mitigate the increase in particle formation rate was shown to be worse than that of the other non-ionic surfactants tested. Polysorbate 20 was not effective at all in this experiment.

TABLE 9

Visual scores of insulin aspart (100 U/ml) formulations using Visual Assessment Scoring Method B following storage at 30° C.

| Accelerator | Surfactant (all at 50 µg/ml) | 0 days | 4 days | 7 days | 14 days | 28 days |
|---|---|---|---|---|---|---|
| None | None | 1 | 1 | 1 | 1 | 1 |
| Trisodium citrate (22 mM) | None | 1 | 3 | 4 | 5 | 5 |
| Trisodium citrate (22 mM) | Polysorbate 80 | 1 | 1 | 3 | 3 | 3 |
| Trisodium citrate (22 mM) | Polysorbate 20 | 1 | 3 | 4 | 5 | 5 |
| Trisodium citrate (22 mM) | Poloxamer 188 | 1 | 2 | 4 | 5 | 5 |
| Trisodium citrate (22 mM) | Dodecyl maltoside | 1 | 1 | 1 | 1 | 1 |
| Trisodium citrate (22 mM) | Decyl glucopyranoside | 1 | 1 | 3 | 3 | 4 |
| L-Histidine (10 mM) | None | 1 | 4 | 5 | 5 | 5 |
| L-Histidine (10 mM) | Polysorbate 80 | 1 | 4 | 4 | 4 | 5 |
| L-Histidine (10 mM) | Polysorbate 20 | 1 | 4 | 5 | 5 | 5 |
| L-Histidine (10 mM) | Poloxamer 188 | 1 | 4 | 4 | 5 | 5 |
| L-Histidine (10 mM) | Dodecyl maltoside | 1 | 2 | 2 | 2 | 3 |
| L-Histidine (10 mM) | Decyl glucopyranoside | 1 | 3 | 4 | 4 | 4 |
| Pyrophosphate (5 mM) | None | 1 | 5 | 5 | 5 | 5 |
| Pyrophosphate (5 mM) | Polysorbate 80 | 1 | 4 | 5 | 5 | 5 |
| Pyrophosphate (5 mM) | Polysorbate 20 | 1 | 5 | 5 | 5 | 5 |
| Pyrophosphate (5 mM) | Poloxamer 188 | 1 | 5 | 5 | 5 | 5 |
| Pyrophosphate (5 mM) | Dodecyl maltoside | 1 | 1 | 1 | 2 | 2 |
| Pyrophosphate (5 mM) | Decyl glucopyranoside | 1 | 2 | 4 | 5 | 5 |

Example 7—Effect of Dodecyl Maltoside and Other Non-Ionic Surfactants on the Stability of Insulin Lispro in the Presence of Citric Acid Stability of insulin lispro (100 U/ml) was investigated in formulations comprising citric acid (22 mM), both in the presence and in the absence of dodecyl maltoside and other selected non-ionic surfactants. All formulations (except HUMALOG® control, see below) contained: phenol (15.9 mM), m-cresol (15.9 mM), sodium phosphate (2 mM), ionic zinc (19.7 µg/ml, excluding counter-anion, as $ZnCl_2$) and were adjusted to pH 7.8. Formulations contained either glycerol (174 mM) or NaCl (150 mM) as a tonicity modifier.

For comparison, the formulation of the commercial insulin lispro product (HUMALOG®) was also included in the study. This formulation was prepared using the same procedure as that used for all other formulations studied in this experiment and contained the excipients of the commercial HUMALOG® product. The composition of HUMALOG® is: sodium phosphate (13.2 mM), glycerol (174 mM), m-cresol (29 mM), ionic zinc (19.7 µg/ml, excluding counter-ion), adjusted to pH 7.3.

It was shown (Table 10) that the presence of citric acid (22-44 mM) resulted in an increased formation of particles in compositions of insulin ispro in the absence of dodecyl maltoside or other non-ionic surfactants, using the Visual Assessment Scoring Method B. Higher concentrations of citric acid led to higher rate of particle formation. The nature of the tonicity modifier had a minimal impact on the particle formation rate. Thus, whether the formulation is of higher or lower ionic strength does not appear to significantly impact the stability of insulin lispro at a concentration of 100 U/ml. The presence of dodecyl maltoside mitigated the destabilising effect. The destabilising effect was completely reversed by dodecyl maltoside in formulations comprising 22 and 34 mM citric acid. In the formulation comprising 44 mM the effect was almost completely reversed, the particle formation rate being only very slightly higher than in the reference formulation that did not comprise citric acid. The stabilising effect of dodecyl maltoside appeared to be stronger at 50 µg/ml or 100 µg/ml than at 200 µg/ml, indicating there may be an advantage in using lower dodecyl maltoside concentrations. Polysorbate 80 also appeared to mitigate the destabilising effect, although not to the same extent as dodecyl maltoside. The stabilising effects of polysorbate 20 and poloxamer 188 were considerably weaker than those of dodecyl maltoside and polysorbate 80.

TABLE 10

Visual scores of insulin lispro (100 U/ml) formulations using Visual Assessment Scoring Method B following storage at indicated temperatures.

| Citric acid (mM) | Surfactant | Tonicity modifier | T = 0 weeks | 2-8° C. (8 weeks) | 30° C. (4 weeks) | 30° C. (8 weeks) | 37° C. (4 weeks) |
|---|---|---|---|---|---|---|---|
| 0 mM | None | Glycerol (174 mM) | 1 | 1 | 1 | 1 | 2 |
| 0 mM | None | NaCl (150 mM) | 1 | 1 | 1 | 1 | 3 |
| 22 mM | None | Glycerol (174 mM) | 1 | 1 | 4 | 5 | 5 |
| 34 mM | None | Glycerol (174 mM) | 1 | 1 | 5 | 5 | 5 |
| 44 mM | None | Glycerol (174 mM) | 1 | 3 | 5 | 5 | 5 |
| 22 mM | None | NaCl (150 mM) | 1 | 1 | 4 | 5 | 5 |
| 22 mM | Polysorbate 80 (50 µg/ml) | Glycerol (174 mM) | 1 | 1 | 2 | 2 | 3 |
| 22 mM | Polysorbate 20 (50 µg/ml) | Glycerol (174 mM) | 1 | 1 | 3 | 4 | 4 |

TABLE 10-continued

Visual scores of insulin lispro (100 U/ml) formulations using Visual Assessment Scoring Method B following storage at indicated temperatures.

| Citric acid (mM) | Surfactant | Tonicity modifier | T = 0 weeks | 2-8° C. (8 weeks) | 30° C. (4 weeks) | 30° C. (8 weeks) | 37° C. (4 weeks) |
|---|---|---|---|---|---|---|---|
| 22 mM | Poloxamer 188 (50 μg/ml) | Glycerol (174 mM) | 1 | 1 | 4 | 4 | 5 |
| 22 mM | Dodecyl maltoside (50 μg/ml) | Glycerol (174 mM) | 1 | 1 | 1 | 1 | 1 |
| 22 mM | Dodecyl maltoside (100 μg/ml) | Glycerol (174 mM) | 1 | 1 | 1 | 1 | 1 |
| 22 mM | Dodecyl maltoside (200 μg/ml) | Glycerol (174 mM) | 1 | 1 | 1 | 1 | 2 |
| 22 mM | Dodecyl maltoside (100 μg/ml) | NaCl (150 mM) | 1 | 1 | 1 | 1 | 1 |
| 34 mM | Dodecyl maltoside (50 μg/ml) | Glycerol (174 mM) | 1 | 1 | 1 | 1 | 2 |
| 44 mM | Dodecyl maltoside (50 μg/ml) | Glycerol (174 mM) | 1 | 1 | 1 | 2 | 3 |
|  | HUMALOG ® control |  | 1 | 1 | 1 | 1 | 2 |

Example 8—Effect of Dodecyl Maltoside and Polysorbate 80 on the Stability of Insulin Aspart (1000 U/ml) in the Presence of Trisodium Citrate, L-Histidine and Pyrophosphate Stability of insulin aspart (1000 U/ml) was investigated in formulations comprising trisodium citrate (44 mM), L-histidine (22 mM) or pyrophosphate (22 mM), both in the presence and in the absence of dodecyl maltoside or polysorbate 80. All compositions (except control based on NOVORAPID® composition, see below) further comprised phenol (15.9 mM), m-cresol (15.9 mM), sodium phosphate (2 mM), glycerol (174 mM), sodium chloride (10 mM) and ionic zinc (197 μg/ml, excluding counter-anion, as $ZnCl_2$) and were adjusted to pH7.4.

For comparison, a formulation of insulin aspart (1000 U/m) in the composition of the 100 U/ml commercial insulin aspart product (NOVORAPID®) was also included in the study. This formulation was prepared using the same procedure as that used for all other 1000 U/m formulations studied in this experiment and contained the excipients of the commercial NOVORAPID® product. The concentration of ionic zinc was adjusted to ensure the ratio between insulin aspart and ionic zinc was the same as that in the 100 U/ml NOVORAPID® product. The formulation thus comprised sodium phosphate (7 mM), glycerol (174 mM), sodium chloride (10 mM), phenol (15.9 mM), m-cresol (15.9 mM) and ionic zinc (197 μg/ml, excluding counter-anion) and was adjusted to pH 7.4.

It was shown (Table 11) that the presence of trisodium citrate, L-histidine or pyrophosphate resulted in a considerable increase in the rate of particle formation of insulin aspart, using the Visual Assessment Scoring Method B. The presence of dodecyl maltoside mitigated the destabilising effect. Polysorbate 80 also showed a stabilising effect, although not to the same extent as that of dodecyl maltoside.

TABLE 11

Visual scores of insulin aspart (1000 U/ml) formulations using Visual Assessment Scoring Method B following storage at indicated temperatures.

| Accelerator | Surfactant | Ionic strength* (mM) | T = 0 weeks | 2-8° C. (12 weeks) | 30° C. (4 weeks) | 30° C. (12 weeks) | 37° C. (4 weeks) |
|---|---|---|---|---|---|---|---|
| None | None | 24.16 | 1 | 1 | 2 | 2 | 3 |
| Citrate (44 mM) | None | 24.16 | 1 | 2 | 4 | 5 | 5 |
| Citrate (44 mM) | Dodecyl maltoside (50 μg/ml) | 24.16 | 1 | 1 | 1 | 2 | 3 |
| Citrate (44 mM) | Polysorbate 80 (50 μg/ml) | 24.16 | 1 | 2 | 1 | 3 | 5 |
| Histidine (22 mM) | None | 24.16 | 1 | 2 | 4 | 5 | 5 |
| Histidine (22 mM) | Dodecyl maltoside (50 μg/ml) | 24.16 | 1 | 1 | 2 | 3 | 4 |
| Histidine (22 mM) | Polysorbate 80 (50 μg/ml) | 24.16 | 1 | 2 | 4 | 5 | 4 |

TABLE 11-continued

Visual scores of insulin aspart (1000 U/ml) formulations using Visual Assessment Scoring Method B following storage at indicated temperatures.

| Accelerator | Surfactant | Ionic strength* (mM) | T = 0 weeks | 2-8° C. (12 weeks) | 30° C. (4 weeks) | 30° C. (12 weeks) | 37° C. (4 weeks) |
|---|---|---|---|---|---|---|---|
| Pyrophosphate (22 mM) | None | 24.16 | 1 | 3 | 5 | 5 | 5 |
| Pyrophosphate (22 mM) | Dodecyl maltoside (50 µg/ml) | 24.16 | 1 | 1 | 2 | 3 | 4 |
| Pyrophosphate (22 mM) | Polysorbate 80 (50 µg/ml) | 24.16 | 1 | 1 | 4 | 5 | 5 |
| NOVORAPID ® control (formulated at 1000 U/ml) | | 35.83 | 1 | 1 | 2 | 2 | 3 |

*ionic strength calculation takes into account all ions in the formulation except for the zinc binding species (trisodium citrate, L-histidine or pyrophosphate) and the insulin compound using formula I.

Example 9—Effect of NaCl Concentration on the Stability of Insulin Aspart (1000 U/ml) Both in the Presence and in the Absence of Trisodium Citrate/Dodecyl Maltoside Combination The effect of NaCl concentration on the stability of insulin aspart (1000 U/ml) was investigated both in the presence and in the absence of trisodium citrate (44 mM)/dodecyl maltoside (50 µg/ml) combination. All formulations further comprised phenol (15.9 mM), m-cresol (15.9 mM), sodium phosphate (2 mM), ionic zinc (197 µg/ml, excluding counter-anion, as $ZnCl_2$) and were adjusted to pH 7.4.

The formulations comprised either glycerol (174 mM) or NaCl (150 mM) or a mixture of glycerol and NaCl as a tonicity modifier (See Table 12). The concentration of glycerol in the formulations comprising a mixture of glycerol and NaCl was less than 174 mM so that the overall osmolarity of the compositions remained the same as in the compositions comprising glycerol only.

It was shown (Table 12) that the stability of insulin aspart (1000 U/ml) was negatively impacted by the presence of NaCl, both in the absence and in the presence of trisodium citrate (44 mM)/dodecyl maltoside (50 µg/ml) combination. In the absence of the trisodium citrate (44 mM)/dodecyl maltoside (50 µg/ml) combination, the stability was comparable using glycerol (174 mM) and glycerol (154 mM)/NaCl (10 mM) mixture as a tonicity modifier. However, considerable impairment in stability was observed when 150 mM NaCl was used. Interestingly, the impairment was observed only at 2-8° C. where a marked increase in the rate of particle formation was observed in the presence of 150 mM NaCl. The detrimental impact of increasing NaCl concentration on the stability of insulin aspart (1000 U/ml) was also observed in the presence of trisodium citrate (44 mM)/dodecyl maltoside (50 µg/ml) combination. Whilst only a small difference was observed between compositions comprising glycerol (174 mM) and glycerol (154 mM)/NaCl (10 mM) mixture as tonicity modifiers, a composition comprising glycerol (154 mM)/NaCl (50 mM) mixture showed a considerably impaired stability at 2-8° C.

It was thus demonstrated that increasing the ionic strength of the composition of insulin aspart at 1000 U/ml leads to an increased rate of particle formation.

TABLE 12

Visual scores of insulin aspart (1000 U/ml) formulations using Visual Assessment Scoring Method B following storage at indicated temperatures.

| Citrate | Tonicity modifier | Trisodium citrate (mM)/ Dodecyl maltoside (µg/ml) | Ionic strength* (mM) | T = 0 weeks | 2-8° C. (12 weeks) | 30° C. (4 weeks) | 30° C. (12 weeks) | 37° C. (4 weeks) |
|---|---|---|---|---|---|---|---|---|
| 0 mM | Glycerol (174 mM) | 0/0 | 14.16 | 1 | 1 | 1 | 2 | 3 |
| 0 mM | Glycerol (154 mM) + NaCl (10 mM) | 0/0 | 24.16 | 1 | 1 | 2 | 2 | 3 |
| 0 mM | NaCl (150 mM) | 0/0 | 164.16 | 1 | 5 | 2 | 2 | 2 |
| 44 mM | Glycerol (174 mM) | 44/50 | 14.16 | 1 | 1 | 1 | 2 | 3 |
| 44 mM | Glycerol (154 mM) + NaCl (10 mM) | 44/50 | 24.16 | 1 | 1 | 1 | 2 | 3 |
| 44 mM | Glycerol (74 mM) + NaCl (50 mM) | 44/50 | 64.16 | 1 | 5 | 3 | 3 | 5 |

*ionic strength calculation takes into account all ions in the formulation except for the zinc binding species (trisodium citrate) and the insulin compound using formula I.

Example 10: Comparison of the Source of Citrate and the pH of the Formulation on the Stability of Insulin Aspart (1000 U/ml)

The effect of the source of citrate anion and the pH of the formulation on the stability of insulin aspart (1000 U/ml) was investigated. Citric acid and trisodium citrate were compared as the source of the citrate anion. The formulation comprising citric acid was tested at pH 7.8 and the formulation comprising trisodium citrate was tested at pH 7.4. Both formulations further comprised phenol (15.9 mM), m-cresol (15.9 mM), sodium phosphate (2 mM), glycerol (174 mM), dodecyl maltoside (50 µg/ml) and ionic zinc (197 µg/ml, excluding counter-anion, as $ZnCl_2$).

It was shown (Table 13) that the source of citrate and the pH had a minimal impact on the stability of insulin aspart. The formulation comprising citric acid (pH 7.8) appeared to be very slightly more stable at the 8 week time-point at 30° C.

TABLE 13

Visual scores of insulin aspart (1000 U/ml) formulations using Visual Assessment Scoring Method B following storage at indicated temperatures.

| Source of citrate anion | pH | Ionic strength* (mM) | T = 0 weeks | 2-8° C. (8 weeks) | 30° C. (4 weeks) | 30° C. (8 weeks) | 37° C. (4 weeks) |
|---|---|---|---|---|---|---|---|
| Citric acid (44 mM) | 7.8 | 14.84 | 1 | 1 | 1 | 2 | 3 |
| Trisodium citrate (44 mM) | 7.4 | 14.16 | 1 | 1 | 1 | 3 | 3 |

*ionic strength calculation takes into account all ions in the formulation except for the zinc binding species (trisodium citrate, citric acid) and the insulin compound using formula I.

Example 11: Investigation of the Effect of Citric Acid Concentration on the Stability of Insulin Aspart (1000 U/ml) in the Presence of Dodecyl Maltoside The effect of citric acid concentration on the stability of insulin aspart (1000 U/ml) was investigated in the presence of dodecyl maltoside (0.05 mg/ml). All formulations tested further comprised phenol (15.9 mM), m-cresol (15.9 mM), sodium phosphate (2 mM), glycerol (174 mM), dodecyl maltoside (0.05 mg/ml) and ionic zinc (197 µg/ml, excluding counter-anion, as $ZnCl_2$) and were adjusted to pH 7.8.

It was shown (Table 14) that increasing the concentration of citric acid from 0 to 44 mM had only a very small impact on the stability of insulin aspart (1000 U/ml) in the presence of dodecyl maltoside (0.05 mg/ml). No effect was observed at 2-8° C. and 37° C. for the duration of the experiment, and the rate of particle formation was only very slightly higher in the compositions comprising 22, 33 and 44 mM citric acid compared with compositions comprising 0 and 11 mM citric acid at 30° C.

TABLE 14

Visual scores of insulin aspart (1000 U/ml) formulations using Visual Assessment Scoring Method B following storage at indicated temperatures.

| Citric acid | Ionic strength* (mM) | T = 0 weeks | 2-8° C. (8 weeks) | 30° C. (4 weeks) | 30° C. (8 weeks) | 37° C. (4 weeks) |
|---|---|---|---|---|---|---|
| 0 mM | 14.84 | 1 | 1 | 1 | 1 | 3 |
| 11 mM | 14.84 | 1 | 1 | 1 | 1 | 3 |
| 22 mM | 14.84 | 1 | 1 | 1 | 2 | 3 |
| 33 mM | 14.84 | 1 | 1 | 1 | 2 | 3 |
| 44 mM | 14.84 | 1 | 1 | 1 | 2 | 3 |

*ionic strength calculation takes into account all ions in the formulation except for the zinc binding species (citric acid) and the insulin compound using formula I.

Example 12: Investigation of the Optimal Concentration of Dodecyl Maltoside and Polysorbate 80 on the Stability of Insulin Aspart (1000 U/ml) in the Presence of Different Concentrations of Citric Acid The stability of insulin aspart (1000 U/ml) was investigated in the presence of different concentrations of citric acid and different concentrations of either dodecyl maltoside or polysorbate 80. All formulations tested further comprised phenol (15.9 mM), m-cresol (15.9 mM), sodium phosphate (2 mM), glycerol (174 mM) and ionic zinc (197 µg/ml, excluding counter-anion, as $ZnCl_2$) and were adjusted to pH 7.8. Three concentrations of citric acid (44, 66 and 88 mM) and four concentrations of each non-ionic surfactant were tested as well as corresponding surfactant-free compositions.

The rate of particle formation in formulations of insulin aspart (1000 U/ml) was found to be proportional to citric acid concentration in the range between 44 and 88 mM, with the lower citric acid concentration of 44 mM being most suitable (Table 15). Whilst the presence of both dodecyl maltoside and polysorbate 80 led to a reduction in the rate of particle formation, dodecyl maltoside was found more effective in inhibiting the particle formation than polysorbate 80. The lower concentrations of dodecyl maltoside (0.05 and 0.1 mg/ml) appeared to be more effective in inhibiting the particle formation than higher concentrations (0.2 and 0.3 mg/ml). In contrast, in the case of polysorbate 80 it was the higher concentrations (0.3 and 0.5 mg/ml) that showed a greater ability to reduce the particle formation rate than the lower concentrations (0.05 and 0.1 mg/ml).

TABLE 15

Visual scores of insulin aspart (1000 U/ml) formulations using Visual Assessment Scoring Method B following storage at indicated temperatures.

| Citric acid | Dodecyl maltoside (mg/ml) | Polysorbate 80 (mg/ml) | Ionic strength* (mM) | T = 0 weeks | 2-8° C. (8 weeks) | 30° C. (4 weeks) | 30° C. (8 weeks) | 37° C. (4 weeks) |
|---|---|---|---|---|---|---|---|---|
| 44 mM | 0 | 0 | 14.84 | 1 | 3 | 4 | 5 | 5 |
| 44 mM | 0.05 | 0 | 14.84 | 1 | 1 | 1 | 2 | 3 |
| 44 mM | 0.1 | 0 | 14.84 | 1 | 1 | 1 | 2 | 3 |
| 44 mM | 0.2 | 0 | 14.84 | 1 | 1 | 2 | 2 | 4 |
| 44 mM | 0.3 | 0 | 14.84 | 1 | 2 | 2 | 3 | 5 |
| 44 mM | 0 | 0.05 | 14.84 | 1 | 3 | 2 | 3 | 4 |
| 44 mM | 0 | 0.1 | 14.84 | 1 | 2 | 2 | 3 | 4 |
| 44 mM | 0 | 0.3 | 14.84 | 1 | 2 | 2 | 3 | 4 |
| 44 mM | 0 | 0.5 | 14.84 | 1 | 1 | 1 | 3 | 4 |
| 66 mM | 0 | 0 | 14.84 | 1 | 5 | 5 | 5 | 5 |
| 66 mM | 0.05 | 0 | 14.84 | 1 | 2 | 2 | 4 | 4 |
| 66 mM | 0.1 | 0 | 14.84 | 1 | 3 | 2 | 3 | 4 |
| 66 mM | 0.2 | 0 | 14.84 | 1 | 3 | 2 | 5 | 5 |
| 66 mM | 0.3 | 0 | 14.84 | 1 | 4 | 3 | 5 | 5 |
| 66 mM | 0 | 0.05 | 14.84 | 1 | 5 | 4 | 5 | 5 |
| 66 mM | 0 | 0.1 | 14.84 | 1 | 5 | 4 | 5 | 5 |
| 66 mM | 0 | 0.3 | 14.84 | 1 | 4 | 3 | 4 | 4 |
| 66 mM | 0 | 0.5 | 14.84 | 1 | 4 | 4 | 5 | 5 |
| 88 mM | 0 | 0 | 14.84 | 1 | 5 | 5 | 5 | 5 |
| 88 mM | 0.05 | 0 | 14.84 | 1 | 4 | 2 | 4 | 5 |
| 88 mM | 0.1 | 0 | 14.84 | 1 | 5 | 3 | 3 | 5 |
| 88 mM | 0.2 | 0 | 14.84 | 1 | 5 | 4 | 5 | 5 |
| 88 mM | 0.3 | 0 | 14.84 | 1 | 5 | 4 | 5 | 5 |
| 88 mM | 0 | 0.05 | 14.84 | 1 | 5 | 4 | 5 | 5 |
| 88 mM | 0 | 0.1 | 14.84 | 1 | 5 | 4 | 4 | 5 |
| 88 mM | 0 | 0.3 | 14.84 | 1 | 5 | 3 | 4 | 5 |
| 88 mM | 0 | 0.5 | 14.84 | 1 | 5 | 3 | 5 | 5 |

*ionic strength calculation takes into account all ions in the formulation except for the zinc binding species (citric acid) and the insulin compound using formula I.

Example 13—Effect of Trisodium Citrate and Dodecyl Maltoside on the Pharmacodynamic Profile of Insulin Aspart (100 U/ml)

Pharmacodynamic profile of insulin aspart was compared in the following formulations using the Diabetic Pig Pharmacokinetic/Pharmacodynamic Model (see General Methods (c)):
Insulin aspart (100 U/ml) in the formulation of the currently marketed NOVORAPID® (100 U/m rapid-acting product
Insulin aspart (100 U/ml) in the formulation comprising 22 mM trisodium citrate and 0.05 mg/ml dodecyl maltoside Both formulations tested comprised phenol (15.9 mM), m-cresol (15.9 mM) and ionic zinc (19.7 µg/ml, excluding counter-anion, as $ZnCl_2$) and were adjusted to pH7.4. The additional components of each formulation are listed in Table 16.

TABLE 16

Additional components in formulations of insulin aspart (100 U/ml) tested.

| Formulation | Sodium phosphate (mM) | NaCl (mM) | Glycerol (mM) | Trisodium citrate (mM) | Dodecyl maltoside (mg/ml) |
|---|---|---|---|---|---|
| 13A (i.e. composition of NOVORAPID ®) | 7 | 10 | 174 | | |
| 13B | 2 | 150 | | 22 | 0.05 |

Pharmacodynamic profiles of formulations 13A and 13B are shown in FIG. 2. The formulation of insulin aspart comprising trisodium citrate and dodecyl maltoside resulted in a considerably more rapid onset of action compared with the composition of the currently marketed NOVORAPID® rapid-acting product.

Example 14: Effect of Excipients on Pharmacodynamics and Pharmacokinetic Profile of Insulin Aspart (100 U/ml)

Pharmacodynamic profile of insulin aspart was compared in the following formulations using the Diabetic Pig Pharmacokinetic/Pharmacodynamic Model (see General Methods (c)):

Insulin aspart (100 U/ml) in the formulation K in Example 1 of WO2010/149772 which was shown to have a significantly more rapid onset of action compared with NOVORAPID® (100 U/ml) rapid-acting product Insulin aspart (100 U/ml) in the formulation of the currently marketed NOVORAPID® (100 U/ml) rapid-acting product Insulin aspart (100 U/ml) in the formulation comprising 22 mM trisodium citrate and 0.05 mg/ml dodecyl maltoside Insulin aspart (100 U/ml) in the formulation comprising 22 mM L-histidine and 0.05 mg/ml dodecyl maltoside All formulations tested comprised phenol (16 mM), m-cresol (16 mM) and ionic zinc (19.7 µg/ml, excluding counter-anion, as $ZnCl_2$) and were adjusted to pH 7.4. The additional components of each formulation are listed in Table 17.

TABLE 17

Additional components in formulations of insulin aspart (100 U/ml) tested.

| | Na phosphate (mM) | TRIS (mM) | NaCl (mM) | Glycerol (mM) | Trisodium citrate (mM) | Histidine (mM) | Nicotinamide (mM) | Arginine (mM) | Dodecyl maltoside (mg/ml) |
|---|---|---|---|---|---|---|---|---|---|
| 14A* | | 7 | 10 | 83.6 | | | 80 | 30 | |
| 14B** | 7 | | 10 | 174 | | | | | |
| 14C | 2 | | 150 | | 22 | | | | 0.05 |
| 14D | 2 | | 150 | | | 22 | | | 0.05 |

*Formulation K in WO2010/149772
**Formulation of NOVORAPID ®

Pharmacodynamic profiles of formulations 14A-14D are shown in FIG. 3. The formulation K of WO2010/149772 was confirmed to result in a more rapid onset of action compared with the composition of the currently marketed NOVORAPID® rapid-acting product of insulin aspart (Formulation 14A vs Formulation 14B). Formulations comprising either trisodium citrate and dodecyl maltoside (14C) or histidine and dodecyl maltoside (14D) also resulted in a considerably more rapid onset of action compared with the formulation of the currently marketed NOVORAPID® rapid-acting product (14B).

The pharmacokinetic profiles of formulations 14A, 14B and 14C (using the Diabetic Pig Pharmacokinetic/Pharmacodynamic Model (see General Methods (c)), FIG. 4) were in line with the pharmacodynamic profiles, showing that formulation K of WO2010/149772 and formulation comprising trisodium citrate and dodecyl maltoside resulted in a more rapid increase in serum insulin level compared with the formulation of the marketed NOVORAPID® product. The pharmacokinetic profile of formulation 14D was not tested.

Example 15—Comparison of Pharmacodynamic and Pharmacokinetic Profiles of Insulin Aspart (100 and 1000 U/ml) Formulations in the Presence and in the Absence of Citrate and Dodecyl Maltoside Pharmacodynamic and pharmacokinetic profile of insulin aspart was compared in the following compositions using the Diabetic Pig Pharmacokinetic/Pharmacodynamic Model (see General Methods (c)):

Insulin aspart (100 U/ml) in the formulation of the currently marketed NOVORAPID® (100 U/ml) rapid-acting product Insulin aspart (1000 U/ml) in the formulation of the currently marketed NOVORAPID® (100 U/ml) rapid-acting product Insulin aspart (1000 U/ml) in a formulation of the invention comprising 22 mM trisodium citrate and 0.1 mg/ml dodecyl maltoside Insulin aspart (1000 U/ml) in a formulation of the invention comprising 44 mM trisodium citrate and 0.1 mg/ml dodecyl maltoside All formulations tested comprised phenol (15.9 mM) and m-cresol (15.9 mM) and were adjusted to pH 7.4. The additional components of each formulation are listed in Table 18.

TABLE 18

Additional components in formulations of insulin aspart tested.

| Formulation | Insulin aspart (U/ml) | Sodium phosphate (mM) | NaCl (mM) | Glycerol (mM) | Ionic zinc* (µg/ml) | Trisodium citrate (mM) | Dodecyl maltoside (mg/ml) |
|---|---|---|---|---|---|---|---|
| 15A | 100 | 7 | 10 | 174 | 19.7 | | |
| 15B | 1000 | 7 | 10 | 174 | 197 | | |
| 15C | 1000 | 2 | 150 | | 197 | 22 | 0.1 |
| 15D | 1000 | 2 | 150 | | 197 | 44 | 0.1 |

*Does not include the contribution of counter-anion

Pharmacodynamic profiles of formulations 15A-15D are shown in FIG. 5. It was shown that increasing the concentration of insulin aspart from 100 U/ml to 1000 U/ml in the formulation of the marketed NOVORAPID® product led to a slower onset of action. This is in line with previous reports of dose-dependent delays of the glucose reduction effect of rapid-acting insulins (e.g. de la Peña et al. Pharmacokinetics and Pharmacodynamics of high-dose human regular U-500 insulin versus human regular U-100 insulin in healthy obese subjects, Diabetes Care, 24, pp 2496-2501, 2011). It was also shown (FIG. 5) that a formulation of insulin aspart (1000 U/ml) comprising 44 mM trisodium citrate and 0.1 mg/ml dodecyl maltoside resulted in a pharmacodynamic profile that was comparable with that achieved by the formulation of the marketed NOVORAPID® product (100 U/ml). Such acceleration of the onset of the glucose reduction was not observed in a composition comprising 22 mM trisodium citrate and 0.1 mg/ml dodecyl maltoside, indicating that this concentration of citrate is too low to achieve the accelerating effect at this concentration of insulin aspart.

The pharmacokinetic profiles of formulations 15A, 15B and 15D (FIG. 6) were in line with the pharmacodynamic profiles, showing that increasing the concentration of insulin aspart from 100 U/ml to 1000 U/ml in the formulation of the marketed NOVORAPID® product led to a slower increase in serum insulin level, whereas the formulation comprising 44 mM trisodium citrate and 0.1 mg/ml dodecyl maltoside resulted in a profile that was comparable with that achieved by the formulation of the marketed NOVORAPID® product (100 U/ml). The pharmacokinetic profile of Formulation 15C was not tested.

The $T_{MAX}$ and $T_{1/2MAX}$ mean values and standard deviations (SD) relating to the pharmacokinetic profiles of formulations 15A, 15B and 15D are shown in Table 19 below.

TABLE 19

$T_{MAX}$ and $T_{1/2MAX}$ mean values and standard deviations (SD) relating to the pharmacokinetic profiles of formulations 15A, 15B and 15D.

|  | $T_{MAX}$ (mean) | $T_{MAX}$ (SD) | $T_{1/2MAX}$ (mean) | $T_{1/2MAX}$ (SD) |
|---|---|---|---|---|
| 15A | 25.71 | 8.38 | 8.01 | 2.35 |
| 15B | 90.83 | 21.68 | 28.67 | 8.02 |
| 15D | 20.71 | 6.07 | 7.00 | 3.53 |

Results of the Student's t-test performed to evaluate bioequivalence between formulations 15A, 15B and 15D are shown in Table 20 below. Formulation 15A and 15D were shown to be bioequivalent, whereas formulations 15A and 15B and formulations 15B and 15D were shown to be non-bioequivalent.

TABLE 20

Bioequivalence t-test analysis of the pharmacokinetic profiles of formulations 15A, 15B and 15D.

|  | $T_{MAX}$ p-value | $T_{1/2MAX}$ p-value |
|---|---|---|
| 15A vs 15B | 0.0118 | 0.0115 |
| 15A vs 15D | 0.2507 | 0.3762 |
| 15B vs 15D | 0.0177 | 0.0107 |

Example 16—Stability of Insulin Lispro in the Presence of Trisodium Citrate and Non-Ionic Surfactants—Comparison with Formulations Disclosed in WO2016/100042

The following composition of insulin lispro (100 U/ml) of WO2016/100042 was selected based on the description on page 50 (lines 15-20): citrate (25 mM—from sodium citrate), poloxamer 188 (0.09% w/v), glycerol (16 mg/ml), m-cresol (3.15 mg/ml), zinc (0.3 mM, from zinc chloride), magnesium chloride (5 mM), sodium chloride (13 mM), pH 7.45. This composition is referred to as the "base formulation" below.

The effect of the following parameters was investigated on stability of insulin lispro by changing selected components and/or their concentrations in the base formulation:
  Effect of poloxamer 188 concentration
  Effect of NaCl concentration (i.e. effect of total chloride concentration)
  Effect of the presence of magnesium chloride
  Effect of dodecyl maltoside (as a replacement for poloxamer 188)

To allow further comparison all of the above effects were also investigated using insulin aspart.

Stability of insulin lispro and insulin aspart was tested under two separate stress conditions, in line with the stresses described in WO2016/100042:
  Storage at 30° C. (without agitation)
  Shaking stress (75 strokes per minute, 30° C.)

All formulations tested comprised insulin lispro or insulin aspart (100 U/ml), trisodium citrate (25 mM), glycerol (16 mg/ml), m-cresol (3.15 mg/ml) and zinc (0.3 mM, from zinc chloride) and were adjusted to pH 7.45. Additional components are stated in Tables 21-24.

Using insulin lispro it was shown (Tables 21 and 22) that:
  The stability of insulin lispro achieved in the presence of dodecyl maltoside was considerably better than that achieved in corresponding compositions comprising poloxamer 188. The effect was observed under both stress conditions.
  Lower concentrations of dodecyl maltoside appeared to provide better stability of insulin lispro than higher ones. The effect was observed under both stress conditions.
  Removing magnesium chloride (whilst maintaining the total chloride concentration by increasing the concentration of NaCl) led to impairment of stability of insulin lispro under both stress conditions. This indicates a stabilising effect of magnesium ions. It was noted that the presence of magnesium chloride had a modestly stabilising effect on dodecyl maltoside-containing formulations.
  The concentration total chloride (by increasing concentration of NaCl) had a minimal impact on stability of insulin lispro at this concentration of insulin lispro.

Similar observations were made using insulin aspart (Tables 23 and 24).

TABLE 21

Visual scores of insulin lispro (100 U/ml) formulations using Visual Assessment Scoring Method B following non-agitated storage at 30° C.

| Surfactant | Sodium chloride | Magnesium chloride | 0 weeks | 1 week | 2 weeks | 4 weeks | 8 weeks |
|---|---|---|---|---|---|---|---|
| Poloxamer 188 (0.09%) | 13 mM | 5 mM | 1 | 1 | 2 | 3 | 3 |
| Poloxamer 188 (0.06%) | 13 mM | 5 mM | 1 | 1 | 2 | 3 | 4 |
| Poloxamer 188 (0.03%) | 13 mM | 5 mM | 1 | 1 | 2 | 3 | 4 |
| Poloxamer 188 (0.01%) | 13 mM | 5 mM | 1 | 2 | 2 | 4 | 4 |
| Poloxamer 188 (0.005%) | 13 mM | 5 mM | 1 | 2 | 3 | 4 | 5 |
| None | 13 mM | 5 mM | 1 | 2 | 2 | 4 | 5 |
| Dodecyl maltoside (0.09%) | 13 mM | 5 mM | 1 | 1 | 1 | 2 | 3 |
| Dodecyl maltoside (0.06%) | 13 mM | 5 mM | 1 | 1 | 1 | 1 | 2 |
| Dodecyl maltoside (0.03%) | 13 mM | 5 mM | 1 | 1 | 1 | 1 | 2 |
| Dodecyl maltoside (0.01%) | 13 mM | 5 mM | 1 | 1 | 1 | 1 | 1 |
| Dodecyl maltoside (0.005%) | 13 mM | 5 mM | 1 | 1 | 1 | 1 | 1 |
| Poloxamer 188 (0.09%) | 150 mM | 5 mM | 1 | 1 | 2 | 3 | 4 |
| Poloxamer 188 (0.005%) | 150 mM | 5 mM | 1 | 2 | 2 | 3 | 4 |
| Dodecyl maltoside (0.09%) | 150 mM | 5 mM | 1 | 1 | 2 | 2 | 3 |
| Dodecyl maltoside (0.005%) | 150 mM | 5 mM | 1 | 1 | 1 | 2 | 2 |
| Poloxamer 188 (0.09%) | 60 mM | 5 mM | 1 | 1 | 2 | 2 | 4 |

TABLE 21-continued

Visual scores of insulin lispro (100 U/ml) formulations using Visual Assessment Scoring Method B following non-agitated storage at 30° C.

| Surfactant | Sodium chloride | Magnesium chloride | 0 weeks | 1 week | 2 weeks | 4 weeks | 8 weeks |
|---|---|---|---|---|---|---|---|
| Poloxamer 188 (0.005%) | 60 mM | 5 mM | 1 | 2 | 2 | 3 | 4 |
| Dodecyl maltoside (0.09%) | 60 mM | 5 mM | 1 | 1 | 1 | 2 | 3 |
| Dodecyl maltoside (0.005%) | 60 mM | 5 mM | 1 | 1 | 1 | 2 | 2 |
| Poloxamer 188 (0.09%) | 23 mM | 0 mM | 1 | 2 | 3 | 4 | 5 |
| Poloxamer 188 (0.005%) | 23 mM | 0 mM | 1 | 2 | 4 | 4 | 5 |
| Dodecyl maltoside (0.09%) | 23 mM | 0 mM | 1 | 1 | 3 | 4 | 4 |
| Dodecyl maltoside (0.005%) | 23 mM | 0 mM | 1 | 1 | 1 | 2 | 2 |

TABLE 22

Visual scores of insulin lispro (100 U/ml) formulations using Visual Assessment Scoring Method B following shaking stress (75 strokes per minute, 30° C.).

| Surfactant | Sodium chloride | Magnesium chloride | 0 days | 1 day | 3 days | 8 days | 13 days |
|---|---|---|---|---|---|---|---|
| Poloxamer 188 (0.09%) | 13 mM | 5 mM | 1 | 1 | 2 | 4 | 5 |
| Poloxamer 188 (0.06%) | 13 mM | 5 mM | 1 | 1 | 1 | 2 | 3 |
| Poloxamer 188 (0.03%) | 13 mM | 5 mM | 1 | 1 | 2 | 3 | 5 |
| Poloxamer 188 (0.01%) | 13 mM | 5 mM | 1 | 1 | 3 | 4 | 5 |
| Poloxamer 188 (0.005%) | 13 mM | 5 mM | 1 | 2 | 3 | 5 | 5 |
| None | 13 mM | 5 mM | 1 | 1 | 2 | 4 | 5 |
| Dodecyl maltoside (0.09%) | 13 mM | 5 mM | 1 | 1 | 1 | 1 | 2 |
| Dodecyl maltoside (0.06%) | 13 mM | 5 mM | 1 | 1 | 1 | 1 | 1 |
| Dodecyl maltoside (0.03%) | 13 mM | 5 mM | 1 | 1 | 1 | 1 | 1 |
| Dodecyl maltoside (0.01%) | 13 mM | 5 mM | 1 | 1 | 1 | 1 | 1 |
| Dodecyl maltoside (0.005%) | 13 mM | 5 mM | 1 | 1 | 1 | 1 | 1 |
| Poloxamer 188 (0.09%) | 150 mM | 5 mM | 1 | 1 | 1 | 2 | 3 |
| Poloxamer 188 (0.005%) | 150 mM | 5 mM | 1 | 1 | 2 | 3 | 5 |
| Dodecyl maltoside (0.09%) | 150 mM | 5 mM | 1 | 1 | 1 | 1 | 1 |
| Dodecyl maltoside (0.005%) | 150 mM | 5 mM | 1 | 1 | 1 | 1 | 1 |
| Poloxamer 188 (0.09%) | 60 mM | 5 mM | 1 | 1 | 2 | 3 | 5 |
| Poloxamer 188 (0.005%) | 60 mM | 5 mM | 1 | 1 | 4 | 5 | 5 |
| Dodecyl maltoside (0.09%) | 60 mM | 5 mM | 1 | 1 | 1 | 1 | 2 |
| Dodecyl maltoside (0.005%) | 60 mM | 5 mM | 1 | 1 | 1 | 1 | 2 |
| Poloxamer 188 (0.09%) | 23 mM | 0 mM | 1 | 4 | 5 | 5 | 5 |
| Poloxamer 188 (0.005%) | 23 mM | 0 mM | 1 | 4 | 5 | 5 | 5 |
| Dodecyl maltoside (0.09%) | 23 mM | 0 mM | 1 | 1 | 1 | 1 | 3 |
| Dodecyl maltoside (0.005%) | 23 mM | 0 mM | 1 | 1 | 1 | 1 | 2 |

TABLE 23

Visual scores of insulin aspart (100 U/ml) formulations using Visual Assessment Scoring Method B following non-agitated storage at 30° C.

| Surfactant | Sodium chloride | Magnesium chloride | 0 weeks | 1 week | 2 weeks | 4 weeks |
|---|---|---|---|---|---|---|
| Poloxamer 188 (0.09%) | 13 mM | 5 mM | 1 | 3 | 4 | 4 |
| Poloxamer 188 (0.06%) | 13 mM | 5 mM | 1 | 2 | 4 | 4 |
| Poloxamer 188 (0.03%) | 13 mM | 5 mM | 1 | 3 | 4 | 5 |
| Poloxamer 188 (0.01%) | 13 mM | 5 mM | 1 | 3 | 4 | 5 |
| Poloxamer 188 (0.005%) | 13 mM | 5 mM | 1 | 3 | 5 | 5 |
| None | 13 mM | 5 mM | 1 | 3 | 4 | 5 |
| Dodecyl maltoside (0.09%) | 13 mM | 5 mM | 1 | 3 | 4 | 5 |
| Dodecyl maltoside (0.06%) | 13 mM | 5 mM | 1 | 3 | 3 | 3 |
| Dodecyl maltoside (0.03%) | 13 mM | 5 mM | 1 | 2 | 3 | 3 |
| Dodecyl maltoside (0.01%) | 13 mM | 5 mM | 1 | 2 | 2 | 2 |
| Dodecyl maltoside (0.005%) | 13 mM | 5 mM | 1 | 1 | 1 | 1 |
| Poloxamer 188 (0.09%) | 150 mM | 5 mM | 1 | 4 | 4 | 4 |
| Poloxamer 188 (0.005%) | 150 mM | 5 mM | 1 | 2 | 4 | 5 |
| Dodecyl maltoside (0.09%) | 150 mM | 5 mM | 1 | 1 | 2 | 3 |
| Dodecyl maltoside (0.005%) | 150 mM | 5 mM | 1 | 1 | 2 | 2 |
| Poloxamer 188 (0.09%) | 60 mM | 5 mM | 1 | 3 | 3 | 4 |
| Poloxamer 188 (0.005%) | 60 mM | 5 mM | 1 | 2 | 3 | 5 |

TABLE 23-continued

Visual scores of insulin aspart (100 U/ml) formulations using Visual Assessment Scoring Method B following non-agitated storage at 30° C.

| Surfactant | Sodium chloride | Magnesium chloride | 0 weeks | 1 week | 2 weeks | 4 weeks |
|---|---|---|---|---|---|---|
| Dodecyl maltoside (0.09%) | 60 mM | 5 mM | 1 | 1 | 3 | 4 |
| Dodecyl maltoside (0.005%) | 60 mM | 5 mM | 1 | 1 | 1 | 1 |
| Poloxamer 188 (0.09%) | 23 mM | 0 mM | 1 | 5 | 5 | 5 |
| Poloxamer 188 (0.005%) | 23 mM | 0 mM | 1 | 5 | 5 | 5 |
| Dodecyl maltoside (0.09%) | 23 mM | 0 mM | 1 | 2 | 3 | 4 |
| Dodecyl maltoside (0.005%) | 23 mM | 0 mM | 1 | 1 | 1 | 2 |

TABLE 24

Visual scores of insulin aspart (100 U/ml) compositions using Visual Assessment Scoring Method B following shaking stress (75 strokes per minute, 30° C.).

| Surfactant | Sodium chloride | Magnesium chloride | 0 days | 1 day | 3 days | 8 days | 13 days |
|---|---|---|---|---|---|---|---|
| Poloxamer 188 (0.09%) | 13 mM | 5 mM | 1 | 2 | 5 | 5 | 5 |
| Poloxamer 188 (0.06%) | 13 mM | 5 mM | 1 | 2 | 5 | 5 | 5 |
| Poloxamer 188 (0.03%) | 13 mM | 5 mM | 1 | 3 | 3 | 5 | 5 |
| Poloxamer 188 (0.01%) | 13 mM | 5 mM | 1 | 3 | 5 | 5 | 5 |
| Poloxamer 188 (0.005%) | 13 mM | 5 mM | 1 | 3 | 5 | 5 | 5 |
| None | 13 mM | 5 mM | 1 | 3 | 5 | 5 | 5 |
| Dodecyl maltoside (0.09%) | 13 mM | 5 mM | 1 | 3 | 3 | 4 | 5 |
| Dodecyl maltoside (0.06%) | 13 mM | 5 mM | 1 | 2 | 3 | 3 | 4 |
| Dodecyl maltoside (0.03%) | 13 mM | 5 mM | 1 | 2 | 3 | 4 | 4 |
| Dodecyl maltoside (0.01%) | 13 mM | 5 mM | 1 | 2 | 2 | 3 | 3 |
| Dodecyl maltoside (0.005%) | 13 mM | 5 mM | 1 | 2 | 2 | 3 | 3 |
| Poloxamer 188 (0.09%) | 150 mM | 5 mM | 1 | 1 | 3 | 5 | 5 |
| Poloxamer 188 (0.005%) | 150 mM | 5 mM | 1 | 2 | 5 | 5 | 5 |
| Dodecyl maltoside (0.09%) | 150 mM | 5 mM | 1 | 1 | 2 | 3 | 4 |
| Dodecyl maltoside (0.005%) | 150 mM | 5 mM | 1 | 1 | 1 | 2 | 2 |
| Poloxamer 188 (0.09%) | 60 mM | 5 mM | 1 | 2 | 5 | 5 | 5 |
| Poloxamer 188 (0.005%) | 60 mM | 5 mM | 1 | 3 | 5 | 5 | 5 |
| Dodecyl maltoside (0.09%) | 60 mM | 5 mM | 1 | 2 | 3 | 3 | 4 |
| Dodecyl maltoside (0.005%) | 60 mM | 5 mM | 1 | 1 | 2 | 3 | 3 |
| Poloxamer 188 (0.09%) | 23 mM | 0 mM | 1 | 3 | 5 | 5 | 5 |
| Poloxamer 188 (0.005%) | 23 mM | 0 mM | 1 | 4 | 5 | 5 | 5 |
| Dodecyl maltoside (0.09%) | 23 mM | 0 mM | 1 | 2 | 3 | 4 | 5 |
| Dodecyl maltoside (0.005%) | 23 mM | 0 mM | 1 | 1 | 1 | 3 | 3 |

Example 17—Stability of Insulin Lispro and Insulin Aspart in a Formulation Comprising Dodecyl Maltoside Disclosed in U.S. Pat. No. 7,998,927

The following composition of U.S. Pat. No. 7,998,927 was selected based on the description in Example 1 (column 25): sodium acetate buffer (5 mM), saline (0.9% w/v), dodecyl maltoside (0.18% w/v), pH 6.0. Insulin aspart (100 U/ml) and insulin lispro (100 U/ml) were prepared in the above formulation.

It was found that following their preparation the formulations of both insulin analogues were cloudy, with a large number of particles (scoring 5 by Visual Assessment Scoring Method B) even in the absence of any stress. Stirring of the samples for 24 hours did not achieve any improvements and the compositions remained very cloudy. It is very likely that the impossibility of preparing the formulations as clear solutions was due to the fact that the pH was very close to the isoelectric point of the insulin analogues (pI=~5.4). Adjusting the pH of the composition to ≥7.0 led to a clear solution very quickly, but it was found impossible to achieve a clear solution at pH 6.0. Therefore, the composition of U.S. Pat. No. 7,998,927 is not useable as a formulation of a therapeutic product at 100 U/ml or more.

Example 18—Stability of Human Insulin in Formulations Comprising Dodecyl Maltoside at pH 6.0 and 7.4—Comparison with Formulations Disclosed in U.S. Pat. No. 7,998,927

Recombinant human insulin was obtained from Sigma Aldrich, St. Louis, Mo. (USA).

The following composition of U.S. Pat. No. 7,998,927 was selected based on the description in Example 1 (column 25): sodium acetate buffer (5 mM), saline (0.9% w/v), dodecyl maltoside (0.18% w/v), pH 6.0.

Example 1 of U.S. Pat. No. 7,998,927 describes compositions of human insulin in the above formulation at 5 U/ml (i.e. 0.5 U in 100 μl) and 25 U/ml (i.e. 0.5 U in 20 μl). In both cases the insulin concentration was lower than that in the marketed insulin products for human use (≥100 U/ml).

Formulations of human insulin were prepared in the above formulation at 5 U/ml, 25 U/ml and 100 U/ml. It was found impossible to prepare the above formulation of human insulin as a clear solution at any of the three insulin concentrations tested (Table 25). The compositions showed a number of particles even in the absence of any stress, scoring 3 (5 U/ml insulin formulation), 4 (25 U/ml insulin formulation) and 5 (100 U/ml insulin formulation) by Visual Assessment Scoring Method B. Subsequent stress at 30 led to further rapid particle formation, all three formulations scoring 5 by Visual Assessment Scoring Method B following 4 weeks incubation at 30° C.

TABLE 25

Visual scores of human insulin formulations using Visual Assessment Scoring Method B following storage at 30° C.

| Human insulin (U/ml) | Sodium acetate (mM) | Sodium chloride (mM) | Dodecyl maltoside (% w/v) | pH | 0 weeks | 2 weeks | 4 weeks |
|---|---|---|---|---|---|---|---|
| 5 | 5 | 154* | 0.18 | 6.0 | 3 | 4 | — |
| 25 | 5 | 154* | 0.18 | 6.0 | 4 | 5 | — |
| 100 | 5 | 154* | 0.18 | 6.0 | 5 | 5 | — |

*= 0.9% w/v

The effect of the addition of citric acid to formulations comprising dodecyl maltoside at 0.18% w/v and 0.005% w/v concentrations was also compared. All formulations tested comprised human insulin (100 U/ml), phenol (15.9 mM), m-cresol (15.9 mM), sodium phosphate (2 mM), ionic zinc (19.7 µg/ml, excluding counter-anion, as $ZnCl_2$) and were adjusted to pH 7.4. Additional components are shown in Table 26.

It was shown (Table 26) that in the presence of citrate, formulations could be prepared as a clear liquid. However, only the formulations comprising the lower level of dodecyl maltoside remained stable following storage at 30° C. The formulations comprising 0.18% dodecyl maltoside showed a considerably greater particle formation.

TABLE 26

Visual scores of human insulin formulations using Visual Assessment Scoring Method B following storage at 30° C.

| Glycerol (mM) | Sodium chloride (mM) | Dodecyl maltoside (% w/v) | 0 weeks | 2 weeks | 4 weeks |
|---|---|---|---|---|---|
|  | 150 | 0.18 | 1 | 3 | 4 |
|  | 150 | 0.005 | 1 | 1 | 1 |
| 174 |  | 0.18 | 1 | 3 | 4 |
| 174 |  | 0.005 | 1 | 1 | 2 |

Example 19—Stability of Insulin Aspart in the Presence of Low Concentration of a Strong Chelating Agent, with and without a Surfactant The effect of low concentration of EDTA on stability of insulin aspart was investigated both in the absence and in the presence of a surfactant. The effect was investigated in two different background solutions:

Background solution 1: sodium phosphate (13.2 mM), sodium citrate (9.3 mM), magnesium sulphate (4 mM), glycerol (173.7 mM), phenol (0.3 mM), m-cresol (29.1 mM), ionic zinc (19.7 µg/ml, as $ZnCl_2$), pH 7.4

Background solution 2: sodium phosphate (2 mM), sodium citrate (22 mM), sodium chloride (150 mM), phenol (15.9 mM), m-cresol (15.9 mM), ionic zinc (19.7 µg/ml, as $ZnCl_2$), pH 7.4

Composition of the background solution 1 is identical to that shown in WO2015/120457 application (formulation BIOD-288 in Table 8), except the concentration of EDTA.

The formulations tested are shown in Table 27.

TABLE 27

Additional components in formulations of insulin aspart tested.

| | Background solution | EDTA (mM) | Dodecyl-β-D-maltoside (mg/ml) |
|---|---|---|---|
| Formulation 19A | 1 | 0 | 0 |
| Formulation 19B | 1 | 0.02 | 0 |
| Formulation 19C | 1 | 0.05 | 0 |
| Formulation 19D | 1 | 0.1 | 0 |
| Formulation 19E | 1 | 0.2 | 0 |
| Formulation 19F[1] | 1 | 0.33 | 0 |
| Formulation 19G | 2 | 0 | 0 |
| Formulation 19H | 2 | 0.02 | 0 |
| Formulation 19I | 2 | 0.05 | 0 |
| Formulation 19J | 2 | 0.1 | 0 |
| Formulation 19K | 2 | 0.2 | 0 |
| Formulation 19L | 2 | 0.33 | 0 |
| Formulation 19M | 2 | 0 | 0.05 |
| Formulation 19N[2] | 2 | 0.02 | 0.05 |
| Formulation 19O | 2 | 0.05 | 0.05 |
| Formulation 19P[3] | 2 | 0.1 | 0.05 |
| Formulation 19Q | 2 | 0.2 | 0.05 |
| Formulation 19R | 2 | 0.33 | 0.05 |

[1]corresponds to formulation BIOD-288 in Table 8 in WO2015/120457
[2]equivalent to formulation AG in Example 1
[3]equivalent to formulation AE in Example 1

Stability of insulin aspart was tested by visual assessment. Results are shown in Table 28. Particle formation was observed in both background solution in the absence of EDTA and dodecyl-β-D-maltoside, reaching the "Fail" limit (Visual score 4) in 7 days. The presence of 0.02 mM EDTA resulted in no measurable difference. The presence of higher concentrations of EDTA (0.05-0.33 mM) resulted in acceleration of particle formation, the effect being proportional to EDTA concentration. The EDTA-containing formulations thus reached the "Fail" limit at earlier time-points. The presence of dodecyl-β-D-maltoside significantly delayed the particle formation. The formulations containing up to 0.2 mM EDTA in the presence of dodecyl-β-D-maltoside remained at the "Pass" level up to the 7 day time-point and only the formulation containing 0.33 mM EDTA reached the "Fail" limit.

TABLE 28

Visual scores of insulin aspart formulations following storage at 30° C. Visual score 1: <10 very small particles; visual score 2: 10-20 very small particles; visual score 3: 20-50 particles, including larger particles; visual score 4: >50 particles, including larger particles.

| | 0 weeks | 1 day | 4 days | 7 days | 14 days | 28 days |
|---|---|---|---|---|---|---|
| Formulation 19A | 1 | 1 | 1 | 3 | 4 | 4 |
| Formulation 19B | 1 | 1 | 1 | 3 | 4 | 4 |
| Formulation 19C | 1 | 1 | 3 | 3 | 4 | 4 |
| Formulation 19D | 1 | 1 | 3 | 3 | 4 | 4 |
| Formulation 19E | 1 | 1 | 4 | 4 | 4 | 4 |
| Formulation 19F | 1 | 1 | 4 | 4 | 4 | 4 |

TABLE 28-continued

Visual scores of insulin aspart formulations following storage at 30° C.
Visual score 1: <10 very small particles; visual score 2: 10-20
very small particles; visual score 3: 20-50 particles, including larger
particles; visual score 4: >50 particles, including larger particles.

| | 0 weeks | 1 day | 4 days | 7 days | 14 days | 28 days |
|---|---|---|---|---|---|---|
| Formulation 19G | 1 | 1 | 1 | 3 | 3 | 4 |
| Formulation 19H | 1 | 1 | 1 | 3 | 4 | 4 |
| Formulation 19I | 1 | 1 | 3 | 3 | 4 | 4 |
| Formulation 19J | 1 | 2 | 3 | 4 | 4 | 4 |
| Formulation 19K | 1 | 2 | 4 | 4 | 4 | 4 |
| Formulation 19L | 1 | 2 | 4 | 4 | 4 | 4 |
| Formulation 19M | 1 | 1 | 1 | 1 | 1 | 1 |
| Formulation 19N | 1 | 1 | 1 | 1 | 1 | 1 |
| Formulation 19O | 1 | 1 | 1 | 1 | 1 | 1 |
| Formulation 19P | 1 | 1 | 1 | 1 | 1 | 2 |
| Formulation 19Q | 1 | 1 | 1 | 2 | 3 | 4 |
| Formulation 19R | 1 | 1 | 2 | 3 | 4 | 4 |

Example 20—Stability of Insulin Aspart in the Presence of Nicotinamide and Additional Excipients The stability of insulin aspart in the formulation of currently marketed NovoRapid® rapid-acting product (formulation 20A in Table 29) was compared with that of insulin aspart in a number of nicotinamide-containing formulations (formulations 20B-20Q in Table 29) following storage at 37° C. Formulation F2 contained arginine and was based on formulation K in Table 1 of WO2010/149772, which was shown to have an ultra-rapid acting pharmacodynamic/pharmacokinetic profile. The only difference between formulation 20B and formulation K of WO2010/149772 is the use of phosphate buffer instead of TRIS in order to eliminate a buffer effect in comparing with currently marketed NovoRapid®. Formulations 20C-20Q were designed to study the effect on insulin aspart stability of (1) salts (2) polyols and (3) non-ionic surfactants.

Results of the visual assessment of formulations 20A-20Q are shown in Table 30. It was surprisingly shown that the arginine-containing formulation 20B resulted in a considerably greater rate of particle formation compared with formulation 20A (i.e. formulation of NovoRapid®). Formulation 20B reached the "Fail" limit after 1 week of storage at 37° C., whilst formulation 20A only reached the limit following 3 weeks storage at the same temperature. It was also shown that removal of the 10 mM NaCl from formulation 20B had no significant impact on the rate of particle formation (formulation 20C vs. formulation 20B). Removal of arginine from formulation 20C led to a considerable reduction in the rate of particle formation (formulation 20D vs. formulation 20C) and it was also shown that increasing the concentration of glycerol in the arginine-free formulation (formulation 20E vs. formulation 20D) or replacing it with mannitol, an alternative polyol, (formulation 20F vs. formulation 20E), had only a minimal impact on the rate of particle formation. Use of salts, including sodium chloride (formulations 20G-20I), potassium chloride (formulation 20J) and sodium acetate (formulation 20K) resulted in a similar rate of particle formation to that in the presence of arginine. Only the formulation comprising the lowest concentration of sodium chloride (formulation 20G) appeared to result in a "Pass" visual score at 1 week, but reached a "Fail" score 5 at 2 weeks alongside all other formulations comprising a salt. Addition of a non-ionic surfactant to the formulations comprising either 70 mM sodium chloride (formulation 20M, formulation 20O and formulation 20Q) or 141 mM glycerol (formulation 20L, formulation 20N and formulation 20P) resulted in a considerable reduction in the rate of particle formation. In all cases, the rate of particle formation was lower or comparable with that of formulation 20A (i.e. formulation of NovoRapid®). The formulations containing dodecyl maltoside (formulation 20P and formulation 20Q) gave the best performance.

TABLE 29

Compositions of formulations 20A-20Q of insulin aspart tested. All formulations comprised insulin aspart (100 U/ml), ionic zinc (0.3 mM) as $ZnCl_2$, phenol (16 mM) and m-cresol (16 mM) and were adjusted to pH 7.4. Other components are listed in the table.

| | Sodium phosphate (mM) | Sodium chloride (mM) | Potassium chloride (mM) | Sodium acetate (mM) | Arginine (mM) | Glycerol (mM) | Mannitol (mM) | Nicotinamide (mM) | Polysorbate 20 (mg/ml) | Polysorbate 80 (mg/ml) | Dodecyl maltoside (mg/ml) |
|---|---|---|---|---|---|---|---|---|---|---|---|
| 20A | 7 | 10 | | | | 174 | | | | | |
| 20B | 7 | 10 | | | 30 | 84 | | 80 | | | |
| 20C | 7 | | | | 30 | 84 | | 80 | | | |
| 20D | 7 | | | | | 84 | | 80 | | | |
| 20E | 7 | | | | | 141 | | 80 | | | |
| 20F | 7 | | | | | | 141 | 80 | | | |
| 20G | 7 | 140 | | | | | | 80 | | | |
| 20H | 7 | 70 | | | | | | 80 | | | |
| 20I | 7 | 30 | | | | 83 | | 80 | | | |
| 20J | 7 | | 70 | | | | | 80 | | | |
| 20K | 7 | | | 70 | | | | 80 | | | |
| 20L | 7 | | | | | 141 | | 80 | 0.05 | | |
| 20M | 7 | 70 | | | | | | 80 | 0.05 | | |
| 20N | 7 | | | | | 141 | | 80 | | 0.05 | |
| 20O | 7 | 70 | | | | | | 80 | | 0.05 | |
| 20P | 7 | | | | | 141 | | 80 | | | 0.05 |
| 20Q | 7 | 70 | | | | | | 80 | | | 0.05 |

TABLE 30

Visual scores of insulin aspart formulations 20A-20Q following storage at 37° C.
Visual score 1: clear solution, virtually free of particles; visual score 2: ~5 very small particles; visual score 3: ~10-20 very small particles; visual score 4: 20-50 particles, including larger particles; visual score 5: >50particles, including larger particles.

|  | Visual score (0 weeks) | Visual score (1 week) | Visual score (2 weeks) | Visual score (3 weeks) | Visual score (4 weeks) |
|---|---|---|---|---|---|
| 20A | 1 | 2 | 3 | 4 | 5 |
| 20B | 1 | 4 | 5 | 5 | 5 |
| 20C | 1 | 4 | 5 | 5 | 5 |
| 20D | 1 | 3 | 3 | 4 | 4 |
| 20E | 1 | 3 | 4 | 4 | 4 |
| 20F | 1 | 3 | 3 | 4 | 4 |
| 20G | 1 | 4 | 5 | 5 | 5 |
| 20H | 1 | 4 | 5 | 5 | 5 |
| 20I | 1 | 3 | 5 | 5 | 5 |
| 20J | 1 | 4 | 5 | 5 | 5 |
| 20K | 1 | 4 | 5 | 5 | 5 |
| 20L | 1 | 1 | 2 | 3 | 4 |
| 20M | 1 | 2 | 3 | 3 | 5 |
| 20N | 1 | 2 | 3 | 4 | 4 |
| 20O | 1 | 2 | 3 | 3 | 4 |
| 20P | 1 | 1 | 1 | 2 | 2 |
| 20Q | 1 | 1 | 1 | 2 | 3 |

Formation of HMWS in formulations 20A-20Q is shown in Table 31 and formation of chemically related species is shown in Table 32. The arginine-containing formulation 20B resulted in a lower rate of HMWS and chemically related species compared with formulation 20A (i.e. formulation of NovoRapid®). Removal of arginine from formulation 20C led to an impairment of stability, both with respect to HMWS and with respect to chemically related species (20D vs. 20C). Increasing the concentration of glycerol in the arginine-free formulation (20E vs. 20D) or replacing it with mannitol, an alternative polyol, (20F vs. 20E), had only a minimal impact on the stability. Use of salts, including sodium chloride (20G-20), potassium chloride (20J) and sodium acetate (20K) resulted in better stability, both with respect to HMWS and with respect to chemically related species compared with formulations that did not contain salts. The beneficial effect of a salt appeared to be concentration-dependent (20G-20I), and in all cases, it was better than that of the formulation 20A (i.e. formulation of NovoRapid®). Addition of a non-ionic surfactant to the formulations comprising either 70 mM sodium chloride (20M, 20O and 20Q) or 141 mM glycerol (20L, 20N and 20P) resulted in only minimal impact of stability both with respect to HMWS and with respect to chemically related species.

Overall, only formulations comprising a non-ionic surfactant and a salt resulted in stability that was considerably better in all aspects than that achieved in the marketed formulation of NovoRapid®.

TABLE 31

Increase in HMWS (vs. start) in insulin aspart formulations 20A-20Q assessed by SEC following storage at 37° C.

|  | Δ % HMWS (2 weeks vs. start) | Δ % HMWS (4 weeks vs. start) |
|---|---|---|
| 20A | 0.39 | 0.69 |
| 20B | 0.20 | 0.37 |
| 20C | 0.19 | 0.35 |
| 20D | 0.55 | 1.01 |
| 20E | 0.53 | 0.96 |
| 20F | 0.43 | 0.91 |
| 20G | 0.21 | 0.41 |
| 20H | 0.25 | 0.52 |
| 20I | 0.33 | 0.63 |
| 20J | 0.25 | 0.66 |
| 20K | 0.29 | 0.70 |
| 20L | 0.60 | 1.20 |
| 20M | 0.28 | 0.58 |
| 20N | 0.60 | 1.21 |
| 20O | 0.30 | 0.55 |
| 20P | 0.66 | 1.23 |
| 20Q | 0.26 | 0.52 |

TABLE 32

Increase in chemically related species insulin (vs. start) aspart formulations 20A-20Q assessed by reversed-phase chromatography following storage at 37° C.

|  | Δ % chemically related species (2 weeks vs. start) | Δ % chemically related species (4 weeks vs. start) |
|---|---|---|
| 20A | 1.56 | 3.35 |
| 20B | 0.98 | 2.09 |
| 20C | 1.00 | 2.14 |
| 20D | 1.49 | 3.39 |
| 20E | 1.52 | 3.38 |
| 20F | 1.39 | 2.99 |
| 20G | 0.82 | 1.64 |
| 20H | 0.98 | 1.84 |
| 20I | 1.22 | 2.59 |
| 20J | 0.86 | 1.75 |
| 20K | 0.97 | 2.16 |
| 20L | 1.71 | 3.37 |
| 20M | 1.00 | 1.89 |
| 20N | 1.6 | 3.33 |
| 20O | 1.02 | 1.80 |
| 20P | 1.72 | 3.34 |
| 20Q | 0.95 | 1.68 |

Example 21—Effect of Surfactants on the Stability of Insulin Aspart (100 U/ml) in a Glass Vial Under Agitation Stress The effect of surfactants was investigated on the stability of insulin aspart under agitation stress at 25° C. Formulations of insulin aspart (100 U/m) were placed in Type 1 glass vials with bromobutyl rubber stopper. The vials were placed on an orbital shaker and agitated at 110 RPM (25° C.). Stability of the samples was tested using Visual Assessment Scoring Method B. All formulations comprised insulin aspart (100 U/ml), phenol (15.9 mM), m-cresol (15.9 mM), sodium chloride (150 mM), ionic zinc (19.7 µg/ml—excluding counter-anion, as $ZnCl_2$) and sodium phosphate (2 mM) and were adjusted to pH7.4. Additional ingredients are shown in Table 33.

TABLE 33

Additional ingredients in formulations (21A-21L) of insulin aspart (100 U/ml).

| Formulation | Sodium citrate (mM) | Surfactant (all at 50 µg/ml) |
|---|---|---|
| 21A | 0 | None |
| 21B | 0 | Polysorbate 80 |
| 21C | 0 | Polysorbate 20 |
| 21D | 0 | Poloxamer 188 |
| 21E | 0 | Dodecyl maltoside |
| 21F | 0 | Decyl glucopyranoside |
| 21G | 22 | None |
| 21H | 22 | Polysorbate 80 |
| 21I | 22 | Polysorbate 20 |
| 21J | 22 | Poloxamer 188 |
| 21K | 22 | Dodecyl maltoside |
| 21L | 22 | Decyl glucopyranoside |

It was shown (Table 34) that the presence of alkyl glycosides, particularly dodecyl maltoside, resulted in a considerably slower rate of particle formation of insulin aspart, both in the presence and in the absence of 22 mM trisodium citrate. Other non-ionic surfactants (polysorbate 80, polysorbate 20 and poloxamer 188) also showed a stabilising effect, although not to the same extent as the alkyl glycosides.

TABLE 34

Visual scores of insulin aspart (100 U/ml) formulations using Visual Assessment Scoring Method B following agitation (110 RPM) at 25° C.

| Formulation | 1 day | 2 days | 3 days | 7 days |
|---|---|---|---|---|
| 21A | 3 | 5 | 5 | 5 |
| 21B | 1 | 1 | 2 | 3 |
| 21C | 2 | 3 | 3 | 4 |
| 21D | 2 | 4 | 5 | 5 |
| 21E | 1 | 1 | 1 | 1 |
| 21F | 1 | 1 | 2 | 2 |
| 21G | 5 | 5 | 5 | 5 |
| 21H | 2 | 3 | 4 | 5 |
| 21I | 3 | 3 | 5 | 5 |
| 21J | 3 | 4 | 5 | 5 |
| 21K | 1 | 1 | 1 | 1 |
| 21L | 1 | 2 | 2 | 3 |

Example 22—Effect of Surfactants on the Stability of Insulin Aspart (1000 U/ml) in a Glass Vial Under Agitation Stress The effect of surfactants was investigated on the stability of insulin aspart under agitation stress at 25° C. Formulations of insulin aspart (1000 U/m) were placed in Type 1 glass vials with bromobutyl rubber stopper. The vials were placed on an orbital shaker and agitated at 110 RPM (25° C.). Stability of the samples was tested using Visual Assessment Scoring Method B. All formulations comprised insulin aspart (1000 U/ml), phenol (15.9 mM), m-cresol (15.9 mM), glycerol (174 mM), ionic zinc (197 µg/ml—excluding counter-anion, as $ZnCl_2$) and sodium phosphate (2 mM) and were adjusted to pH 7.4. Additional ingredients are shown in Table 35.

TABLE 35

Additional ingredients in formulations (22A-22J) of insulin aspart (1000 U/ml).

| Formulation | Sodium citrate (mM) | Surfactant (all at 50 µg/ml) |
|---|---|---|
| 22A | 0 | None |
| 22B | 0 | Polysorbate 80 |
| 22C | 0 | Poloxamer 188 |
| 22D | 0 | Dodecyl maltoside |
| 22E | 0 | Decyl glucopyranoside |
| 22F | 44 | None |
| 22G | 44 | Polysorbate 80 |
| 22H | 44 | Poloxamer 188 |
| 22I | 44 | Dodecyl maltoside |
| 22J | 44 | Decyl glucopyranoside |

It was shown (Table 36) that the presence of alkyl glycosides, particularly dodecyl maltoside, resulted in a considerably slower rate of particle formation of insulin aspart, both in the presence and in the absence of 22 mM trisodium citrate. Other non-ionic surfactants (polysorbate 80 and poloxamer 188) also showed a stabilising effect, although not to the same extent as the alkyl glycosides.

TABLE 36

Visual scores of insulin aspart (1000 U/ml) formulations using Visual Assessment Scoring Method B following agitation (110 RPM) at 25° C.

| Formulation | 1 day | 2 days | 3 days | 7 days |
|---|---|---|---|---|
| 22A | 4 | 5 | 5 | 5 |
| 22B | 2 | 3 | 4 | 5 |
| 22C | 3 | 4 | 5 | 5 |
| 22D | 1 | 1 | 1 | 2 |
| 22E | 1 | 2 | 3 | 4 |
| 22F | 5 | 5 | 5 | 5 |
| 22G | 2 | 2 | 3 | 5 |
| 22H | 4 | 5 | 5 | 5 |
| 22I | 1 | 1 | 1 | 3 |
| 22J | 1 | 2 | 3 | 3 |

Example 23—Effect of Surfactants on the Stability of Insulin Aspart (100 U/Ml) in an Injection Pen Cartridge Under Agitation Stress The effect of surfactants was investigated on the stability of insulin aspart in an injection pen cartridge under agitation stress at 25° C. 2 mL aliquots of insulin aspart formulations (100 U/ml) were placed in 3 mL injection pen cartridges. The cartridges were placed on an orbital shaker and agitated at 110 RPM (25° C.). Stability of the samples was tested by visual assessment using Visual Assessment Scoring Method B. All formulations comprised insulin aspart (100 U/ml), phenol (15.9 mM), m-cresol (15.9 mM), sodium chloride (150 mM), ionic zinc (19.7 µg/ml—excluding counter-anion, as $ZnCl_2$) and sodium phosphate (2 mM) and were adjusted to pH 7.4. Additional ingredients are shown in Table 37.

TABLE 37

Additional ingredients in formulations (23A-23L) of insulin aspart (100 U/ml).

| Formulation | Sodium citrate (mM) | Surfactant (all at 50 μg/ml) |
|---|---|---|
| 23A | 0 | None |
| 23B | 0 | Polysorbate 80 |
| 23C | 0 | Polysorbate 20 |
| 23D | 0 | Poloxamer 188 |
| 23E | 0 | Dodecyl maltoside |
| 23F | 0 | Decyl glucopyranoside |
| 23G | 22 | None |
| 23H | 22 | Polysorbate 80 |
| 23I | 22 | Polysorbate 20 |
| 23J | 22 | Poloxamer 188 |
| 23K | 22 | Dodecyl maltoside |
| 23L | 22 | Decyl glucopyranoside |

It was shown (Table 38) that the presence of alkyl glycosides, particularly dodecyl maltoside, resulted in a considerably slower rate of particle formation of insulin aspart, both in the presence and in the absence of 22 mM trisodium citrate. Other non-ionic surfactants (polysorbate 80, polysorbate 20 and poloxamer 188) also showed a stabilising effect, although not to the same extent as the alkyl glycosides.

TABLE 38

Visual scores of insulin aspart (100 U/ml) formulations in insulin pen cartridges, using Visual Assessment Scoring Method B following agitation (110 RPM) at 25° C.

| Formulation | 1 day | 2 days | 3 days | 7 days |
|---|---|---|---|---|
| 23A | 2 | 4 | 5 | 5 |
| 23B | 1 | 2 | 2 | 3 |
| 23C | 1 | 2 | 3 | 4 |
| 23D | 2 | 2 | 3 | 5 |
| 23E | 1 | 1 | 1 | 1 |
| 23F | 1 | 2 | 2 | 2 |
| 23G | 5 | 5 | 5 | 5 |
| 23H | 1 | 2 | 4 | 5 |
| 23I | 2 | 3 | 4 | 5 |
| 23J | 2 | 4 | 5 | 5 |
| 23K | 1 | 1 | 1 | 1 |
| 23L | 1 | 1 | 2 | 3 |

Example 24—Effect of Surfactants on the Stability of Insulin Aspart (1000 U/Ml) in an Injection Pen Cartridge Under Agitation Stress The effect of surfactants was investigated on the stability of insulin aspart in an injection pen cartridge under agitation stress at 25° C. 2 mL aliquots of insulin aspart formulations (1000 U/ml) were placed in 3 mL injection pen cartridges. The cartridges were placed on an orbital shaker and agitated at 110 RPM (25° C.). Stability of the samples was tested by visual assessment using Visual Assessment Scoring Method B. All formulations comprised insulin aspart (1000 U/ml), phenol (15.9 mM), m-cresol (15.9 mM), glycerol (174 mM), ionic zinc (197 μg/ml—excluding counter-anion, as $ZnCl_2$) and sodium phosphate (2 mM) and were adjusted to pH 7.4. Additional ingredients are shown in Table 39.

TABLE 39

Additional ingredients in formulations (24A-24J) of insulin aspart (100 U/ml).

| Formulation | Sodium citrate (mM) | Surfactant (all at 50 μg/ml) |
|---|---|---|
| 24A | 0 | None |
| 24B | 0 | Polysorbate 80 |
| 24C | 0 | Poloxamer 188 |
| 24D | 0 | Dodecyl maltoside |
| 24E | 0 | Decyl glucopyranoside |
| 24F | 44 | None |
| 24G | 44 | Polysorbate 80 |
| 24H | 44 | Poloxamer 188 |
| 24I | 44 | Dodecyl maltoside |
| 24J | 44 | Decyl glucopyranoside |

It was shown (Table 40) that the presence of alkyl glycosides, particularly dodecyl maltoside, resulted in a considerably slower rate of particle formation of insulin aspart, both in the presence and in the absence of 22 mM trisodium citrate. Other non-ionic surfactants (polysorbate 80, polysorbate 20 and poloxamer 188) also showed a stabilising effect, although not to the same extent as the alkyl glycosides.

TABLE 40

Visual scores of insulin aspart (1000 U/ml) formulations in insulin pen cartridges, using Visual Assessment Scoring Method B following agitation (110 RPM) at 25° C.

| Formulation | 1 day | 2 days | 3 days | 7 days |
|---|---|---|---|---|
| 24A | 3 | 4 | 5 | 5 |
| 24B | 1 | 1 | 3 | 5 |
| 24C | 2 | 3 | 5 | 5 |
| 24D | 1 | 1 | 1 | 1 |
| 24E | 1 | 2 | 3 | 3 |
| 24F | 5 | 5 | 5 | 5 |
| 24G | 1 | 1 | 4 | 5 |
| 24H | 3 | 3 | 4 | 5 |
| 24I | 1 | 1 | 1 | 2 |
| 24J | 1 | 1 | 2 | 4 |

Example 25—Effect of Surfactants on the Stability of Insulin Aspart in an Injection Pen Cartridge Under Various Stress Conditions The effect of surfactants on the stability of insulin aspart in an injection pen cartridge is investigated at 30° C. and 37° C. both with and without agitation. Sample agitation is carried out using an orbital shaker (100 rpm). All formulations are tested under these stress conditions both with and without a headspace (minimum of 0.5 ml). Stability of the samples is tested by size-exclusion chromatography (formation of soluble aggregates) and by Visual Assessment Scoring Method B (formation of visible particulates). The experiment is designed to mimic the stress experienced during the use of an injection pen. The stability is tested using three different concentrations of insulin—100 U/ml, 500 U/ml and 1000 U/ml. All formulations tested comprise phenol (15.9 mM), m-cresol (15.9 mM), glycerol (300 mM) and sodium phosphate (2 mM) and are adjusted to pH 7.4. Additional ingredients are shown in Table 41. The testing protocol at all stress conditions is shown in Table 42.

TABLE 41

Additional ingredients in formulations (25A-25R) of insulin aspart. All formulations comprise phenol (15.9 mM), m-cresol (15.9 mM), glycerol (300 mM) and sodium phosphate (2 mM) and are adjusted to pH 7.4.

| Formulation | Insulin aspart (U/ml) | Ionic zinc (μg/ml)* | Surfactant (all at 50 μg/ml) | Citric acid (mM) |
|---|---|---|---|---|
| 25A | 100 | 19.7 | None | 0 |
| 25B | 100 | 19.7 | Dodecyl maltoside | 0 |
| 25C | 100 | 19.7 | Decyl glucopyranoside | 0 |
| 25D | 100 | 19.7 | None | 22 |
| 25E | 100 | 19.7 | Dodecyl maltoside | 22 |
| 25F | 100 | 19.7 | Decyl glucopyranoside | 22 |
| 25G | 500 | 98.5 | None | 0 |
| 25H | 500 | 98.5 | Dodecyl maltoside | 0 |
| 25I | 500 | 98.5 | Decyl glucopyranoside | 0 |
| 25J | 500 | 98.5 | None | 22 |
| 25K | 500 | 98.5 | Dodecyl maltoside | 22 |
| 25L | 500 | 98.5 | Decyl glucopyranoside | 22 |
| 25M | 1000 | 197.0 | None | 0 |
| 25N | 1000 | 197.0 | Dodecyl maltoside | 0 |
| 25O | 1000 | 197.0 | Decyl glucopyranoside | 0 |
| 25P | 1000 | 197.0 | None | 22 |
| 25Q | 1000 | 197.0 | Dodecyl maltoside | 22 |
| 25R | 1000 | 197.0 | Decyl glucopyranoside | 22 |

*excluding counter-anion, as $ZnCl_2$.

TABLE 42

Testing protocol for formulations 25A-25R.

| Stress conditions | | | Time-points for testing by SEC |
|---|---|---|---|
| Temperature (° C.) | Agitation | Headspace | and visual assessment (days) |
| 30 | Yes | Yes | 0, 1, 2, 4, 8, 16, 24, 30 |
| 30 | Yes | No | 0, 1, 2, 4, 8, 16, 24, 30 |
| 30 | No | Yes | 0, 1, 2, 4, 8, 16, 24, 30 |
| 30 | No | No | 0, 1, 2, 4, 8, 16, 24, 30 |
| 37 | Yes | Yes | 0, 1, 2, 4, 8, 16, 24, 30 |
| 37 | Yes | No | 0, 1, 2, 4, 8, 16, 24, 30 |
| 37 | No | Yes | 0, 1, 2, 4, 8, 16, 24, 30 |
| 37 | No | No | 0, 1, 2, 4, 8, 16, 24, 30 |

Example 26—Effect of Surfactants on the Stability of Insulin Lispro in an Injection Pen Cartridge Under Various Stress Conditions The protocol of Example 25 is repeated using insulin lispro instead of insulin aspart.

Example 27—Effect of Surfactants on the Stability of Insulin Aspart During a Simulated Use of an Injection Pen The effect of surfactants on the stability of insulin aspart in a pen cartridge is investigated during the use of an insulin pen at 30° C. and 37° C. An insulin composition (either with or without a surfactant) is transferred into the pen cartridge. The cartridge is then placed in the injection pen and the injection pen is placed in an incubator (30° C. or 37° C.) for 30 days. The simulated use of the pen is achieved by agitation of the pen for 60 minutes (orbital shaker, 100 rpm) and dispensing of three 20 μl aliquots each day. The insulin composition dispensed from the pen is collected in a glass container and analysed at regular intervals using size-exclusion chromatography (SEC) (formation of soluble aggregates) and by Visual Assessment Scoring Method B (formation of visible particulates). Insulin stability is tested using three different concentrations of insulin—100 U/ml, 500 U/ml and 1000 U/ml. All formulations tested comprise phenol (15.9 mM), m-cresol (15.9 mM), glycerol (300 mM) and sodium phosphate (2 mM) and are adjusted to pH 7.4. Additional ingredients are shown in Table 43. The testing protocol at all stress conditions is shown in Table 44.

TABLE 43

Additional ingredients in formulations (27A-27R) of insulin aspart. All formulations comprise phenol (15.9 mM), m-cresol (15.9 mM), glycerol (300 mM) and sodium phosphate (2 mM) and are adjusted to pH 7.4.

| Formulation | Insulin aspart (U/ml) | Ionic zinc (μg/ml)* | Surfactant (all at 50 μg/ml) | Citric acid (mM) |
|---|---|---|---|---|
| 27A | 100 | 19.7 | None | 0 |
| 27B | 100 | 19.7 | Dodecyl maltoside | 0 |
| 27C | 100 | 19.7 | Decyl glucopyranoside | 0 |
| 27D | 100 | 19.7 | None | 22 |
| 27E | 100 | 19.7 | Dodecyl maltoside | 22 |
| 27F | 100 | 19.7 | Decyl glucopyranoside | 22 |
| 27G | 500 | 98.5 | None | 0 |
| 27H | 500 | 98.5 | Dodecyl maltoside | 0 |

TABLE 43-continued

Additional ingredients in formulations (27A-27R) of insulin aspart. All formulations comprise phenol (15.9 mM), m-cresol (15.9 mM), glycerol (300 mM) and sodium phosphate (2 mM) and are adjusted to pH 7.4.

| Formulation | Insulin aspart (U/ml) | Ionic zinc (µg/ml)* | Surfactant (all at 50 µg/ml) | Citric acid (mM) |
|---|---|---|---|---|
| 27I | 500 | 98.5 | Decyl glucopyranoside | 0 |
| 27J | 500 | 98.5 | None | 22 |
| 27K | 500 | 98.5 | Dodecyl maltoside | 22 |
| 27L | 500 | 98.5 | Decyl glucopyranoside | 22 |
| 27M | 1000 | 197.0 | None | 0 |
| 27N | 1000 | 197.0 | Dodecyl maltoside | 0 |
| 27O | 1000 | 197.0 | Decyl glucopyranoside | 0 |
| 27P | 1000 | 197.0 | None | 22 |
| 27Q | 1000 | 197.0 | Dodecyl maltoside | 22 |
| 27R | 1000 | 197.0 | Decyl glucopyranoside | 22 |

*excluding counter-anion, as ZnCl$_2$.

TABLE 44

Testing protocol for formulations 27A-27R.

| Stress conditions | | Time-points for testing by SEC and visual assessment (days) |
|---|---|---|
| Temperature (° C.) | Agitation | |
| 30 | Yes | 0, 4, 8, 16, 24, 30 |
| 30 | No | 0, 4, 8, 16, 24, 30 |
| 37 | Yes | 0, 4, 8, 16, 24, 30 |
| 37 | No | 0, 4, 8, 16, 24, 30 |

Example 28—Effect of Surfactants on the Stability of Insulin Lispro During a Simulated Use of an Injection Pen The protocol of Example 27 is repeated using insulin lispro instead of insulin aspart.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

All publications, patents, patent applications, internet sites, and accession numbers/database sequences (including both polynucleotide and polypeptide sequences) cited are herein incorporated by reference in their entirety for all purposes to the same extent as if each individual publication, patent, patent application, internet site, or accession number/database sequence were specifically and individually indicated to be so incorporated by reference.

SEQUENCE LISTING

SEQ ID NO: 1:
GIVEQCCTSICSLYQLENYCN

SEQ ID NO: 2:
FVNQHLCGSHLVEALYLVCGERGFFYTPKT

SEQ ID NO: 3:
FVNQHLCGSHLVEALYLVCGERGFFYTKPT

SEQ ID NO: 4:
FVNQHLCGSHLVEALYLVCGERGFFYTDKT

SEQ ID NO: 5:
FVKQHLCGSHLVEALYLVCGERGFFYTPET

The invention claimed is:

1. An injection pen system comprising an injector mechanism and a reservoir comprising an aqueous liquid pharmaceutical composition for delivery by means of said injector mechanism to a mammal wherein the composition comprises (i) an insulin compound selected from insulin lispro, insulin aspart, insulin glulisine, or recombinant human insulin, (ii) ionic zinc at a concentration of 0.5-1% by weight of zinc based on the weight of insulin compound in the composition and (iii) an alkyl glycoside at a concentration of 10-400 µg/ml as a non-ionic surfactant.

2. The system according to claim 1, wherein the insulin compound is insulin lispro.

3. The system according to claim 1, wherein the insulin compound is insulin glulisine or recombinant human insulin.

4. A system according to claim 1, wherein the insulin compound is insulin aspart.

5. The system according to claim 1, wherein the insulin compound is not recombinant human insulin.

6. The system according to claim 1, wherein the insulin compound is present at a concentration of 10-1000 U/ml; or
    wherein the insulin compound is present at a concentration of 50-1000 U/ml; or
    wherein the insulin compound is present at a concentration of 10-250 U/ml; or wherein the insulin compound is present at a concentration of 400-1000 U/ml; or wherein the insulin compound is present at a concentration of 500-1000 U/ml.

7. The system according to claim 1, wherein the composition further comprises a zinc binding species at a concentration of 1 mM or more selected from species having a log K with respect to zinc ion binding in the range 4.5-12.3 at 25° C.

8. The system according to claim 1, wherein the composition is substantially free of EDTA and any other zinc binding species having a log K with respect to zinc ion binding of more than 12.3 at 25° C.

9. The system according to claim 7, wherein the zinc binding species is selected from citrate, pyrophosphate, aspartate, glutamate, cysteine, cystine, glutathione, ethylenediamine, histidine, DETA and TETA.

10. The system according to claim 9, wherein the zinc binding species is citrate.

11. The system according to claim 10, wherein the source of the citrate is citric acid.

12. The system according to claim 7, wherein the zinc binding species having a log K with respect to zinc ion binding in the range 4.5-12.3 is present at a concentration of 1-60 mM; and/or wherein the molar ratio of ionic zinc to zinc binding species is 1:3 to 1:175.

13. The system according to claim 7, wherein the zinc binding species at a concentration of 1 mM or more is selected from species having a log K with respect to zinc ion binding in the range 4.5-10 at 25° C.

14. The system according to claim 7, which is substantially free of zinc binding species having a log K with respect to zinc ion binding of 10-12.3 at 25° C.

15. The system according to claim 1, wherein the alkyl glycoside is selected from the group consisting of dodecyl maltoside, dodecyl glucoside, octyl glucoside, octyl maltoside, decyl glucoside, decyl maltoside, decyl glucopyranoside, tridecyl glucoside, tridecyl maltoside, tetradecyl glucoside, tetradecyl maltoside, hexadecyl glucoside, hexadecyl maltoside, sucrose monooctanoate, sucrose monodecanoate, sucrose monododecanoate, sucrose monotridecanoate, sucrose monotetradecanoate and sucrose monohexadecanoate.

16. The system according to claim 15, wherein the alkyl glycoside is dodecyl maltoside or decyl glucopyranoside.

17. The system according to claim 16, wherein the alkyl glycoside is dodecyl maltoside.

18. The system according to claim 1, wherein the alkyl glycoside is present at a concentration of 10-100 ug/ml.

19. The system according to claim 18, wherein the alkyl glycoside is dodecyl maltoside or decyl glucopyranoside.

20. The system according to claim 1, wherein the composition further comprises a tonicity modifying agent.

21. The system according to claim 20, wherein the tonicity modifying agent is an uncharged tonicity modifying agent selected from the group consisting of trehalose, mannitol, glycerol and 1,2-propanediol.

22. The system according to claim 21, wherein the uncharged tonicity modifying agent is glycerol.

23. The system according to claim 20, wherein the tonicity modifying agent is a charged tonicity modifying agent which is sodium chloride.

24. The system according to claim 1, wherein the ionic strength of the composition excluding any zinc binding species and the insulin compound is <40 mM, wherein ionic strength is calculated according to the formula I:

$$I = 0.5 \times \sum_{X=1}^{n} c_x z_x^2$$

in which $c_x$ is molar concentration of ion x (mol L$^{-1}$), $z_x$ is the absolute value of the charge of ion x and the sum covers all ions (n) present in the composition, wherein the contribution of the insulin compound and zinc binding species, if present should be ignored for the purposes of the calculation.

25. The system according to claim 1, wherein the composition is substantially isotonic.

26. The system according to claim 1, wherein the pH of the composition is in the range 5.5 to 9.0.

27. The system according to claim 26, wherein the pH of the composition is in the range 7.0 to 7.5; or wherein the pH of the composition is in the range 7.6 to 8.0.

28. The system according to claim 27, wherein the composition comprises a phosphate buffer.

29. The system according to claim 1, wherein the composition further comprises a preservative selected from the group consisting of phenol, m-cresol, chlorocresol, benzyl alcohol, propylparaben, methylparaben, benzalkonium chloride and benzethonium chloride.

30. The system according to claim 1, wherein the composition further comprises nicotinamide; and/or further comprises nicotinic acid or a salt thereof; and/or further comprises treprostinil or a salt thereof.

31. The system according to claim 1, wherein the composition comprises (i) an insulin compound at a concentration of 50-500 U/ml (ii) ionic zinc, (iii) optionally citrate as a zinc binding species at a concentration of 1 mM or more, and (iv) a non-ionic surfactant which is an alkylglycoside; and wherein the composition is substantially free of EDTA and any other zinc binding species having a log K with respect to zinc ion binding of more than 12.3 at 25° C.

32. The system according to claim 31, wherein the citrate is present in the composition at a concentration of 10-30 mM.

33. The system according to claim 1, wherein the composition comprises (i) an insulin compound at a concentration of 400-1000 U/ml (ii) ionic zinc, (iii) optionally citrate as a zinc binding species at a concentration of 1 mM or more, and (iv) a non-ionic surfactant which is an alkyl glycoside; and wherein the composition is substantially free of EDTA and any other zinc binding species having a log K with respect to zinc ion binding of more than 12.3 at 25° C.

34. The system according to claim 33, wherein the citrate is present in the composition at a concentration of 30-60 mM; and/or wherein the ionic strength of the composition is less than 40 mM calculated using Formula I; and/or wherein the composition comprises <10 mM chloride; and/or wherein the composition comprises an uncharged tonicity modifying agent.

35. The system according to claim 1, wherein the composition comprises an insulin compound at a concentration of 400-1000 U/mL and wherein the composition is bioequivalent to a standard composition comprising the insulin compound at a concentration of 100 U/mL.

36. The system according to claim 1, wherein the absorption of insulin compound into the blood stream of the mammal after administration using the system is bioequivalent to a standard composition comprising the insulin compound at a concentration of 100 U/mL.

37. The system according to claim 1, wherein the glucose reduction response caused by administration of a given amount of insulin compound to the mammal using the system is bioequivalent to a standard composition comprising the insulin compound at a concentration of 100 U/mL.

38. The system according to claim 1, comprising a dial mechanism enabling selection of a specific desired volume of the composition for delivery to the mammal.

39. The system according to claim 38, wherein the volume of composition selected for delivery is between 0.1-100 μL.

40. The system according to claim 39, wherein the selected volume is determined by the dial mechanism in increments of 0.1-10 μL.

41. The system according to claim 1, wherein the reservoir has a total volume of up to 3 mL.

42. The system according to claim 1, wherein the ratio between the delivered dose of insulin compound delivered (U) and the delivered volume (μL) is at least 0.4:1.

43. The system according to claim 1, wherein the composition is more stable than an identical composition in the absence of alkyl glycoside during operation of the pen for 4 weeks or more.

44. The system according to claim 1, wherein the injection pen is disposable.

45. The system according to claim 44, wherein the injection pen is to be disposed of after use for up to 4 weeks.

46. The system according to claim 1, wherein the injection pen system is reusable and the reservoir is replaced as needed.

47. The system according to claim 46, wherein the reservoir is to be disposed of after the use for up to 4 weeks.

48. The system according to claim 1, wherein the injector mechanism comprises a retractable needle.

49. The system according to claim 48, wherein the injector mechanism comprises a spring loaded retractable needle.

50. A method of treatment of diabetes mellitus which comprises administering to a mammal in need thereof an effective amount of an insulin compound containing composition via an injection pen using a system according to claim 1.

51. The method according to claim 50, wherein the mammal requires 200 U of insulin per day or more.

52. The method according to claim 50, wherein the mammal has developed insulin resistance.

53. The method according to claim 50, wherein the mammal is a human.

54. A method of improving the stability of an insulin compound to be administered by an injection pen system, which comprises adding an alkyl glycoside to an aqueous liquid pharmaceutical composition comprising the insulin compound and ionic zinc.

* * * * *

SEQUENCE LISTING

<160> NUMBER OF SEQ ID NOS: 5

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

```
<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: B chain of insulin lispro

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: B chain of insulin aspart

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: B chain of insulin glulisine

<400> SEQUENCE: 5

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Thr
            20                  25                  30
```